US012588819B2

(12) United States Patent　　　(10) Patent No.:　US 12,588,819 B2

Simpson et al.　　　　　　　　　　(45) Date of Patent:　　Mar. 31, 2026

(54) OCT CATHETER WITH LOW REFRACTIVE INDEX OPTICAL MATERIAL

(71) Applicants:Simpson Interventions, Inc., Woodside, CA (US); John B. Simpson, Woodside, CA (US); Kin Foong Chan, Woodside, CA (US)

(72) Inventors: John B. Simpson, Woodside, CA (US); Kin Foong Chan, Woodside, CA (US); Wendy Lam, Woodside, CA (US); Sergio Salinas, Woodside, CA (US); Evangeline Lumabas, Woodside, CA (US)

(73) Assignee: Elumn8 Medical, Inc., Campbell, CA (US)

( * ) Notice: Subject to any disclaimer, the term of this patent is extended or adjusted under 35 U.S.C. 154(b) by 116 days.

(21) Appl. No.: 17/920,654

(22) PCT Filed: Apr. 22, 2021

(86) PCT No.: PCT/US2021/028723

§ 371 (c)(1),
(2) Date: Oct. 21, 2022

(87) PCT Pub. No.: WO2021/216933

PCT Pub. Date: Oct. 28, 2021

(65) Prior Publication Data

US 2023/0141567 A1　　　May 11, 2023

Related U.S. Application Data

(60) Provisional application No. 63/014,110, filed on Apr. 22, 2020, provisional application No. 63/165,672, filed on Mar. 24, 2021.

(51) Int. Cl.
*A61B 5/00*　　　　(2006.01)

(52) U.S. Cl.
CPC .......... *A61B 5/0066* (2013.01); *A61B 5/0084* (2013.01); *A61B 5/6876* (2013.01)

(58) Field of Classification Search
CPC ... A61B 5/0066; A61B 5/0084; A61B 5/6876; A61B 5/6852; A61B 5/743;
(Continued)

(56) References Cited

U.S. PATENT DOCUMENTS

| | | | |
|---|---|---|---|
| 3,499,107 A | 3/1970 | Sheldon | |
| 3,915,924 A | 10/1975 | Wright | |

(Continued)

FOREIGN PATENT DOCUMENTS

| | | | |
|---|---|---|---|
| JP | 61281051 | 12/1986 | |
| JP | 2016524992 A | 8/2016 | |

(Continued)

OTHER PUBLICATIONS

Resnick et al., Teflon AF Amorphous Fluoropolymers, Modern Fluoropolymers, 1997.*

(Continued)

*Primary Examiner* — Bo Joseph Peng
(74) *Attorney, Agent, or Firm* — Dorsey & Whitney LLP

(57)　　　　　　ABSTRACT

Embodiments of the disclosure include apparatuses, systems, and methods for a catheter with a single element for both imaging and interventions. The catheter may have a distal tip which is positionable in a patient (e.g., in a lumen of a vessel). The distal tip may have an optical component which includes both a reflecting surface and a tapered distal end. The reflecting surface may redirect light (e.g., light received along an optical fiber of the catheter) into an imaging beam, which may be directed to a wall of the vessel. The tapered distal end may be a crossing tool used to cross an occluded or partially-occluded section of the vessel. In some embodiments, the reflecting surface and tapered distal (Continued)

end may be the same surface of the optical component. A low refractive index optical filler may be provided to reduce image artifacts at the imaging interface with the patient's fluid and tissue.

26 Claims, 40 Drawing Sheets

(58) Field of Classification Search
CPC .. A61B 17/320758; A61B 2017/22094; A61B 2090/3735; G02B 23/2423; G02B 6/262
See application file for complete search history.

(56) References Cited

U.S. PATENT DOCUMENTS

| | | | |
|---|---|---|---|
| 5,190,028 A | 3/1993 | Lafferty et al. | |
| 5,622,417 A | 4/1997 | Conner et al. | |
| 5,836,664 A | 11/1998 | Conner et al. | |
| 6,174,424 B1 * | 1/2001 | Wach | G01N 21/7703 |
| | | | 205/79 |
| 6,974,557 B1 | 12/2005 | Webler et al. | |
| 8,552,083 B1 | 10/2013 | Taranekar et al. | |
| 10,524,816 B2 | 1/2020 | Dell'Oca | |
| 2002/0146202 A1 * | 10/2002 | Reed | G02B 6/14 |
| | | | 385/34 |
| 2003/0031410 A1 | 2/2003 | Schnitzer | |
| 2003/0095739 A1 * | 5/2003 | Kim | G02B 6/3588 |
| | | | 385/33 |
| 2003/0185513 A1 * | 10/2003 | Hellman | G02B 6/2937 |
| | | | 385/47 |
| 2004/0017961 A1 | 1/2004 | Petersen et al. | |
| 2004/0091196 A1 | 5/2004 | Li et al. | |
| 2004/0240034 A1 | 12/2004 | Scharf et al. | |
| 2005/0226582 A1 * | 10/2005 | Nagelvoort | C09D 4/06 |
| | | | 385/128 |
| 2006/0051036 A1 | 3/2006 | Treado et al. | |
| 2006/0106287 A1 | 5/2006 | Webler et al. | |
| 2007/0121213 A1 * | 5/2007 | Tseng | G02B 26/005 |
| | | | 359/628 |
| 2009/0323076 A1 * | 12/2009 | Li | G01B 9/02063 |
| | | | 356/479 |
| 2010/0023042 A1 | 1/2010 | Dell | |
| 2010/0253949 A1 | 10/2010 | Adler et al. | |
| 2010/0308571 A1 | 12/2010 | Steenblik et al. | |
| 2011/0137117 A1 | 6/2011 | Jacobsen et al. | |
| 2011/0137177 A1 | 6/2011 | Toma et al. | |
| 2012/0140301 A1 * | 6/2012 | Xu | G02B 3/00 |
| | | | 359/198.1 |
| 2014/0066756 A1 | 3/2014 | Sinclair et al. | |
| 2014/0249407 A1 | 9/2014 | Adler et al. | |
| 2014/0276108 A1 * | 9/2014 | Vertikov | A61B 5/0066 |
| | | | 600/478 |
| 2015/0025369 A1 | 1/2015 | Bhagavatula et al. | |
| 2015/0099984 A1 | 4/2015 | Kankaria | |
| 2017/0099237 A1 | 4/2017 | Lan | |
| 2017/0238803 A1 | 8/2017 | Kankaria | |
| 2017/0311806 A1 * | 11/2017 | Comstock, II | A61B 5/0066 |
| 2018/0055342 A1 | 3/2018 | Sakai et al. | |
| 2019/0099237 A1 | 4/2019 | Booker et al. | |
| 2019/0223699 A1 | 7/2019 | Wu | |
| 2019/0374092 A1 | 12/2019 | Wu et al. | |

FOREIGN PATENT DOCUMENTS

| | | |
|---|---|---|
| JP | 2018138173 A | 9/2018 |
| WO | 2009137704 A1 | 11/2009 |
| WO | 2021216933 | 10/2021 |
| WO | 2022204441 | 9/2022 |

OTHER PUBLICATIONS

Specialchem, Low & Ultra-low Refractive Index Polymers, SpecialChem, Jan. 17, 2011; https://omnexus.specialchem.com/tech-library/article/low-ultra-low-refractive-index-polymers.*

Canak et al., Synthesis of fluorinated urethane acrylate based UV-curable coatings, Progress in Organic Coatings, vol. 76, Issues 2-3, Feb.-Mar. 2013, pp. 388-399.*

Norland Products, Norland Adhesive Selector Guide, wayback machine captured on Jul. 31, 2018, https://web.archive.org/web/20180731131928/http://www.norlandprod.com/adhchart.html.*

Norland Optical Adhesive 1369, Safety Data Sheet, Date prepared Oct. 17, 2016, wayback machine captured on Mar. 15, 2017, https://web.archive.org/web/20170315012956/https://www.norlandprod.com/msds/NOA1369sds.html.*

International Search Report and Written Opinion issued in International Application No. PCT/US2022/021812, mailed on Jun. 14, 2022, 7 pages.

International Search Report and Written Opinion received in PCT/US2021/028723 dated Aug. 4, 2021.

Extended European Search Report issued in European Patent Application No. 21792974.4, mailed on Dec. 12, 2024, 9 pages.

International Preliminary Report on Patentability issued in International Application No. PCT/US2021/028723, mailed on Nov. 3, 2022, 20 pages.

International Preliminary Report on Patentability issued in International Application No. PCT/US2022/021812, mailed on Oct. 5, 2023, 6 pages.

Office Action issued in Japanese Application No. 2022-564622, mailed on Mar. 5, 2025, 6 pages including 3 pages of machine English translation.

Office Action issued in Chinese Patent Application No. 202180044127.1, issued on Dec. 12, 2025, 19 pages including 8 pages of English translation.

* cited by examiner

502

504

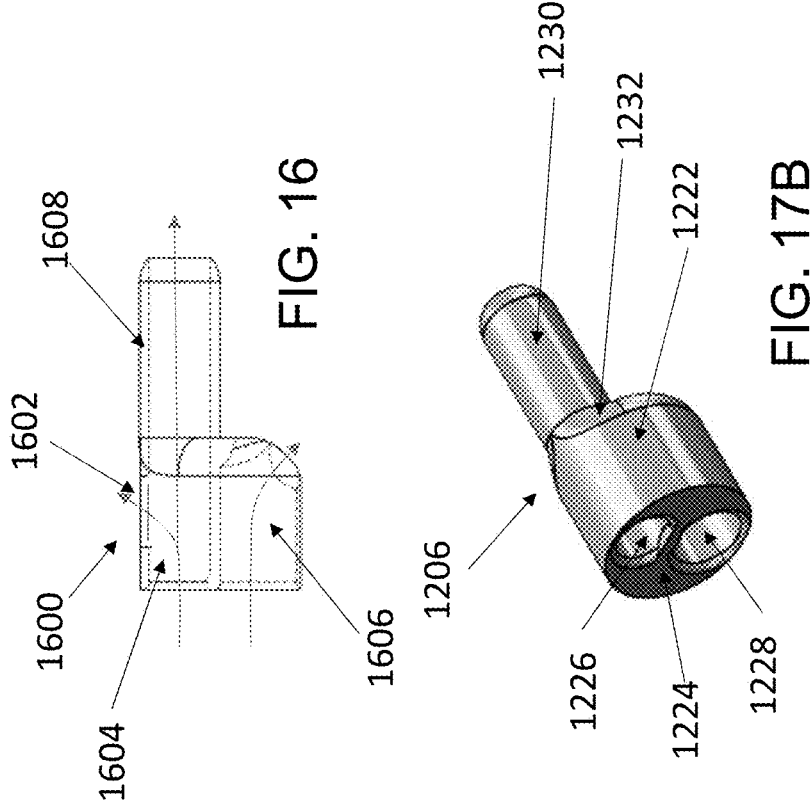
FIG. 16
FIG. 17B
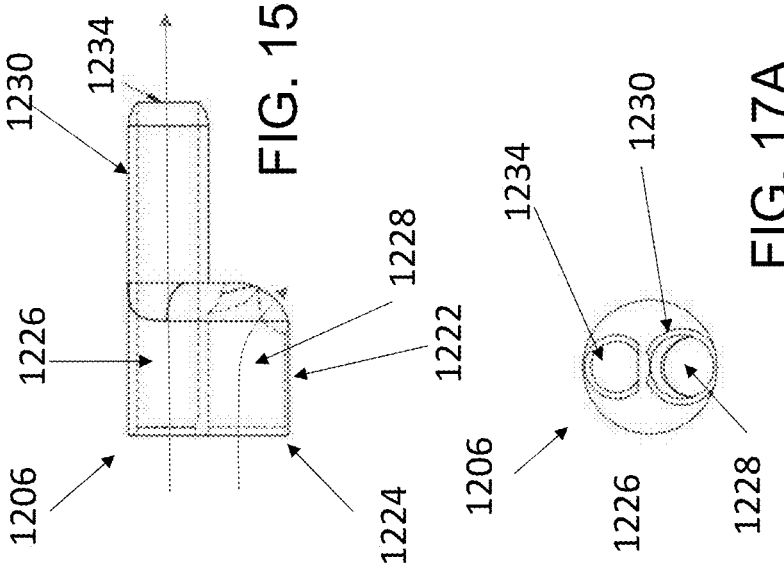
FIG. 15
FIG. 17A

2010

2012

2702 2760

2762

2764

OCT CATHETER WITH LOW REFRACTIVE INDEX OPTICAL MATERIAL

CROSS-REFERENCE TO RELATED APPLICATIONS

This application is a National Phase entry under 35 U.S.C. 371 of International Application No. PCT/US2021/028723 filed Apr. 22, 2021, which in turn claims the priority benefit of U.S. Provisional Application Ser. No. 63/165,672, filed Mar. 24, 2021 and U.S. Provisional Application Ser. No. 63/014,110, filed Apr. 22, 2020, which are hereby incorporated by reference in their entirety. This application is also related to U.S. Provisional Application Ser. No. 63/165,673, filed Mar. 24, 2021, which is hereby incorporated by reference in its entirety.

TECHNICAL FIELD

Embodiments herein relate generally to endovascular imaging, total-occlusion crossing, and atherectomy devices, and particularly, to interferometric imaging devices with a single element for interventions and imaging, imaging and intervention system, and methods of operation.

BACKGROUND

Minimally invasive interventions have consistently shown to be of equivalent or greater efficacy and offer lower mortality rates than traditional open surgical interventions. For many such minimally invasive procedures, being able to accurately track the positioning of instruments inserted into the vasculature of the patient is of the utmost importance for surgeons and other medical professionals undertaking such interventions. A majority of minimally invasive procedures involve the use of a flexible guidewire and catheters that are directed to a target vessel site using the guidewire. However, steering the guidewire to the target vessel site can be challenging and fraught with risks. For example, an improperly maneuvered guidewire can cause harmful vascular dissection, perforation, or thrombosis. While some of these risks can be offset by heparinization, the increased use of such anti-coagulants can increase the risk of procedural hemorrhage.

Moreover, most guidewire navigation is currently done under X-ray fluoroscopic imaging. However, X-ray imaging often requires the surgeon or other medical professionals to be subjected to long bouts of radiation.

Therefore, improved devices, systems, and methods for endovascular imaging are needed which address the challenges faced by current devices on the market. Such a solution should lower the risk of complications for patients and reduce the risk of radiation exposure for operators. Moreover, such a solution should be compatible or easily adapted for use with other minimally invasive surgical devices such as atherectomy catheters. Furthermore, such a solution should reduce the complexity of current devices and be cost-effective to manufacture. The endovascular imaging devices, systems and methods may also be configured to improve imaging quality and/or to reduce various image artifacts.

SUMMARY

Embodiments of the disclosure are drawn to apparatuses, systems, and methods for a catheter, guidewire or interventional device with a single element tip for both imaging and interventions. The catheter may have a distal tip which is positionable in a patient (e.g., in a lumen of a vessel). The distal tip may have a component or block which includes both an optical feature and a mechanical feature for piercing through and/or insertion across an atherosclerotic plaque. The optical feature may redirect light (e.g., light received along an optical fiber of the catheter) into an imaging beam, which may be directed to a wall of the vessel, while the mechanical feature is configured to facilitate the crossing of an occluded or partially-occluded section of the vessel via an angled tip. The imaging component or assembly may also be configured to reduce one or more imaging artifacts.

In one embodiment, an imaging device is provided, comprising an outer shaft with a lumen, an optical fiber located within the lumen of the outer shaft, a reflective element disposed in the lumen of the outer shaft, wherein the reflective element comprises an optical material with an angled surface configured to an imaging beam, and a first optical filler between the distal end of the optical fiber and the reflective element, the first optical filler comprising a refractive index of less than 1.40. The refractive index of the first optical filler may be in the range of 1.30 to 1.40 or 1.33 to 1.38. The optical filler may comprise an aliphatic urethane acrylate and an acrylic monomer. The aliphatic urethane acrylate percentage may be 30% to 70% and the acrylic monomer may 70% to 30%, or the aliphatic urethane acrylate percentage may be 40% to 65% and the acrylic monomer may be 60% to 35%. The viscosity of the first optical filler may be in the range of 1000 to 3000 cps, 1500 to 3000 cps, or 2000 to 2500 cps. The imaging device of claim 1, further comprising a lens located between the optical fiber and the reflective element. The lens may be a Fresnel lens, GRIN lens, plano-convex or double-convex lens. The lens may be tilted between 0.1 to 2.0 degrees. The imaging device may further comprise a non-clad fiber followed by a GRIN lens between the optical fiber and the reflective element. The first optical filler may be further located between the lens and the reflection element. The imaging device may further comprise a second optical filler located between the optical fiber and the lens. The first optical filler and the second optical filler may comprise different materials, or may comprise the same constituents but at different ratios, and wherein both the first and second optical filler have a refractive index of less than 1.50. The angled surface of the reflection element may comprise a Fresnel diffractive pattern. The Fresnel diffractive pattern may comprise varying degree of collimating or focusing power along its long axis, short axis and in between the long and short axes. The imaging device may further comprise a lens located between the optical fiber and the reflection element. The lens may be a GRIN lens. The first optical filler may be located between the lens and the reflective element. The reflection element may further comprise a tapered distal end protruding from the lumen of the outer shaft, wherein the tapered distal end is configured to penetrate tissue. The first optical filler comprises a UV cured optical material. A collimating lens may be located between the optical fiber and the first optical filler. The collimating lens may be a GRIN lens, and plano-convex, or biconvex or a Fresnel lens.

In another example, an imaging device is provided, comprising an outer shaft with a lumen, an optical fiber located within the lumen of the outer shaft, a reflective element disposed in the lumen of the outer shaft, wherein the reflective element comprises an optical material with an angled surface configured to an imaging beam, a beam-collimating element between the optical fiber and a first optical filler, and a first optical filler between the distal end of the beam-collimating element and the reflective element, the first optical filler comprising a refractive index of less than 1.40. An interface between the beam-collimating element and the first optical filler has a return loss or reference signal between −15 dB and −28 dB, −20 dB and −35 dB, or −23 dB and −40 dB. The beam-collimating element may be a Fresnel lens or a GRIN lens.

In still another example, an imaging device is provided, comprising an outer shaft with a lumen, an optical fiber located within the lumen of the outer shaft, a reflective element disposed in the lumen of the outer shaft, wherein the reflective element comprises an optical material with an angled surface configured to an imaging beam, a beam-collimating segment between the optical fiber and a first optical filler comprising of a non-clad fiber and a GRIN lens, and a first optical filler between the distal end of the GRIN lens and the reflective element, the first optical filler comprising a refractive index of less than 1.40. An interface between the beam-collimating element and the first optical filler may have a return loss or reference signal between −15 dB and −28 dB, −20 dB and −35 dB, or −23 dB and −40 dB. An interface between the optical fiber and the non-clad fiber, and the interface between the non-clad fiber and the GRIN lens may have reflection artifacts weaker than −40 dB.

In another variation, an imaging device is provided, comprising an outer shaft with a lumen, an optical fiber located within the lumen of the outer shaft, a reflective element disposed in the lumen of the outer shaft, wherein the reflective element comprises an optical material with an angled surface configured to an imaging beam, a beam-collimating segment between the optical fiber and a first optical filler consisting a GRIN lens, and a first optical filler between the distal end of the GRIN lens and the reflective element, the first optical filler comprising a refractive index of less than 1.40. An interface between the beam-collimating element and the first optical filler may have a return loss or reference signal between −15 dB and −28 dB, −20 dB and −35 dB, or −23 dB and −40 dB.

In still another variation, an imaging device is provided, comprising an outer shaft with a lumen, an optical fiber located within the lumen of the outer shaft, a reflective element disposed in the lumen of the outer shaft, wherein the reflective element comprises diffractive patterns on a flat surface of an optical material with an angled surface configured to an imaging beam, and a first optical filler between the optical fiber and the reflective element, the first optical filler comprising a refractive index of less than 1.40. The imaging device may further comprise a lens located between the optical fiber and the reflective element. The lens may be a Fresnel lens, plano-convex or double-convex lens. The lens may be tilted between 0.1 to 2.0 degrees. The lens may be a GRIN lens. The lens may comprise a non-clad fiber followed by a GRIN lens.

In another embodiment, an imaging device is provided, comprising an outer shaft with a lumen, an optical fiber located within the lumen of the outer shaft, a reflective element disposed in the lumen of the outer shaft, wherein the reflective element comprises diffractive patterns on a flat surface having varying degree of collimating and focusing power between its long and short axes, with an angled surface configured to an imaging beam, and a first optical filler between the optical fiber and the reflective element, the first optical filler comprising a refractive index of less than 1.40. The imaging device may further comprise a lens located between the optical fiber and the reflective element. The lens may be a Fresnel lens, plano-convex or double-convex lens. The lens may be tilted between 0.1 to 2.0 degrees. The lens may also be a GRIN lens, or comprise a non-clad fiber followed by a GRIN lens In another example, an imaging device is provided, comprising an optical fiber, a reflective element with an angled surface configured to an imaging beam, a beam-collimating GRIN lens having at least 0.75 pitch or more in unit length, and a first optical filler between the distal surface of the GRIN lens and the reflective element, the first optical filler comprising a refractive index of less than 1.40. An interface between the optical fiber and the GRIN lens produces a reflection artifact stronger or weaker than −40 dB.

In still another embodiment, an imaging device is provided, comprising an optical fiber, a reflective element with an angled surface configured to an imaging beam, a beam-collimating GRIN lens having at least 0.75 pitch or more in unit length, having a reflection artifact at the interface between the optical fiber and the GRIN lens that is stronger than −40 dB, and a first optical filler between the distal surface of the GRIN lens and the reflective element, the first optical filler comprising a refractive index of less than 1.40.

In still another embodiment, an imaging device is provided, comprising an outer shaft with a lumen, an optical fiber located within the lumen of the outer shaft, a reflective element disposed in the lumen of the outer shaft, wherein the reflective element comprises diffractive patterns on a flat surface having varying degree of collimating and focusing power between its long and short axes, with an angled surface configured to an imaging beam, a beam-collimating element between the optical fiber and a first optical filler, and a first optical filler between the distal end of the beam-collimating element and the reflective element, the first optical filler comprising a refractive index of less than 1.40.

BRIEF DESCRIPTION OF THE DRAWINGS

FIGS. 15 and 16 are schematic side views of different guide catheter tips that may be used.

FIGS. 17A and 17B are proximal elevational and perspective views of the guide catheter tip in FIG. 15.

DETAILED DESCRIPTION

Figure 1:
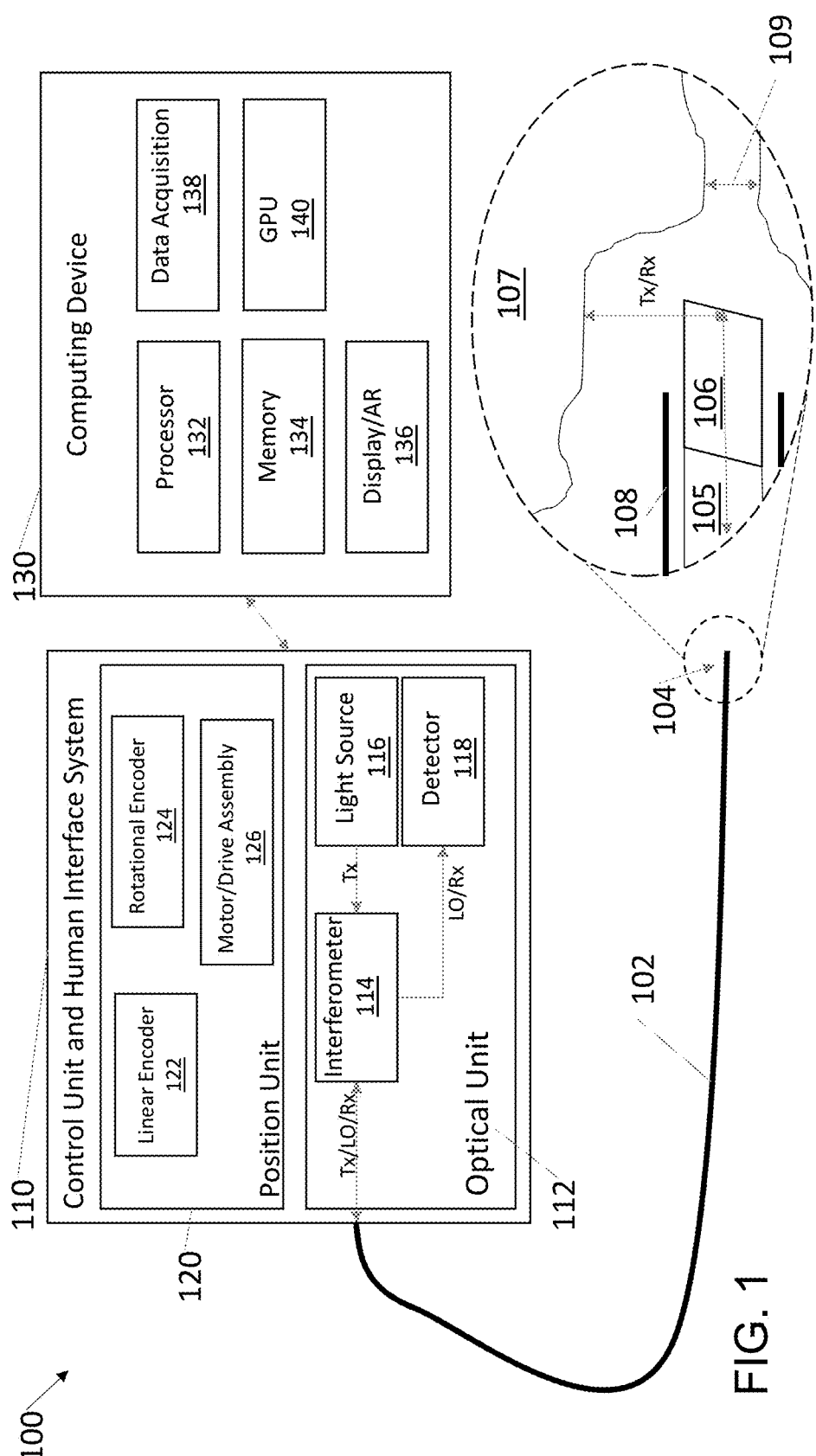
FIG. 1 is a schematic diagram of an imaging and intervention system according to some embodiments of the present disclosure.

The following description of certain embodiments is merely exemplary in nature and is in no way intended to limit the scope of the disclosure or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the disclosure. Moreover, for the purpose of clarity, detailed descriptions of certain features will not be discussed when they would be apparent to those with skill in the art so as not to obscure the description of embodiments of the disclosure. The following detailed description is therefore not to be taken in a limiting sense, and the scope of the disclosure is defined only by the appended claims.

Minimally invasive medical interventions may involve insertion of a catheter through the lumen of one or more vessels of a patient. For example, during atherectomy, a catheter or guidewire may be advanced through a blood vessel of a patient and one or more intervention tools inserted into the working lumen of the catheter or over the guidewire to remove (or otherwise decrease the volume of) an atherosclerotic plaque. In some variations, the progress of the catheter advancement through the patient may be monitored, for example to reduce the risk of piercing or dissection of the vascular wall, and/or to monitor the progress of plaque or clot removal.

The imaging device includes an optical assembly or element which allows for imaging of the walls of the vessel that the imaging device is disposed in. In general, the imaging device may be coupled to an optical system, which may direct light along the imaging device (e.g., along one or more optical fibers of the imaging device). The reflecting surface may be located at a distal region of the imaging device and may redirect the light to illuminate the vessel lumen and walls. The reflecting surface may also redirect light received from the vessel lumen and walls back along the imaging device to the optical system. For example, the imaging device may be an interferometric imaging device which may perform optical coherence tomography (OCT) by scanning light along the walls of a vessel, generating an interferometric pattern by combining light reflected (or scattered) from the vessel walls with light reflected from a reference surface, and imaging the vessel walls based on the interferometric pattern. The imaging device may also be configured to with an angled or tapered geometry to facilitate crossing of occluded vasculature. This interventional feature and the reflecting surface may be integrated together. It may be useful to reduce the size and bulk of the imaging device to increase its ability to travel through relatively narrow or occluded vessels. This may be achieved, for example, using an optical structure that includes the reflection surfaces and the angled or tapered surfaces for crossing occlusions.

The present disclosure is directed to an interferometric imaging device with single element for interventions and imaging, imaging and intervention system, and methods of operation thereof. The interferometric imaging device includes an optical component at a distal end of the imaging device. The optical component includes both an imaging feature and crossing element. For example, the imaging feature may be a reflective surface of the optical component, at an angle relative to the long axis of the imaging device to redirect light between the long axis of the imaging device and a side surface of the imaging device. The optical component may also include a geometric configuration which may be an angled, tapered, cutting or penetrating surface to facilitate crossing or navigation through a plaque, occlusion or clot as the imaging device passes along the vessel. The mechanical geometry may also be configured with a tissue contact surface to penetrate, cut or abrade the plaque. The tissue contact surface of the optical component may be adjustably extendable from an end or a portion of the imaging device. In some embodiments, the tissue contact surface which forms the tapered distal end and the reflective surface which forms the reflecting surface may be the same surface of the optical component.

For example, the distal tip component may be a monolithic, optically transparent component or structure in which the optical feature is an angled internal reflection surface of distal geometry region of the structure. The structure may also comprise a tapered geometry to facilitate selective penetration and passage through an occluded portion of the vasculature, and wherein the distal geometry region of the structure comprises an angled external surface corresponding to the angled internal reflection surface. The corresponding internal and external points, surfaces or regions on the structure may be the opposing internal and external geometries, the parallel internal and external geometries, and/or the immediately orthogonal or normal internal and external points, surfaces or regions. The distal geometry region and/or other surfaces of the structure may comprise a coating to augment the reflection or other optical properties of the structure.

FIG. 1 is a schematic diagram of an imaging and intervention system according to some embodiments of the present disclosure. The imaging system 100 includes a guidewire, catheter or imaging device 102, all or a portion of which may be inserted into a patient. A distal tip 104 of the imaging device 102 may be used for imaging of tissues of the patient and/or one or more interventions in the patient. A proximal end of the imaging device 102 is coupled to a control unit 110 which may be used to perform the imaging and/or intervention through the imaging device 102. An optional computing device 130 may be coupled to the control unit 110 in order to operate or interface with the control unit 110 feeding imaging data from the optical unit and human interface devices/position unit back to the control unit 110, and/or record/store/interpret/augment data (e.g., imaging data) generated by the control unit 110. Control unit 110 may optionally consist of a graphical processing unit to enhance data received from the optical unit and human interface devices/position unit using a neural network to improve visualization and image guidance for the physician through the Display 136.

The inset of FIG. 1 depicts an expanded schematic view of a distal tip 104 of the imaging device 102. The imaging device 102 includes an outer shaft 108, and an inner member 105 which includes an optical component 106. The optical component 106 may include a reflecting surface which is used for imaging tissue 107 around the distal tip 104 of the imaging device 102 and also includes a tapered distal end which is used to perform one or more interventions. For example, the optical component 106 may include a crossing element for crossing a narrowing or obstruction in a vessel, such as the total or partial occlusion 109. The tissue 107 may be a wall of a vessel that the distal tip 104 is positioned in. For example, the tissue 107 may be the wall of a coronary blood vessel.

The control unit 110 includes a position unit 120 and an optical unit 112. Although shown as a single control unit 110 in the example of FIG. 1, it should be understood that the human interface devices/position unit 120 and optical unit 110 may be separate components of the system 100 in some embodiments. The human interface devices/position unit 120 may be used to control and/or track the position of the imaging device 102 and/or one or more components of the imaging device 102 relative to the imaging device 102. The optical unit 110 may image the tissue 107 around the distal tip 104 by providing and receiving light through the imaging device.

The optical unit 112 may be used to perform optical coherence tomography (OCT). The optical unit 112 includes a light source 116 which provides transmitted light Tx. The light source 116 may be a laser, a light emitting diode (LED), an arc lamp, incandescent source, fluorescent source, other source of light, or combinations thereof. The transmitted light Tx may have a relatively narrow bandwidth centered on a particular frequency, may be broadband source (e.g., white light), or combinations thereof. In some embodiments, the light source 116 may be a swept source laser, and a center frequency of the transmitted light Tx may change over time. In some embodiments, the center frequency of the transmitted light may be chosen to penetrate tissue. For example, the center frequency may be in the near infra-red (NIR) window where tissue has a relatively low extinction (e.g., between about 800 nm and 1400 nm).

The optical unit 112 includes an interferometer 114, which receives the transmitted light Tx and provides it along the imaging device 102. For example, the interferometer 114 may couple the transmitted light into an optical fiber which runs along the length imaging device 102. The interferometer may also receive light from the imaging device 102 (e.g., received light along the optical fiber) and provide the received light to a detector 118. The received light may include a portion of receive light Rx which has interacted with the tissue 107 and a local oscillator LO portion of the light which was reflected from a reference surface. The interferometer 114 may include a Faraday isolation device, such as a Faraday Effect optical circulator which may separate the optical paths of the returning received light Rx and local oscillator LO light from the transmitted light Tx. The separated Rx and LO light may then be directed to the detector 118. In some embodiments, the optical unit 112 may include additional components (e.g., lenses, filters, etc.) which may improve the performance of the optical unit 112 and/or add additional functionality.

In some embodiments, the system 100 may be a common-path OCT system, and the reference surface may be an end of the optical fiber in component 104, where Fresnel reflection causes a portion of the transmitted light Tx to reflect off the end of the fiber, while another portion of the transmitted light exits the fiber to interact with the optical component 104 (and from there the tissue 107). In other embodiments, the system 100 may consist of a reference arm as the reference surface separately from the optical fiber in component 104.

The transmitted light Tx may interact with the tissue 107, and a portion of the light may be redirected (e.g., scattered, reflected, or combinations thereof) along an optical path which causes the redirected light to re-enter the catheter 102 and return to the optical unit 112 as received light Rx. The received light Rx may travel a longer distance the LO light, and so there may be a difference of frequency, phase, and/or time between the Rx and LO light. These differences may be used by the detector 118 (and/or computing device 130) to determine properties of the tissue 107. For example, the received light Rx and local oscillator LO light may interfere with each other to generate an interference pattern at the detector 118. The interference pattern may be interpreted (e.g., by the computing device 130) to extract information about the difference between the distance the received light Rx travelled compared to the distance the LO light travelled. In the case of swept source OCT, the difference may be encoded as a beat frequency heterodyned on the carrier reference beam.

The detector 118 may convert light incident on the detector 118 (e.g., the received light Rx and LO light) into an electrical signal. For example, the detector 118 may be an array detector (e.g., a CCD or CMOS) which provides a signal based on an amount and/or color of light incident on each pixel of the array.

The outer shaft 108 can be a long flexible tube configured to allow components such as a guidewire, an imaging component, a drive shaft, sensor wires or fibers, imaging wires or fibers, cables, protective sheaths, parts therein, or a combination thereof to extend or pass through the imaging device lumens of the imaging device 102. The human interface devices/position unit 120 may track and control both the position of the outer shaft 108, and also the inner member 105 relative to the outer shaft 108. For example, the position unit 120 may extend/retract the inner member 105 relative to the outer shaft 108 and/or rotate the inner member 105 relative to the outer shaft 108.

The human interface devices/position unit 120 can include a number of electromechanical devices or sensors that convert the translational or angular/rotational motion of the imaging device 102, the inner member 105, or a combination thereof into digital signals or data. For example, the position unit 120 can comprise one or more linear encoders 122, rotary encoders 124, or a combination thereof. Human control and sensory feedback from the human interface devices/position unit 120 may be used to augment image visualization through the use of and integration with a neural network in order to provide improved guidance to the physician during a procedure.

The one or more linear encoders 122 can be optical linear encoders, mechanical linear encoders, magnetic linear encoders, inductive linear encoders, capacitive linear encoders, or a combination thereof. The linear encoders 122 can be absolute encoders, incremental encoders, or a combination thereof. The one or more linear encoders 122 can track or encode the longitudinal movement/translation or displacement of the imaging device 102 and/or inner member 105. For example, the one or more linear encoders 122 can track or encode the longitudinal movement/translation or displacement of the proximal segments of the inner member 105.

In these and other embodiments, the position unit 120 can also include one or more rotary encoders 124. The one or more rotary encoders 124 can be absolute rotary encoders, incremental rotary encoders, or a combination thereof. The one or more rotary encoders 124 can be optical rotary encoders, mechanical rotary encoders, magnetic rotary encoders, capacitive rotary encoders, or a combination thereof. The one or more rotary encoders 124 can track or encode the rotation or angular position of the imaging device 102 and/or inner member 105.

The position unit 120 can also include a motor and drive assembly 126. The motor and drive assembly 126 can be configured to translate the imaging device 102, the inner member 105, or a combination thereof in a longitudinal direction (e.g., in a distal direction, a proximal direction, or a combination thereof). For example, the motor and drive assembly 126 can provide torque or rotate a proximal segment of the inner member 108 while the outer shaft 108 may remain fixed. This may rotate the optical component 106 and scan the transmitted light Tx around the distal tip 104. The rotation of the inner member 108 relative to the outer shaft 108 may also allow a tapered distal end of the optical component 106 to cut or otherwise 'de-bulk' tissue in order to remove and/or cross occlusions or partial occlusions such as the partial occlusion 109.

While the imaging device 102 is generally described in terms of imaging and an intervention such as crossing, it should be understood that these operations may only be a portion of the imaging device's 102 functionality. For example, the inner member 105 and outer shaft 108 may extend along one lumen of the imaging device 102, while other lumens are used for other tools or functions. For example, the imaging device 102 can also be used to deliver or otherwise introduce fluids, pharmaceutical compositions including small molecules and biologics, contrast media, biomarkers, or a combination thereof to the distal tip 104, a target treatment site in proximity to the distal tip 104 (e.g., a target vessel site within the patient's body), or a combination thereof.

The control unit 110 may be coupled to a computing device 130. In some embodiments, the computing device 130 may be a separate component from the control unit 110. In some embodiments, the control unit 110 may be integral with the computing device 130. In some embodiments, the control unit 110 can be configured as a handle or handheld unit. In other embodiments, the control unit 110 can be configured as a control box or tabletop unit. In some embodiments, the computing device 130 can be a desktop computer, a laptop computer, a tablet device, or a combination thereof. The computing device 130 can comprise a processor 132, such as a central processing unit (CPU) and a memory 134. The processor 132 may have a 32-bit processor data bus or a 64-bit processor data bus. The processor 132 can be a dual core, quad core, or other multi-core processors. The processor 132 can operate at speeds of 3 GHz or more. The memory 134 can comprise random access memory (RAM) and read-only memory (ROM). More specifically, the memory units can comprise dynamic RAM (DRAM), static RAM (SRAM), sync DRAM (SDRAM), double data rate (DDR) SDRAM, double data rate 2 (DDR2) SDRAM, or a combination thereof. An optional GPU may consist of 8 GB or more memory for the implementation of a neural network for analyzing images realtime in order to enhance their visualization with machine or deep learning, resulting in more visually intuitive images for instance with warnings, notations, and augmented reality.

The computing device 130 can process and store images captured by the optical unit 112. The optical unit 112 and the computing device 130 can be combined with other devices to make up part of an OCT imaging system. For example, the OCT imaging system can be a common-path OCT system, a time domain OCT system, a spectral ore frequency domain OCT system, or a combination thereof. The computing device 130 can be coupled to a detector 118. The computing device 130 may receive a signal, such as a raw data, from the detector 118 and record a sequence of raw data over time in the memory 134. The processor 132 may perform one or more image processing steps to extract an image from the raw data.

The processor 132 may work together with the control unit 110 to image the walls of vessel that the distal tip 104 is located in. For example, the position unit 120 may rotate the inner member 105, which in turn may 'scan' the field of view of the optical unit around the walls of the vessel as the optical component 106 is rotated. The raw data generated by the detector 118 may be associated with a particular angular position of the inner member 105 relative to the outer shaft 108 (e.g., as reported by the rotational encoder 124). The processor 132 may use the angular information and the raw data to reconstruct an angular view of the vessel walls which is larger than a single field of view of the detector 118. In some embodiments the processor 132 may generate a 360 degree view of the vessel wall. In a similar fashion, the processor 132 may also work with the position unit 120 to build an image which extends along a longitudinal axis which is larger than a single field of view by moving the inner member 105 in a proximal/distal direction while imaging.

In some embodiments, the images generated by the processor 132 may be displayed by a user of the system 100 (e.g., displayed on a screen). In some embodiments, the processor 132 may generate a display images at a rate (e.g., a video rate) which allows for "real-time" imaging of the vessel walls. In some embodiments, the use of the tapered distal end may be based on the images generated.

The computing device 130 can also be configured to perform image registration on images captured by the optical unit 112. For example, image registration can involve establishing correspondence between features in sets of images and using one or more transformation models to infer correspondence of additional features away from such features. Imaging registration can also be referred to as image alignment. Image registration can also be done to align or map images obtained from different imaging modalities (e.g., OCT with intravascular ultrasound (IVUS) or OCT with X-ray fluoroscopy).

Figure 2:
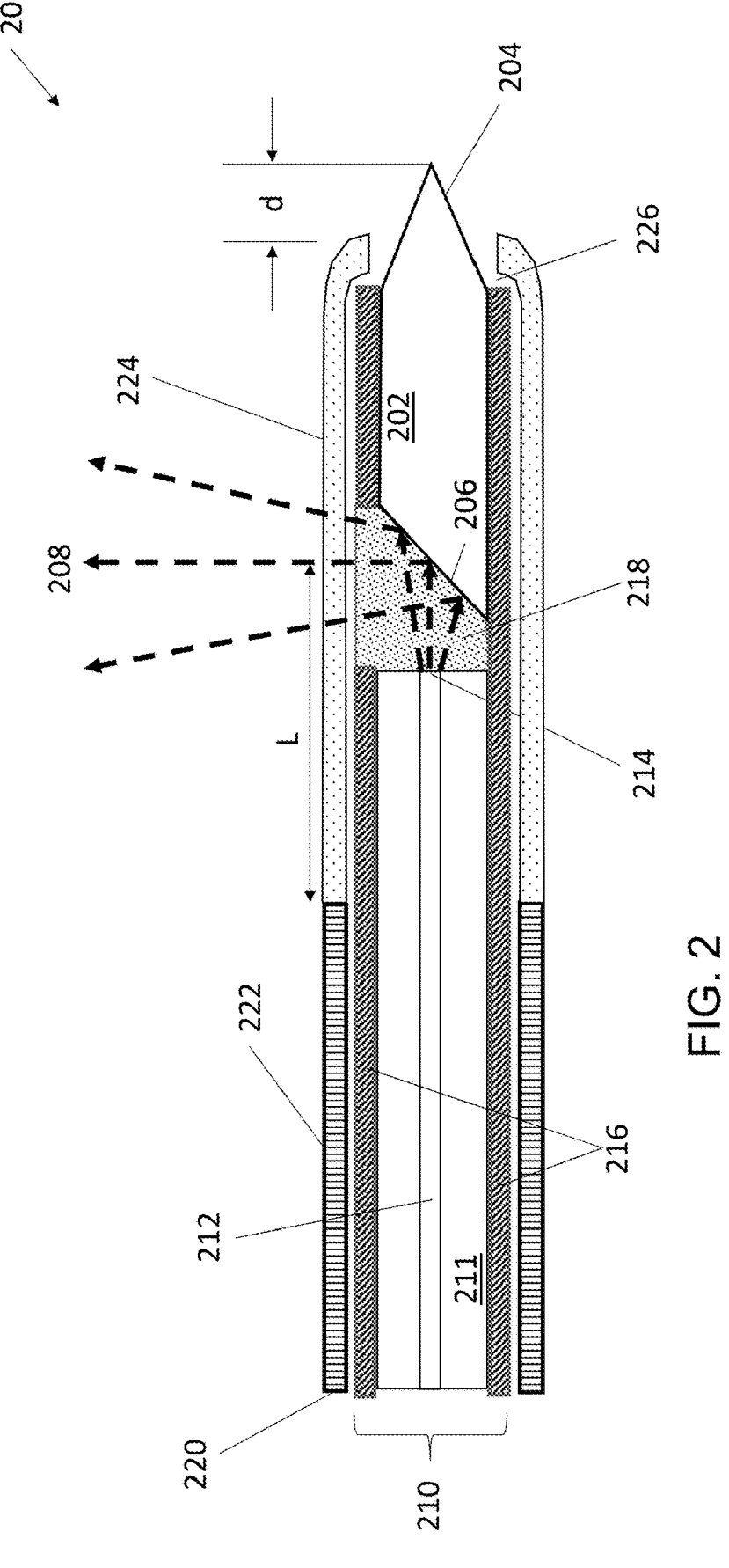
FIG. 2 is a cross-sectional diagram of a distal end of an imaging crosser device according to some embodiments of the present disclosure.

FIG. 2 is a cross-sectional diagram of a distal end of an imaging device according to some embodiments of the present disclosure. The imaging device 200 may represent a distal end of an imaging device which may be used as part of an imaging and intervention system such as the imaging and intervention system 100 of FIG. 1.

The imaging device 200 includes an outer shaft 220, and an inner element 210. The inner element 210 may rotate relative to the outer shaft 220, and may be used for both imaging and interventions. The inner element 210 includes an optical element 202 which includes a tapered distal end 204 and a reflecting surface 206. The reflecting surface 206 may be configured to redirect light between one or more optical fibers 212 of the inner element 210 and an imaging target (e.g., a field of view). As shown in the example of FIG. 2, the reflecting surface 206 is redirecting light received from the optical fiber 212 (e.g., transmitted light Tx of FIG. 1) into an imaging beam 208 which extends out of a periphery of the imaging device 200. The reflecting surface 206 may also redirect received light (e.g., Rx of FIG. 1) back into the optical fiber 212. The tapered distal end 204 may include one or more tissue contact surfaces (here a conical tissue contact surface) which can be extended up to a distance 'd' from a front surface of the outer shaft 220.

The outer shaft 220 may be an outer body of the imaging device 200. The outer shaft 220 may have an outer diameter of around 0.020 inches (0.508 mm) or less. In another embodiment, the outer shaft 220 may have an outer diameter of around 0.045 inches (1.143 mm) or less. The outer shaft 220 may be roughly the size of a guidewire. The outer shaft 220 may be fixed (e.g., to a control or optical unit) relative to the inner element 210. Accordingly, the outer shaft 220 may be a torque shaft which may remain fixed while the inner element 210 rotates within the outer shaft 220.

The outer shaft 220 may have a body 222 and a cap 224. The cap 224 may be located at a distal end of the outer shaft 220. The cap 224 may allow light to pass from an outside of the outer shaft 220 to a lumen of the outer shaft 220 (e.g., may allow light to pass from outside the outer shaft 220 to the inner element 210). In some embodiments, the cap 224 may be a separate component attached to an end of the body 222. In some embodiments, the cap 224 may be integral to the body 222, and the cap 224 may refer to a distal end of the body 222. The body 222 may be formed from a coil or modified hypotube. The body 222 and cap 224 may both be generally tubular members, with a lumen which the inner element 210 is disposed within. The body 222 and cap 224 may, in some embodiments, have similar outer diameters and thicknesses. In some embodiments, the body 222 and cap 224 may have different outer diameters and/or thicknesses from each other.

In some embodiments, the cap 224 may be an optically transparent material. For example, the cap 224 may be made from a different material than the body 222 of the outer shaft 220. In some embodiments, the cap 224 may include a window, for example such as a laser cut window through the material of the cap 224. In some embodiments, the laser cut window may include a cover made from an optically transparent material. In some embodiments, the window may be uncovered. In some embodiments, the body 222 of the outer shaft 220 may be made from an optically transparent material, and a separate cap 224 may be unnecessary.

In some embodiments, the cap 224 may include a hard stop 226, which limits the motion of the inner member 210 relative to the outer body 220. The hard stop 226 may limit the longitudinal motion of the inner member 210 relative to the outer body 220 (e.g., the motion along a long axis of the imaging device 200). For example, an inner diameter of the cap 224 at the hard stop 226 may be less than an outer diameter of the inner member 210. In some embodiments, the hard stop 226 may be a tapered section of the cap 224 and/or a step on the inner wall of the cap 224.

The inner member 210 may be a generally cylindrical member which is disposed in a lumen of the outer shaft 222. The inner member 210 may have an outer diameter of around 0.010 inches (0.254 mm) or less. In another embodiment, the outer shaft 210 may have an outer diameter of around 0.018 inches (0.457 mm) or less. The inner member 210 may be movable relative to the fixed outer shaft 220. The inner member 210 may be extendable/retractable relative to the outer shaft 220 along a longitudinal axis of the imaging device 200 and may be rotatable relative to the outer shaft 220. For example, a motor/drive assembly (e.g., 126 of FIG. 1) may move the inner member 210 relative to the outer shaft 220.

The inner member 210 includes an optical fiber 212. The optical fiber 212 may transmit light between an optical unit (e.g., 112 of FIG. 1) coupled to a proximal end of the imaging device 200 and the distal end of the imaging device 200. The optical fiber 212 may be a single fiber or a multi-core fiber. The optical fiber 212 may be surrounded by a cladding material 211, which may support the optical fiber 212 and provide optical conditions (e.g., an index mismatch) which enables the transmission of light along the optical fiber 212. The cladding material 211 may in turn be surrounded by a fiber reinforcement 216. The fiber reinforcement 216 may support the optical fiber 212 and cladding material 211. In some embodiments, the fiber reinforcement 216 may be a coil or a modified hypotube. A portion of the optical component 202 may extend beyond a distal end of the fiber reinforcement.

The optical fiber 212 (and cladding material 211) may terminate at a reference surface 214. The reference surface 214 may be at a distal end of the optical fiber. In some embodiments, the reference surface 214 may generally be a flat surface (e.g., a cut in the fiber) which is at a right angle to the long axis of the imaging device 200. The reference surface 214 may reflect a portion of the transmitted light along the optical fiber 212. The light reflected from the reference surface 214 may be a local oscillator (LO) portion of the light, which may be interferometrically combined with received light in an optical unit (e.g., optical unit 112 of FIG. 1).

The inner member 210 includes an optical component 202. The optical component 202 may be a single element which includes a reflecting surface 206 and a tapered distal end 204. The optical component 202 may be single piece of material which has a one or more surfaces shaped to form the reflecting surface 206 and one or more surfaces shaped to form the tapered distal end 204. In the example embodiment of the optical component 202, the reflecting surface 206 and tapered distal end 204 may be separate surfaces of the optical component 202.

The optical component 202 may be a generally cylindrical element, a portion of which may be disposed in the fiber reinforcement 216. The optical component 202 may be formed from a single material. For example, the optical component 202 may be formed of aluminum oxide, zirconium oxide, silicon carbide, diamond, or combinations thereof. In some embodiments, the optical component 202 may be a metal, such as SS304.

The tapered distal end 204 may be a tool for coronary interventions, such as a crossing tool. The tapered distal end 204 may be a tissue contact surface which extends a distance d from a distal tip of the outer shaft 220 when the inner member 210 is extended to the hard stop 226. In some embodiments the distance d may be about 1 mm or less. The tapered distal end 204 may be formed along the distal end of the optical component 202. For example, the tapered distal end 204 may be a conical surface extending to a point. In some embodiments, the point of the tissue contact surface may be along a long axis of the imaging device 200. In some embodiments, the point of the conical surface may be offset from the long axis of the imaging device 200.

The reflecting surface 206 of the optical component 202 may be reflective surface which redirects light from an optical axis generally aligned with the long axis of the fiber, and an optical axis directed to a side of the imaging device 200. For example, the reflecting surface 206 may redirect light at about a right angle. The reflecting surface 206 may be a slanted surface at a proximal end of the optical component 202. The angle of the optical 206 with respect to a long axis of the imaging device 200 may be chosen based on the desired deflection of light which reflects from the reflecting surface 206. For example, in some embodiments, the reflecting surface 206 may have an angle of about 45 degrees. In some embodiments, the reflecting surface 206 may be coated with a reflective material. For example, the reflective surface of the reflecting surface 206 (e.g., the proximal surface of the optical component 202) may be gold coated.

As shown by the example rays of the imaging beam 208, transmitted light through the optical fiber 212 may diverge as it leaves the optical fiber 212 at the reference surface 214. The divergent rays of the imaging beam 208 may then be redirected by the reflecting surface 206 such that the imaging beam 208 forms a divergent cone of transmitted light which extends out a side of the imaging device 200. The fiber reinforcement 216 may include a window (and/or be made of a transparent material) to allow the imaging beam 208 to pass out of the inner member 210 (and from there out of the imaging device 200).

Accordingly, as the inner member 210 rotates relative to the outer shaft 220, the imaging beam 208 may be swept around the perimeter of the imaging device 200. The inner member 210 may also be movable along a longitudinal axis of the imaging device 200 relative to the outer shaft 220. The field of view represented by the imaging beams 208 may be swept around the imaging device 200 in a 360 degree arc, and may be moved longitudinally relative to a position of the imaging device along an imaging range L. The imaging range may be defined by a furthest extension of the inner member 210 within the outer shaft 220 (e.g., when the inner member 210 abuts the hard stop 226) and by a length of the transparent portion of the outer shaft 220 (e.g., the transparent portion of the cap 224). In some embodiments the imaging range L may be about 5-25 mm.

The imaging beam 208 may interact with the environment surrounding the imaging device 200. For example, when the imaging device 200 is in a blood vessel, the imaging beam may illuminate a portion of the blood vessel wall around the imaging device 200. As the inner member 210 rotates, the imaging beam 208 may be swept around to illuminate a strip of the vessel wall. Light may be returned from the illuminated tissue to the imaging device 200. For example, a portion of the illumination light may be scattered and/or reflected by one or more components and structures of the tissue. Some of the illumination light may penetrate a distance into the tissue before being returned to the imaging device 200. A portion of the returned light may follow an optical path which reflects off the imaging tool 206 and is coupled into the optical fiber 212. The returned light which is coupled into the fiber may form the received light (e.g., received light Rx of FIG. 1).

The inner member 210 may include a filler material 218 between a distal end of the optical fiber 212 (e.g., the reference surface 214) and a proximal surface of the optical component 202 (e.g., the reflecting surface 206). Since the reference surface 214 and reflecting surface 206 may be at different angles with respect to a long axis of the imaging device 200, there may be a gap between the reference surface 214 and the optical component 202. The filler material 218 may an optically transparent material to allow the imaging beam 208 (and received light) to pass through the filler material 218. In some embodiments, the filler material 218 may have an index of refraction chosen to match an index of refraction of the optical fiber 212 to prevent refraction of the light at the optical fiber/filler interface. For example, the filler material may have an index of refraction of about 1.55. In other examples, the filler material may have an index of refraction in the range of 1.40 to 1.80, 1.50 to 1.60, or 1.55 to 1.65. In some embodiments, the filler material 218 may be an adhesive, and may help couple the optical component 202 to the optical fiber 212 and cladding 211. In some embodiments, the filler material 218 may also fill a window in the fiber reinforcement 216.

Figure 3:
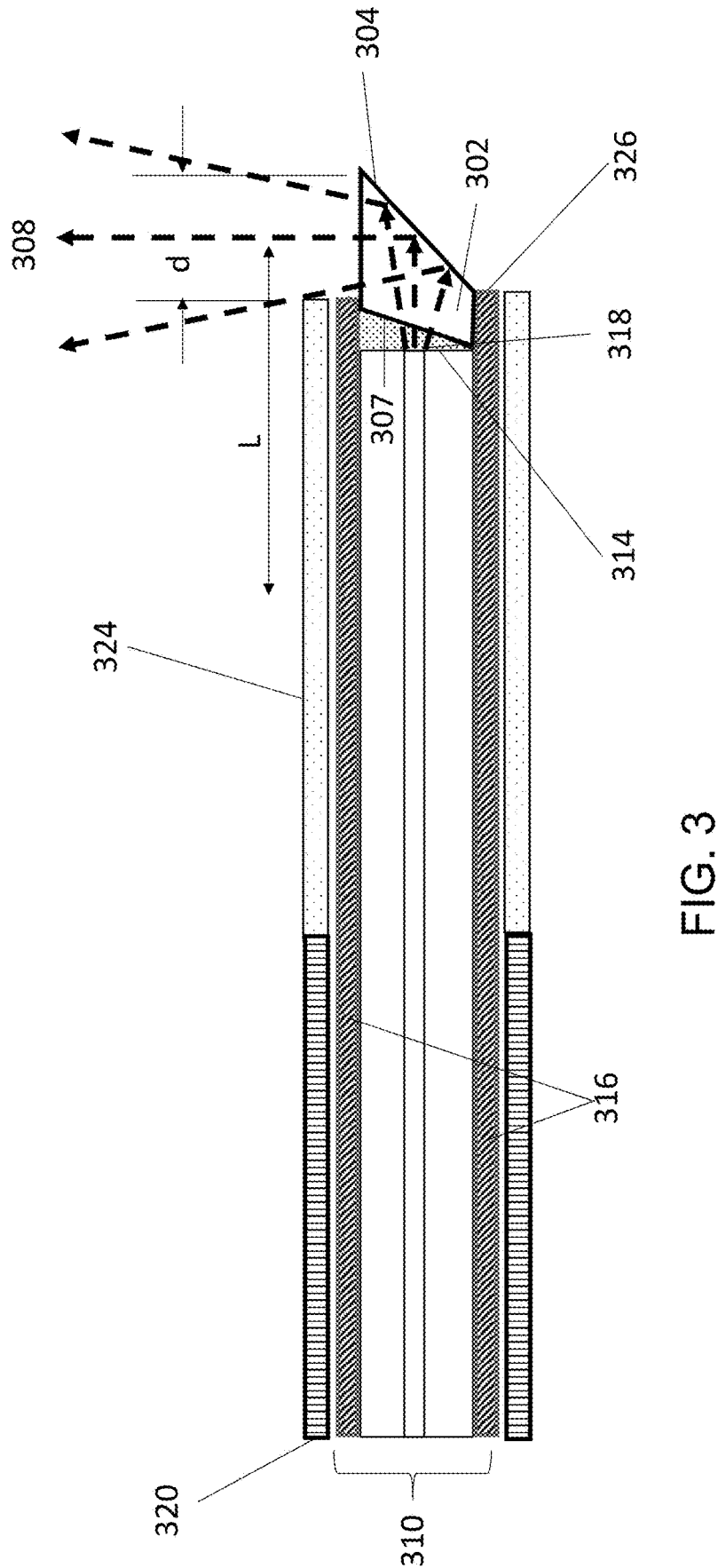
FIG. 3 is a cross-sectional diagram of a distal end of another embodiment of exemplary imaging crosser device.

FIG. 3 is a cross-sectional diagram of a distal end of an imaging device according to some embodiments of the present disclosure. The imaging device 300 may represent a distal end of an imaging device which may be used as part of an imaging and intervention system such as the imaging and intervention system 100 of FIG. 1. The imaging device 300 may include many similar features to the imaging device 200 of FIG. 2. For the sake of brevity, features and operations previously described with respect to the imaging device 200 will not be repeated with respect to the imaging device 300 of FIG. 3.

The imaging device 300 includes an optical component 302 which includes a single distal surface 304 which acts as both the reflecting surface and tapered distal end. The optical component 302 may be generally cylindrical, with a generally trapezoidal longitudinal cross section. The optical component 302 may be formed from an optically transparent material (e.g., sapphire), and light may pass through a proximal surface 307 of the optical component 302 and into the material of the optical component 302. The proximal surface 307 may be angled (relative to the long axis of the imaging device 300) to minimize the reflection of light as it passes from the filler material 318 into the material of the optical component 302.

The distal surface 304 of the optical component 302 may extend a distance d from a distal tip of the outer shaft 320. The distal surface 304 may be a generally flat surface at an angle relative to a long axis of the imaging device 300. The distal surface 304 may come to a point a distance d beyond the outer shaft 320 which may act as a crossing tool. Light from the optical fiber 312 may reflect from the distal surface 304 within the optical component 302. In some embodiments, the distal surface 304 may be angled to set up a total internal reflection (TIR) condition at the distal surface 304. In some embodiments, the distal surface 304 may be coated with a reflective material (e.g., gold). Accordingly, the optical component 302 has a single surface (e.g., distal surface 304) which acts as both a tapered distal end and a reflecting surface.

Figure 4:
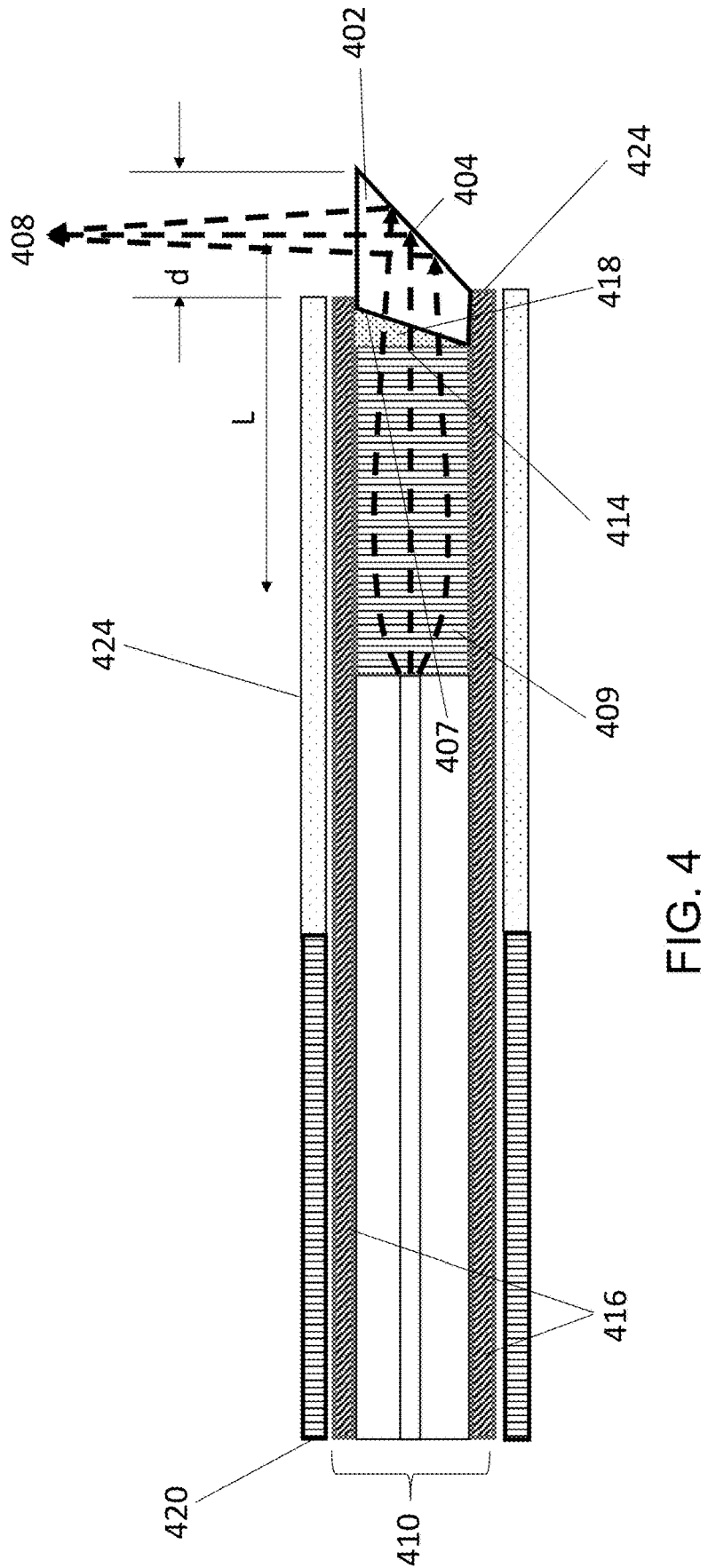
FIG. 4 is a cross-sectional diagram of a distal end of another embodiment of an imaging crosser device.

FIG. 4 is a cross-sectional diagram of a distal end of an imaging device according to some embodiments of the present disclosure. The imaging device 400 may represent a distal end of an imaging device which may be used as part of an imaging and intervention system such as the imaging and intervention system 100 of FIG. 1. The imaging device 400 may include many similar features to the imaging device 200 of FIG. 2 and the imaging device 300 of FIG. 3. For the sake of brevity, features and operations previously described with respect to the imaging device 200 and/or the imaging device 300 of FIG. 3 will not be repeated with respect to the imaging device 400 of FIG. 4.

Similar to the optical component 302 of FIG. 3, the optical component 402 includes a distal surface 404 which is both a tapered distal end and reflecting surface. The imaging device 400 also includes a lens 409 disposed between a reference surface 414 of the optical fiber 412 and a proximal surface 407 of the optical component 402. The lens 409 may shape the imaging beam 408. For example, the lens 409 may focus the imaging beam 408 so that the imaging beam 408 focuses at a focal point. The focal length of the lens 409 may be chosen to focus the imaging beam 408 at focal region at or within a wall of the vessel (e.g., based on an expected distance from the imaging device 400 to the vessel wall). In some embodiments, the lens 409 may be a gradient-index (GRIN) lens. In the imaging device 400, the reference surface 414 may be at a distal end of the lens 409.

In this and in other variations of the exemplary embodiments described herein, the lens 409 may be but not limited to a Fresnel lens, spherical lens, aspheric lens, or an anamorphic lens. The lens may also be selected to either focus light at a selected distance from the exterior exit surface of the imaging beam, as depicted in FIGS. 22E and 22F, or may be selected to provide a collimated beam profile, as depicted in FIGS. 22C and 22D, or may be selected to produce varying degrees of focusing power including collimation at different angular orientation across the beam. The lens 409 may also comprise a lens assembly with two or more lenses. Additional features regarding lenses in the OCT imaging system are provided later below.

Figures 5A, 5B:
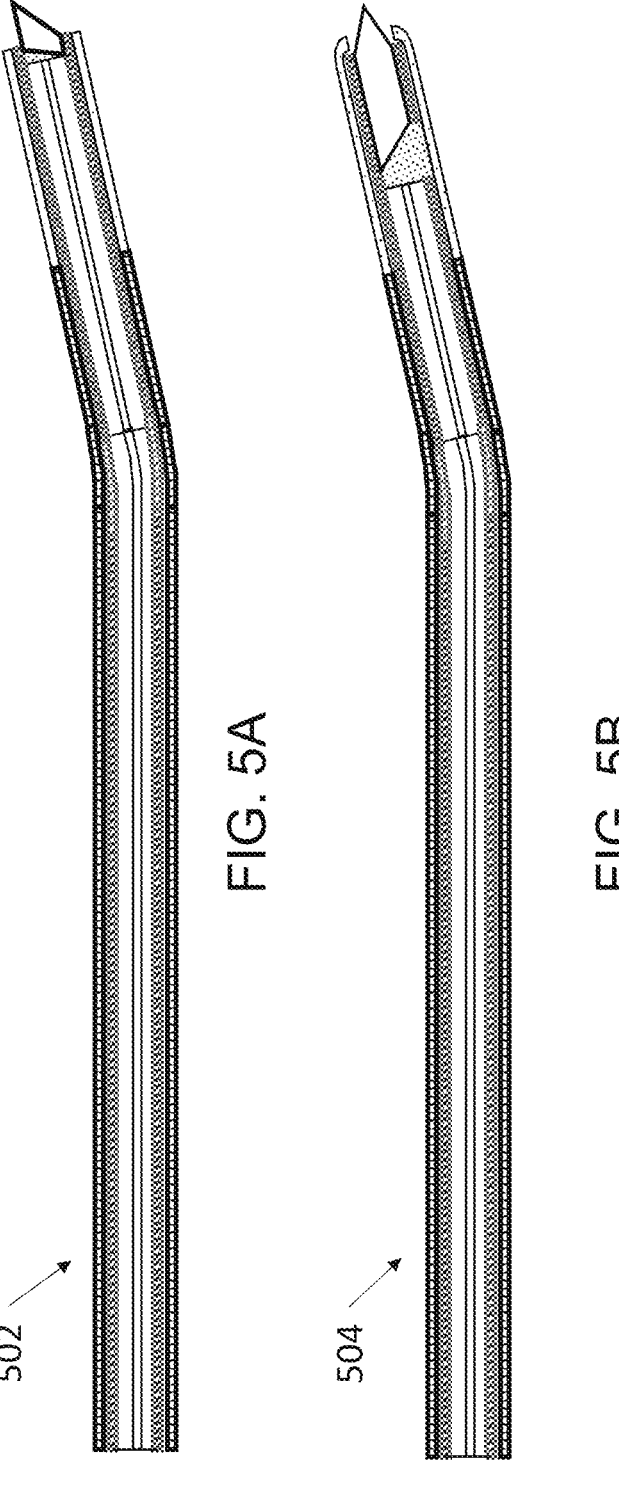
FIGS. 5A and 5B are schematic diagram of exemplary imaging crosser devices with angled tips.

FIGS. 5A and 5B are schematic diagrams of an exemplary imaging device with a bend or angle region according to some embodiments of the present disclosure. FIGS. 5A and 5B depict of imaging devices 502 and 504, each which includes a pre-shaped bend which may aid in directional crossing with the tapered distal end. The imaging device 502 may be an imaging device, such as the imaging devices 300 of FIG. 3 and 400 of FIG. 4 where the optical component has a single surface which acts as both the tapered distal end and the reflecting surface. The imaging device 504 may be an imaging device, such as the imaging device 200 of FIG. 2, where the optical component has a first surface which acts as the reflecting surface and a second surface which acts as a tapered distal end.

Figure 6A:
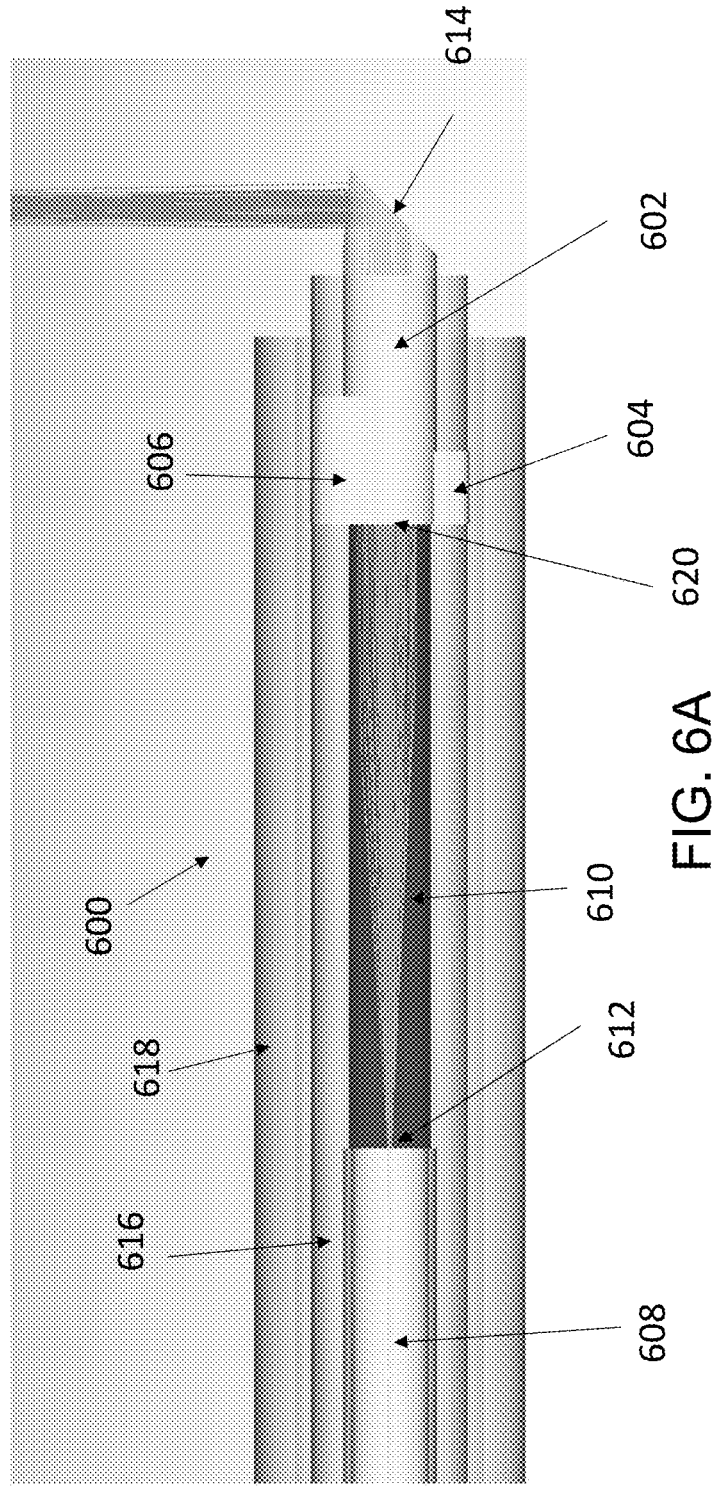
FIGS. 6A and 6B are schematic cross-sectional and perspective views of another exemplary imaging crosser device.
Figure 6B:
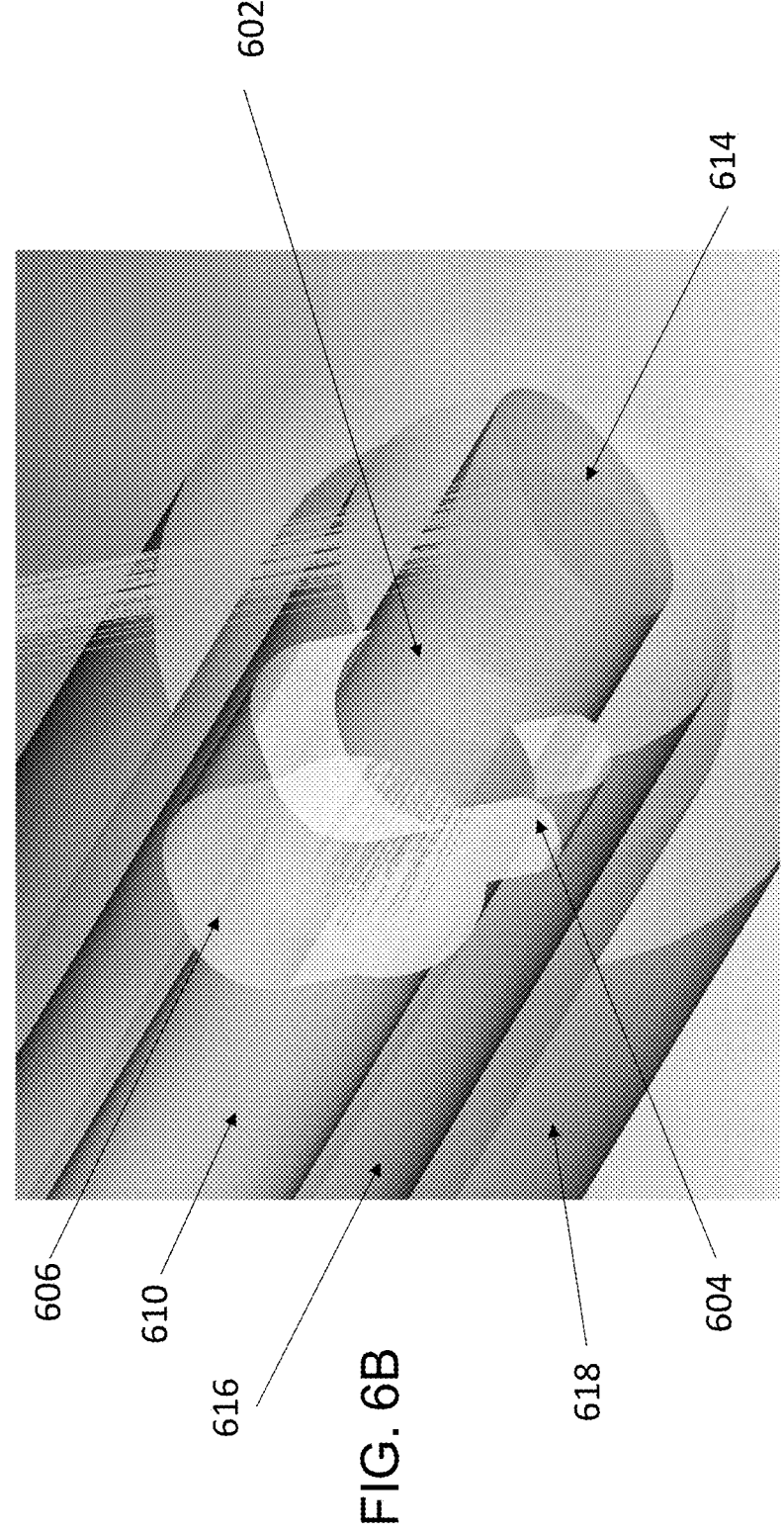

FIGS. 6A and 6B are schematic diagrams of another embodiment of an imaging crosser device 600, comprises a shaped or molded optical element 602. The molded optical element 602 may comprise one or more structures 604 and 606 that are configured to facilitate handling, manipulation, and/or alignment of the optical element 602 during manufacturing and/or during usage. The device 600 may further comprise optical fiber 608 to transmit light between a proximal light source or light receiver and the optical element 602. The optical fiber 608 may be single-mode fiber or multi-modal fiber. A lens 610 may be provided to optically couple the fiber 608 and the optical element 602. The lens 610, for example, may be a gradient-index lens that is fused at its proximal end 612 to the distal end of the fiber 608, and is configured to collimate or focus light from the light source and fiber 608 to the reflecting surface 614 of the optical element 602. The fiber 608, lens 610 and optical element 602 may be housed in a hypotube 616 of the device 600. The device 600 may be used in conjunction with a catheter 618. In the particular example depicted in FIGS. 6A and 6B, the hypotube 616 has an outer diameter of 0.010" or 0.017" or 0.022", but in other examples the hypotube have an outer diameter in the range of 0.009" to 0.022" or 0.012" to 0.020". The catheter 618 may comprise an inner diameter in the range 0.010" to 0.013", or 0.018" to 0.020" or 0.020" to 0.024" or otherwise configured with a diameter to receive the hypotube 616 of the device 600. The outer diameter of the catheter 618 may be in the range of 0.016" to 0.020", or 0.016" to 0.017" or 0.018" to 0.045". The inner and/or outer surfaces of the hypotube 616 and catheter 618 may comprise a lubricious coating to facilitate rotational or longitudinal movement of the device 600 or catheter 618.

Referring still to FIGS. 6A and 6B, the optical element 602 comprises first and second protruding flanges or structures 604 and 606. The protruding structure 604 and 606 may be used to grasp and manipulate the optical element 602 while reducing the risk of damage to the optical properties of the optical element 602, and/or may be used to facilitate alignment In this particular example, structure 604 comprises a smaller cross-sectional shape than structure 606, with a transverse width and/or longitudinal length that is smaller than the transverse width or dimension of the other structure 606. In some examples, however, the structures 604 and 606 may be located at and proximally aligned and contiguous with the proximal end 620 of the optical element 602. These structures 604 and 606 may be sized and shaped to facilitate insertion and/or alignment of the optical element 602 with the hypotube 616. Referring to FIGS. 8A to 8D, the hypotube 616 comprises an inner lumen 622 to receive the fiber 608 and the optical element 602, as well as a proximal opening (not shown), and distal opening 623 from which the optical element 602 can partially protrude. The hypotube 616 further comprises an insertion opening 626 through which the optical element 602 may be inserted into the inner lumen 622. The insertion opening 626 may be configured with a length sufficient to receive the optical element 602 such that the distal end of the optical element 602 can protrude from the distal opening 624 of the hypotube 616, and to have the structure 604 to be seated in an alignment recess opening 628 that is opposite the insertion opening 626. The alignment opening 628 and the protruding structure 604 may be configured to receive the protruding structure 604 or to form a complementary interfit between the opening 628 and structure 604. When the optical element 602 is fully seated in the hypotube 616, the distal surface 630 of the protruding structure 606 may abut the distal surface 632 of the insertion opening 626. The protruding structures 604 and 606 may further comprise cylindrically rounded side surfaces 634 and 636, which may align with the outer diameter of the hypotube 616 when the optical element 602 is fully seated. As depicted in FIG. 6A, the lens 610 may be pushed distally to abut and couple to the proximal surface of the optical element 602.

Figures 7A, 7B:
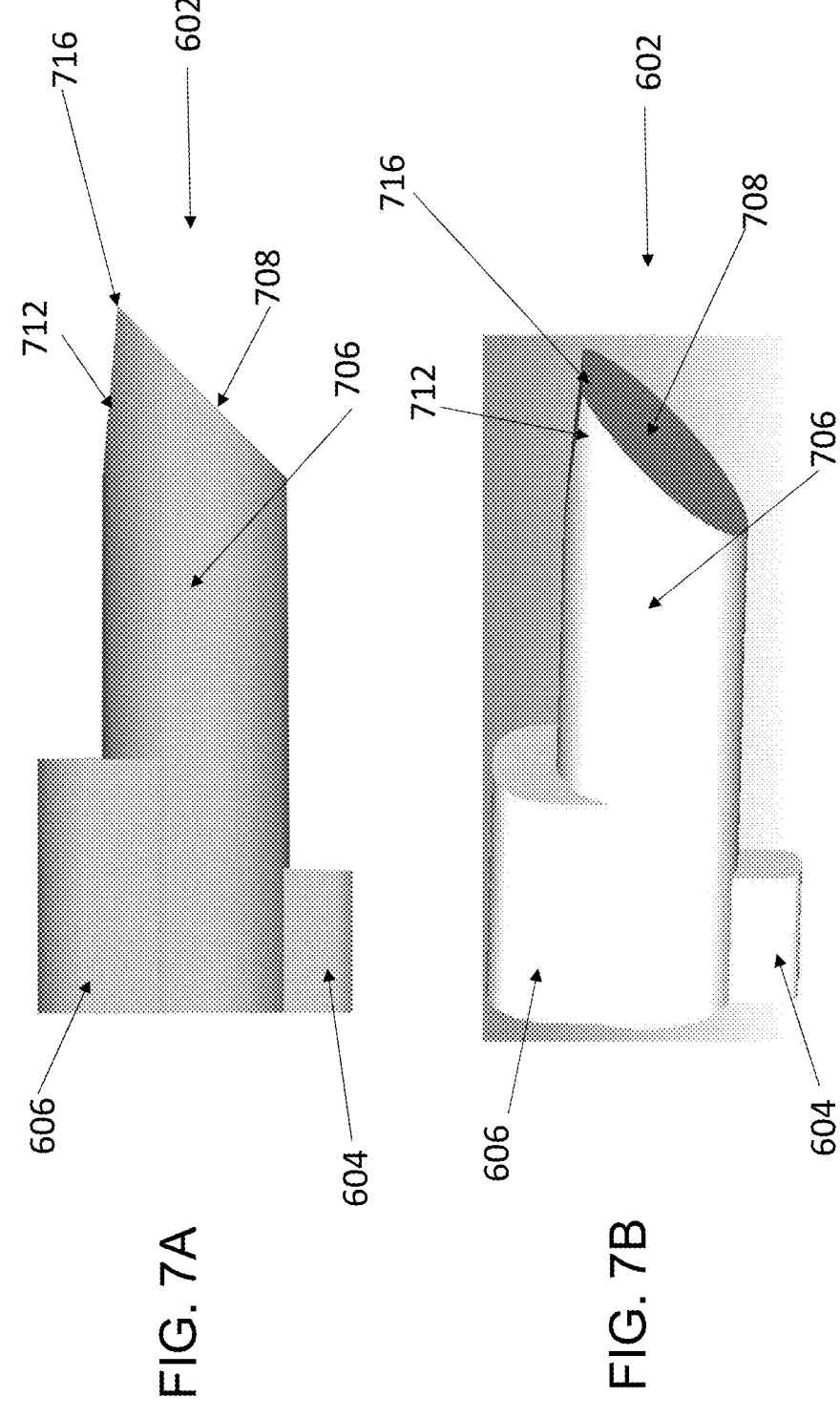
FIGS. 7A to 7E are side elevational, side perspective, rear perspective, front perspective and top perspective views, respectively, of the optical element in FIGS. 6A and 6B.
Figures 7C, 7D, 7E:
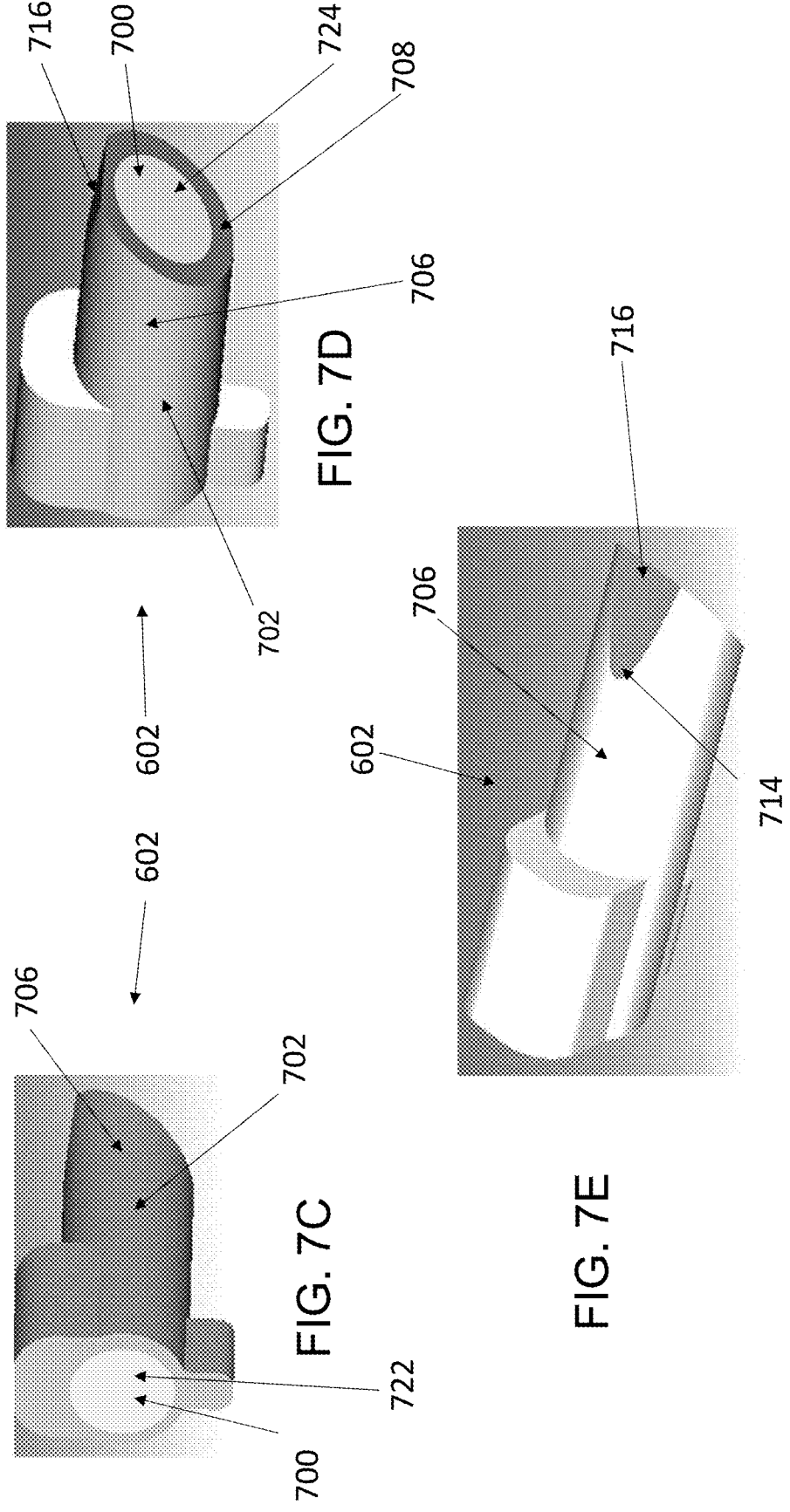
Figures 8A, 8B:
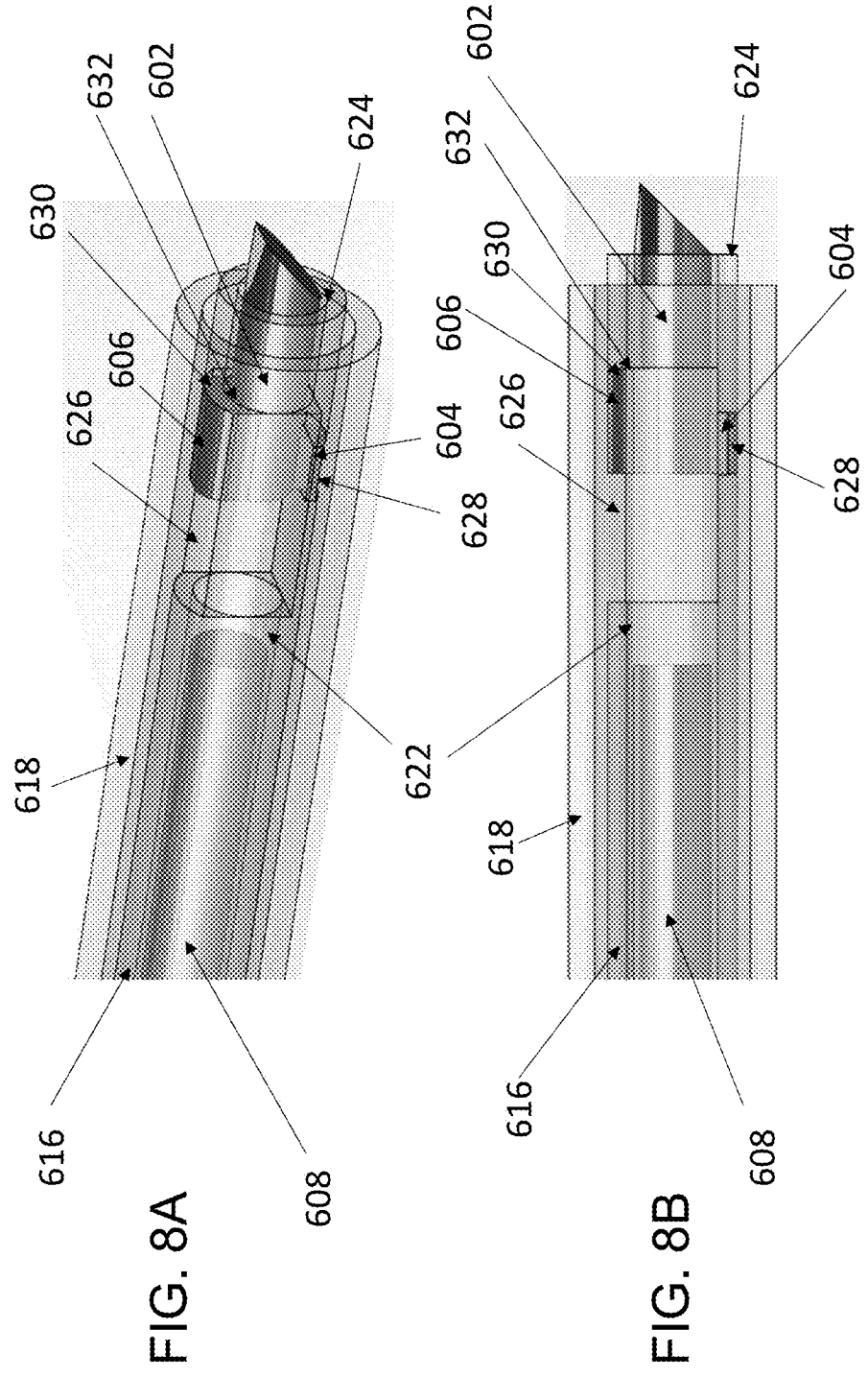
FIGS. 8A and 8B are schematic perspective and side views of the imaging crosser device in FIGS. 6A and 6B in a retracted position.
Figures 8C, 8D:
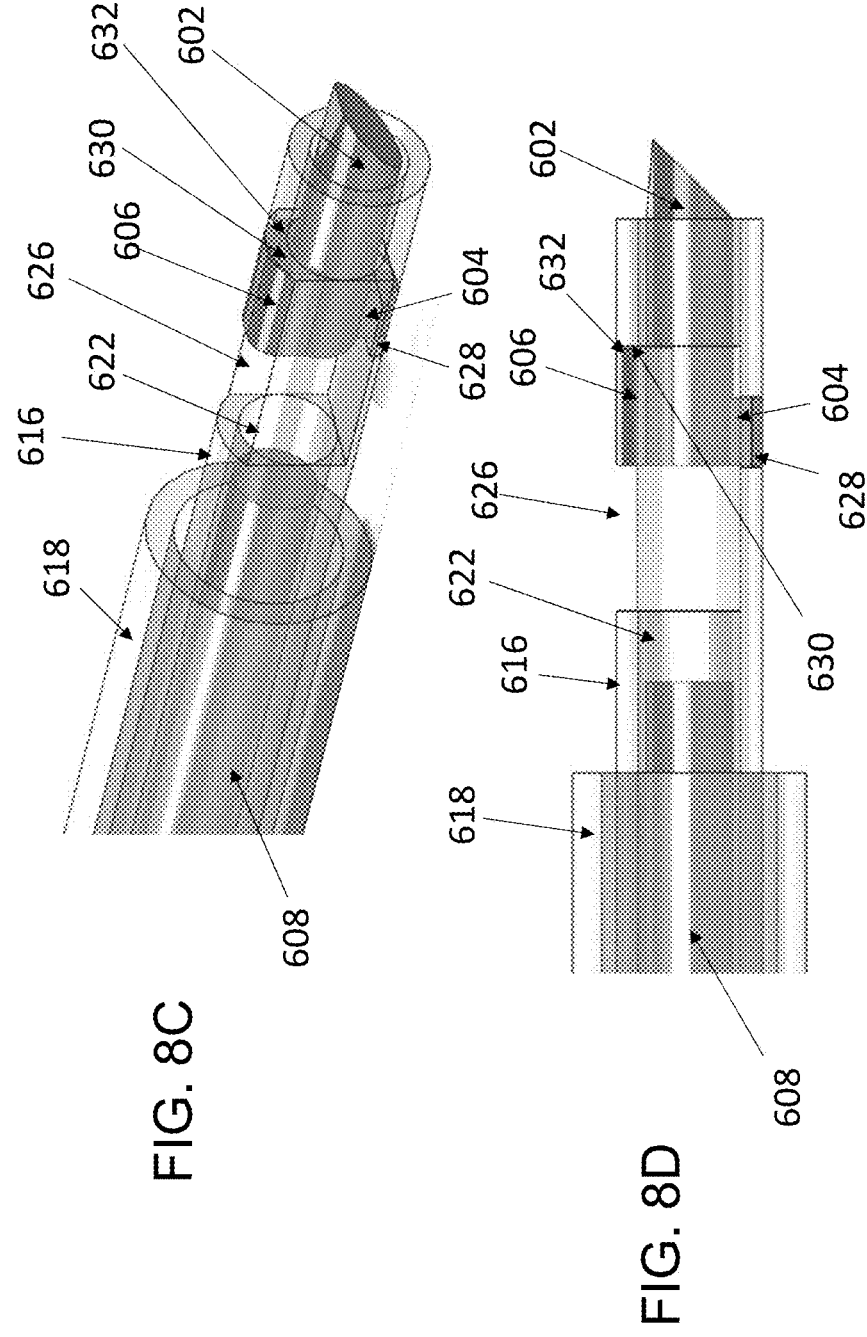
FIGS. 8C and 8D are schematic perspective and side views of the image crosser device in an extended position.

Referring now to FIGS. 7A to 7E, optical element 602 may an inner core 700 and an outer molded shell 702. The material for the inner core 700 may be high refractive index polymer such as but not limited to polyurethane, polyvinylpyrrolidone, polystyrene, polycarbonate, zeonex, or NAS-21, and the material for the outer molded shell 702 may be the same as that of the inner core 700 or optical polymer such as but not limited to polymethyl methacrylate (PMMA), optorez or cellulose. The inner core 700 may comprise a refractive index of around 1.55, but in other examples, may have an index in the range of 1.40 to 1.80, or 1.50 to 1.60, or 1.55 to 1.65. The length of the optical element may be approximately 500 microns, but in other examples may be in the range of 400 microns to 800 microns, or 500 microns to 600 microns, or 450 microns to 550 microns for example. The optical element 602 comprises a cylindrical body 706 that has a diameter that is about 150 microns, but in other embodiments may be in the range of 140 microns to 200 microns, or 140 microns to 160 microns. The distal end of the cylindrical body 706 may comprise a reflecting surface 708 that has a 45 degree orientation relative to the longitudinal optical axis 710 of the optical element 602. The cylindrical body 706 may further comprise a side interface surface 712 from which light reflected from the reflecting surface 708 exits the optical element 602, and from which light reflected back from the surrounding tissue structures are received. The side interface surface 712 may be formed or be oriented at a 5 degree to 8 degree angle inward from the outer diameter of the cylindrical body 706, and may have a maximum width of about 60 microns and a length of 135 microns. In other examples, the width may be in the range of 40 microns to 80 microns, and the length may be in the range of 100 microns to 180 microns. As depicted in FIG. 7E, the side interface surface 712 has a planar configuration with a parabolic shape, with an apex 714 that is proximal to a distal edge 716 that located at the proximal end of the optical element 602. The side interface surface 712 and reflecting surface 708 may share a common edge 720, as shown in FIG. 7D.

The inner core 702 may comprise a generally cylindrical shape with an orthogonal proximal surface 722 and an angled distal surface 724 that is aligned with the reflecting surface 708. In other examples, however, the core may comprise a flattened surface distally. The inner core 702 may have a diameter in the range of 100 to 150 microns, or 110 microns to 130 microns. In some variations, the inner core 702 may have a variable diameter or transverse shape. In FIGS. 7C and 7D, for example, the inner core 702 may have a diameter of about 110 microns at its proximal end, and a diameter of about 125 microns at its distal end.

The protruding structures 604 and 606 are located on opposite sides of the cylindrical body 706. The structures 604 and 606 may protrude the same or a different distance from the surface of the cylindrical body 706. In some variations, the total protruding distance may be about 100 microns, or in the range of 90 microns to 120 microns. Individually, each structure 604 and 606 may have a protruding distance in the range of 40 to 60 microns, or about 50 to 55 microns.

As depicted in FIG. 6A, light traveling through the fiber 608 is collimated or focused by the lens 610 onto the reflecting surface 708 of the optical element 602. The reflecting surface 708 is an interior surface of the optical element, opposite or complementary to an outer surface 726 of the tapered or angled distal end 728. In some variations, the outer surface 726 may further comprise a reflecting material, such as a gold or other metallic coating to facilitate reflections. To facilitate bonding of the coating, the surface may be mechanically or chemically treated to roughen the surface to enhance bonding.

Figure 9:
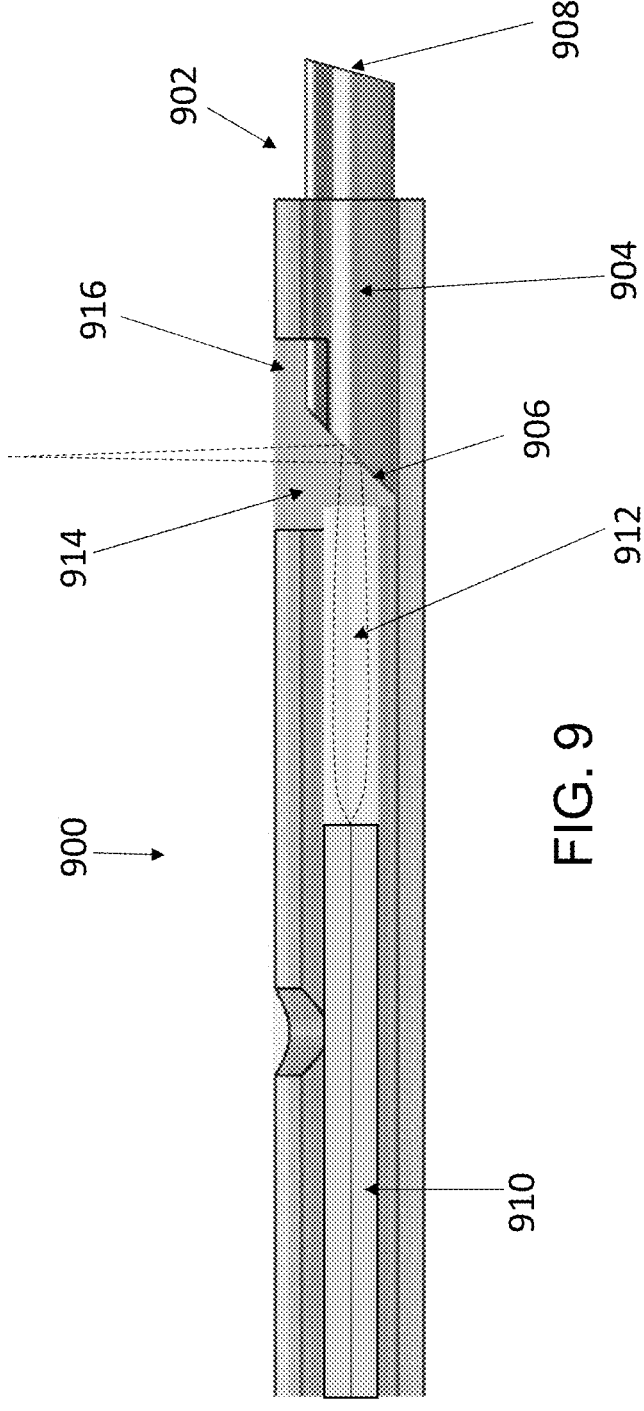
FIG. 9 is a schematic longitudinal cross-sectional view of another exemplary embodiment of an imaging crosser device.

In other examples, however, the reflecting surface of the optical element may comprise an outer reflecting surface. FIG. 9 depicts another example of an imaging crosser device 900, comprising an optical element 902 with a cylindrical body 904 with a length in range of 500 microns to 1000 microns, and a reflecting surface 906 located at the proximal end of the optical element 902 and is spaced apart from the tapered or angled penetrating distal end 908 of the optical element 900. In this embodiment, the device 900 also comprise a hypotube 908, fiber 910 and lens 912, but wherein the hypotube 908 comprise an imaging cavity 914 that is filled with an optically transparent polymer or adhesive 916. The lens 912 is configured to collimate or focus the light from the fiber 910 to the surrounding tissue at a different focal length, because of the closer location of the reflecting surface 906 in this device 900 compared to the more distal reflecting surface in device 600 of FIGS. 6A and 6B. The reflecting surface 906 may also be treated and/or coated with a reflecting material as described for the reflecting surface 708 of device 600. In embodiments comprising an outer reflecting surface, the material of the optical elements does not need to be optically transparent, and may comprise a metal such as steel, and may comprise a polished reflecting surface, or a material such a ceramic or glass, including sapphire or sapphire fiber.

Figure 18A:
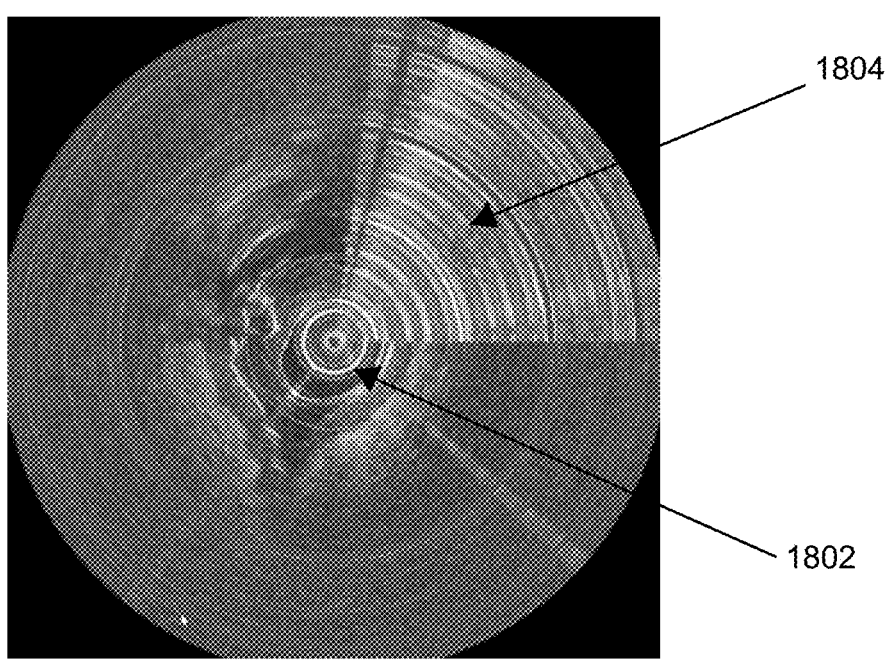
FIGS. 18A to 18C are OCT images depicting various types of artifacts that may result from refractive index mismatches between the imaging system and the surrounding fluid and tissue.
Figure 18B:
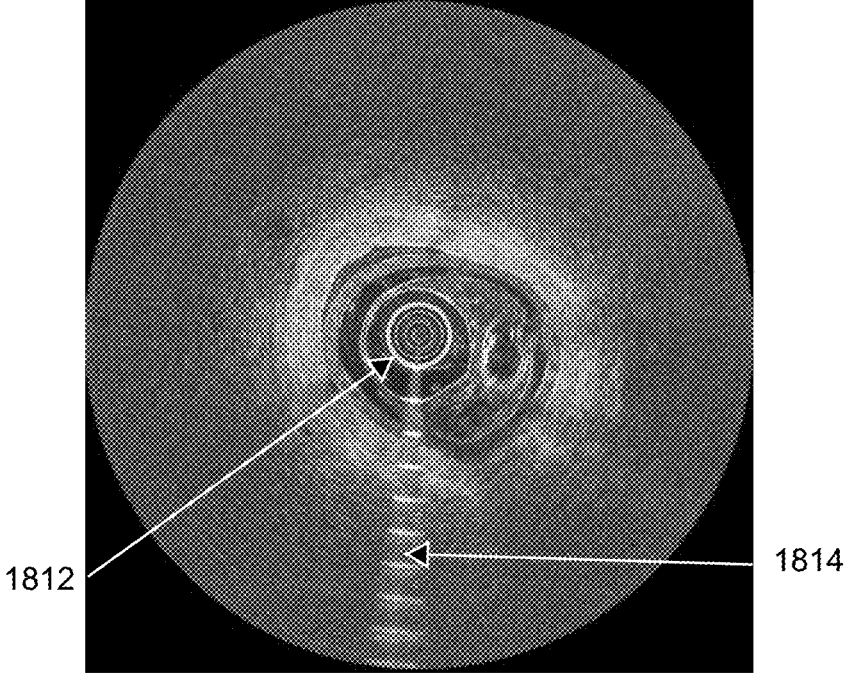
Figure 18C:
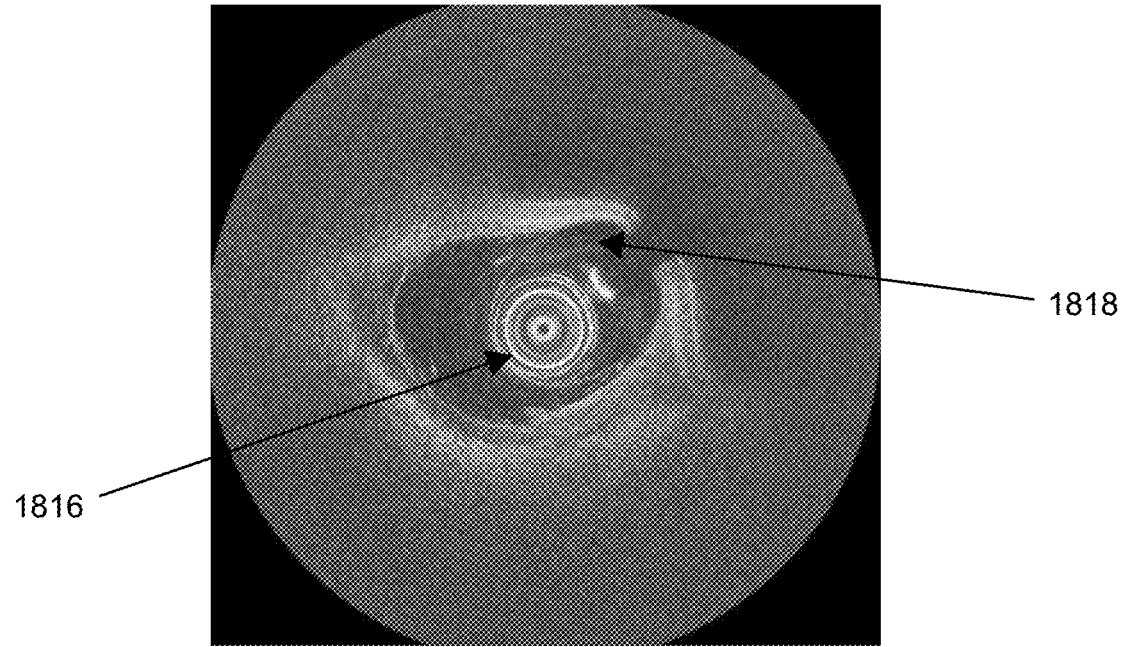
Figure 19A:
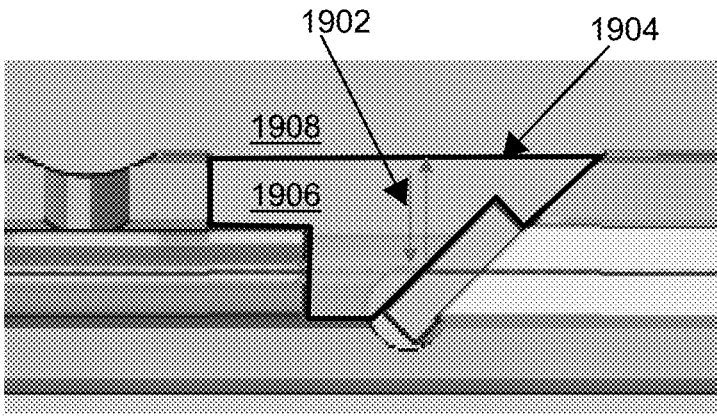
FIGS. 19A to 19C are schematic cross-sectional views of a side-viewing OCT imaging system, depicting back reflections from different optical filler configuration.
Figure 19B:
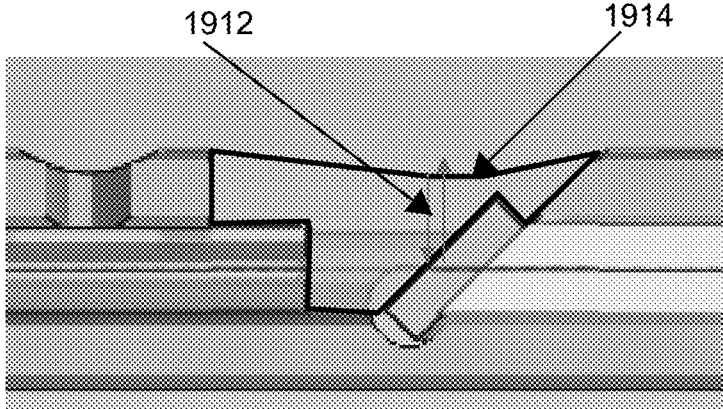
Figure 19C:
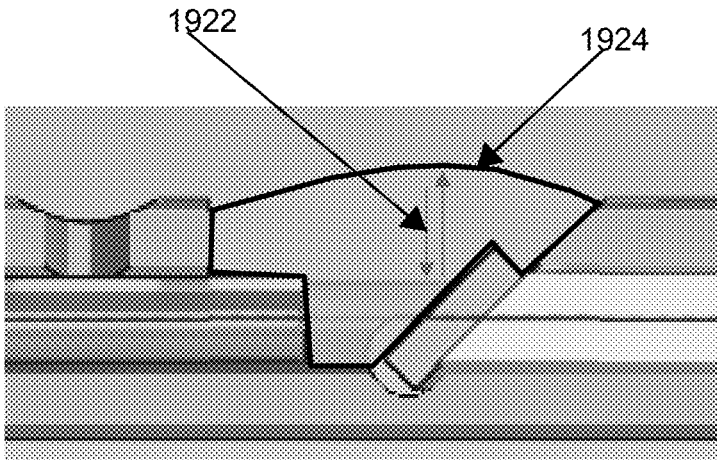
Figure 19D:
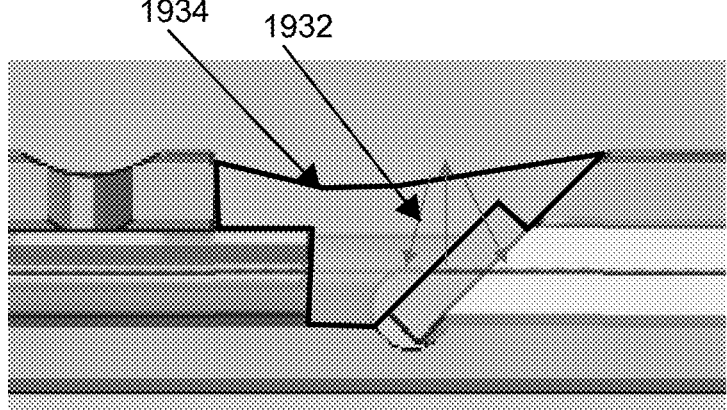
FIGS. 19D and 19E are schematic cross-sectional views of a side-viewing OCT imaging system with optical filler configurations that reduce back reflection.
Figure 19E:
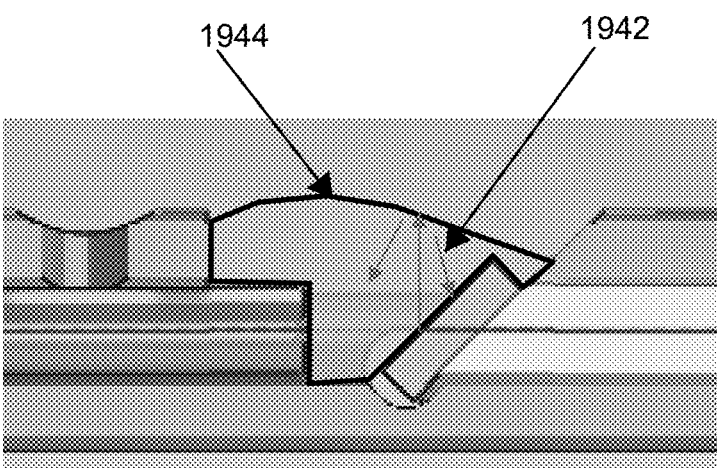

Many optical adhesives or curable materials that may be used as an optically transparent polymer, adhesive or filler material have a refractive index of greater than 1.5, but this results in a significant index mismatch with saline, blood and/or plasma, which may have a refractive index in the range 1.33 to 1.38. This results in visible artifacts, including ghost images, light streaks and/or ringing. FIG. 18A, for example, depicts an OCT image with a ring artifact 1802 from interface mismatch and also a light streak artifact 1804 that results from a strong refractive index mismatch that saturates the detector. FIG. 18B is another exemplary OCT image with a ring artifact 1812 and light streaks 1814. FIG. 18C is still another exemplary OCT image with a ring artifact 1816 and a ghost image 1818. To potentially ameliorate these artifacts, the contour of the filler material may be modified during manufacture from a cylindrical shape to a concave or convex shape along the length of the filler material, to reflect away the refractive index mismatch signal from the detector. FIG. 19A depicts the back reflection 1902 from the mismatch filler/fluid interface 1904 between the optical filler 1806 and the surrounding fluid/tissue 1906, while FIGS. 19B and 19C depicts a concave and convex interfaces 1914, 1924, respectively, centered about the lateral optical axis. FIGS. 19D and 19E depict concave and convex interfaces 1934, 1944 that are proximal or offset from the lateral optical axis, which reduces back reflection, 1932, 1942.

In some variations, the optically transparent polymer, adhesive or filler material may be selected with a refractive index of less than or equal to 1.5. For example, an aliphatic urethane acrylate with an acrylic monomer may be used, with a refractive index in the range of 1.30 to 1.40, for example. Such a material may improve manufacturing tolerances, repeatability of manufacturing process and manufacturability because such materials are less sensitive to reflection variations caused by meniscal concave/convex shapes and interfaces of high refractive index mismatch, and thereby minimizing or eliminating undesirable detector saturation and ghost images.

In some variations, the filler material may be a UV curable optical adhesive comprising mixtures of aliphatic urethane acrylate and acrylic monomers. Examples include Norland Optical Adhesives 133 and 13775 (Norland Products, Inc. Cranbury, NJ). NOA 133 has a refractive index of 1.33 and a pre-cure viscosity of 15 cps, and comprises a mixture of 1-15% aliphatic urethane acrylate and 85-99% acrylic monomer, while NOA 13775 has a refractive index of 1.3775 and a pre-cure viscosity of 4000 cps, and is a mixture of 80-99% aliphatic urethane acrylate and 1-20% acrylic monomer. In some variations, the selection of the filler material used may be selected based on the desired refractive index, as well as manufacturing characteristics, such as the viscosity. A viscosity of 15 cps may be too thin to easily manufacture, while 4000 cps may be too thick or viscose to handle at smaller volumes, for example. In some variations, a viscosity of the filler material may be in the range of 1000 to 3000 cps, 1500 to 3000 cps, 2000 to 2500 cps, for example. Notwithstanding aliphatic urethane acrylate and acrylic monomers, other polymeric materials with refractive index 1.30 to 1.40, a pre-curing viscosity between 1000 to 3000 cps, and post curing Shore D Hardness above 30 may be applicable. Another example of a low refractive index polymer material or filler are combinations of hexafluoroacetone and 3-aminopropyltriethoxysilane.

While the viscosity of the filler material may be further selected or modified by, for example, selecting materials with a different relative amounts of aliphatic urethane acrylate and acrylic monomer, the optical properties may or may not exhibit a linear relationship based on the relative percentages or ratios of the constituents. For example, a mixture comprising 50% by volume NOA 133 and 50% by volume NOA 13775 (40% to 57% aliphatic urethane acrylate and 43% to 60% acrylic monomer) had a refractive index of 1.274 at 1310 nm, while a mixture comprising 40% by volume NOA 133 and 60% by volume NOA 13775 (48% to 65% aliphatic urethane acrylate and 35% to 52% acrylic monomer) had a refractive index of 1.345 at 1310 nm. In other variations, the percentage of aliphatic urethane acrylate is in the range of 30% to 70% and the percentage of acrylic monomer is in the range of 70% to 30%, while in still other variations, the percentage of aliphatic urethane acrylate is in the range of 40% to 50% and the percentage of acrylic monomer is in the range of 60% to 50%.

Two or more mixture of optical adhesive with different refractive indices may be combined before curing to achieve the desirable or optical refractive index. For example, a mixture comprising 50% by volume NOA 133 and 50% by volume NOA 13775 (40% to 57% aliphatic urethane acrylate and 43% to 60% acrylic monomer) had a refractive index of 1.274 at 1310 nm, while a mixture comprising 40% by volume NOA 133 and 60% by volume NOA 13775 (48% to 65% aliphatic urethane acrylate and 35% to 52% acrylic monomer) had a refractive index of 1.345 at 1310 nm. The mix ratio to achieve the desirable refractive index may or may not be linear or proportional. The pre-curing and post-curing refractive index may or may not differ. A post-curing refractive index of 1.33 to 1.35 may index-match with water, saline and fluid, while a post-curing refractive index of 1.37 to 1.40 may index-match with soft tissue.

Figure 20A:
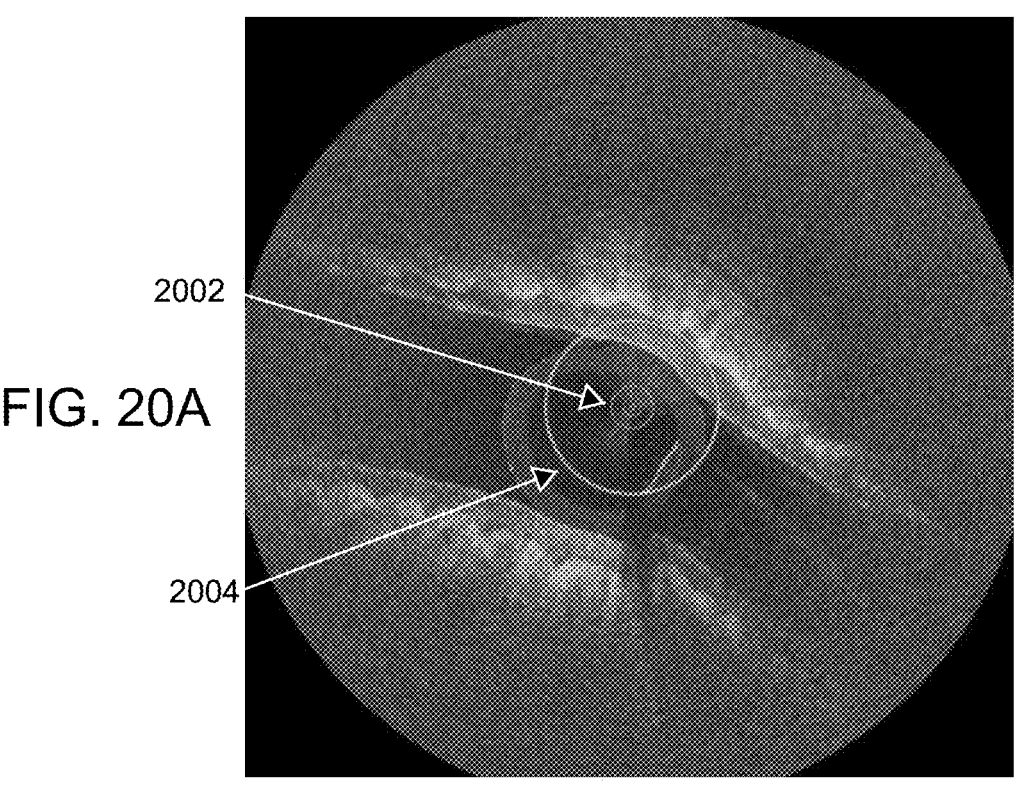
FIGS. 20A to 20C are OCT images with reduced artifacts resulting from a low refractive index optical filler material in the imaging system.
Figure 20B:
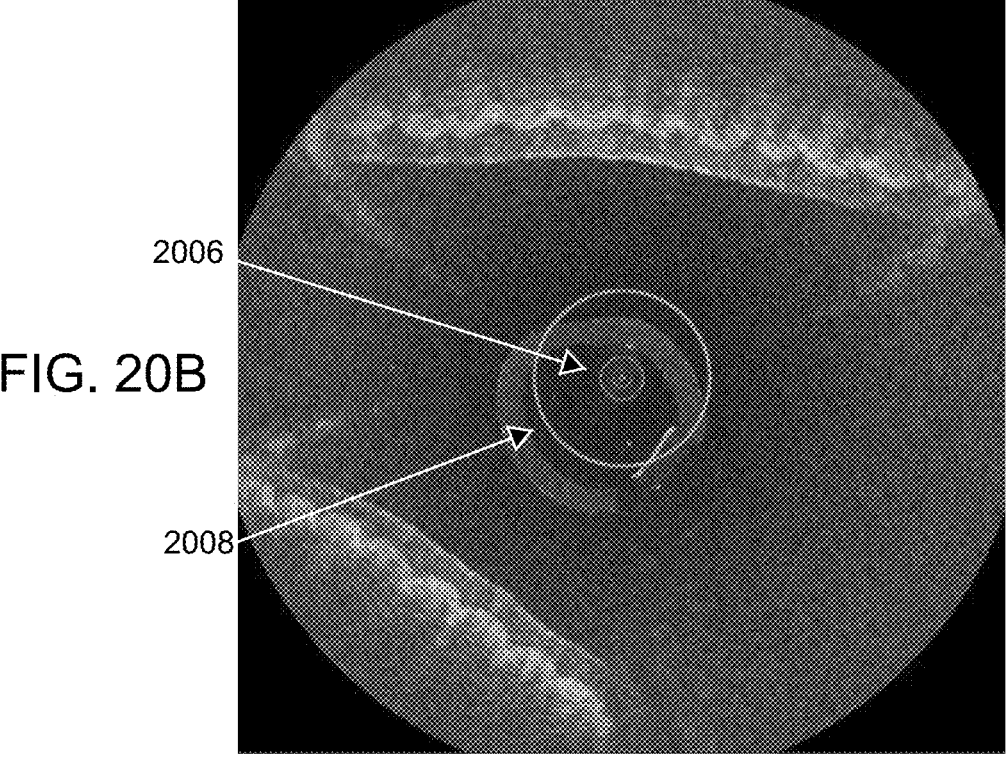
Figure 20C:
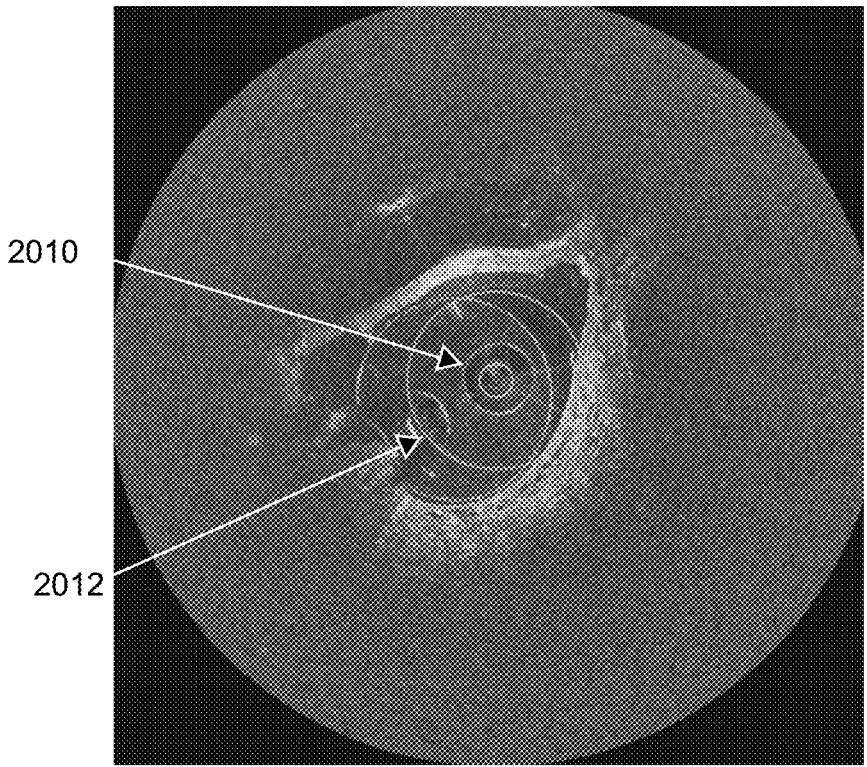

FIGS. 20A to 20C depict various OCT images from imaging system using a UV cured filler material comprising a 40/60 mixture of NOA 133 and 13775. As depicted, the signal intensity from the ring artifacts 2002, 2006, 2010, 2012 resulting from the filler/fluid interface is substantially reduced, compared to those in FIGS. 18A to 18C. This in turn reduces detector saturation and the corresponding light streaks found in FIGS. 18A and 18B, in addition to reducing the incidence of ghost images.

The low refractive index filler materials described herein may be used with any of a variety of OCT imaging devices and systems, whether used or not in an aqueous or biologic environment, and is not limited to the various exemplary OCT imaging embodiments described herein. For example, the low refractive index filler materials described herein may be used an OCT imaging probe that may or may not include the cutting tip or distal tapered ends or edges 204, 304, 404, 716 or 1004 described herein.

Figure 21A:
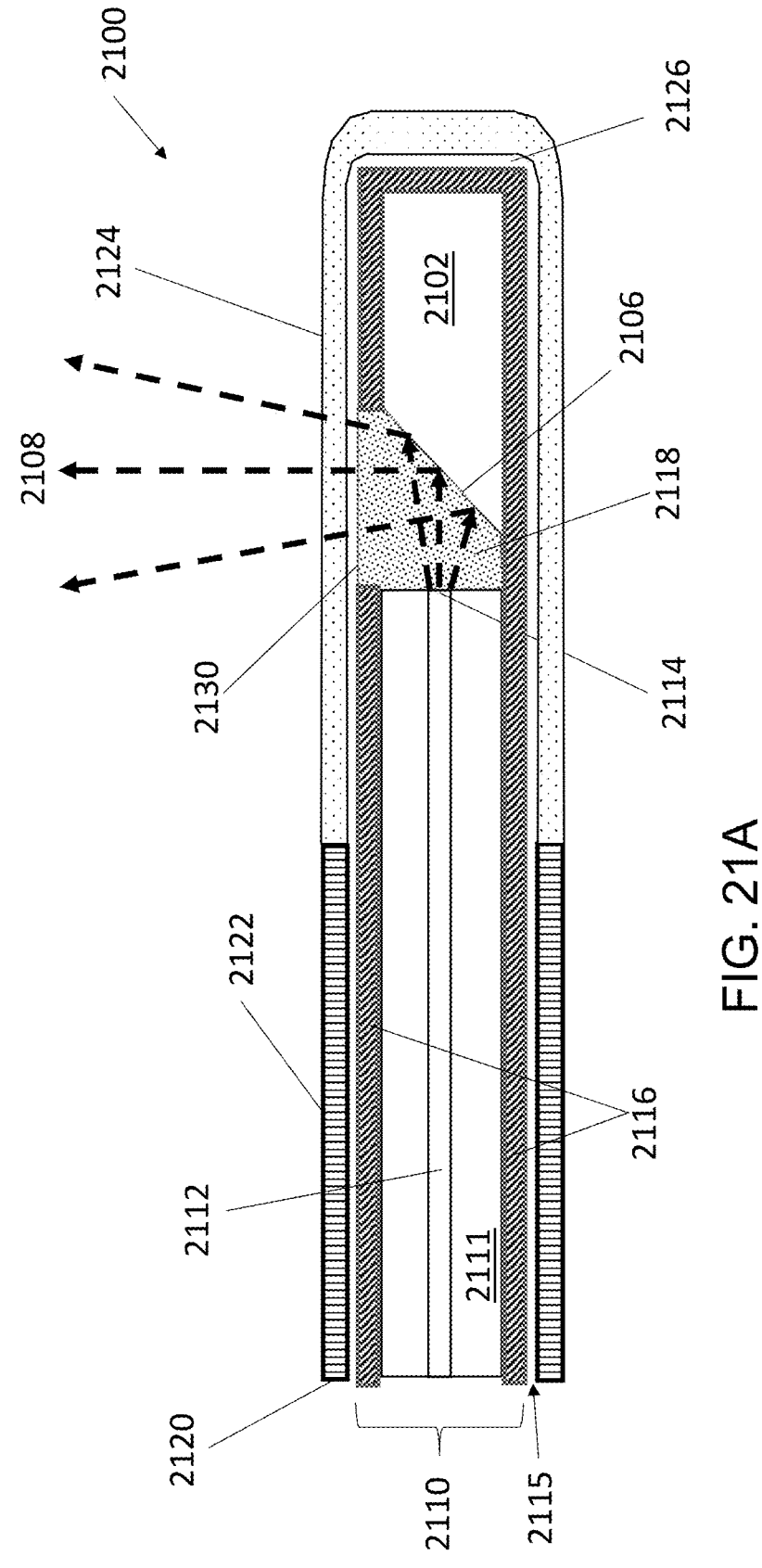
FIGS. 21A and 21B are schematic cross-sectional views of an OCT imaging system with a low refractive index optical filler, with and without an outer shaft, respectively.

FIG. 21A is a cross-sectional diagram of an exemplary distal end of an OCT imaging device 2100 with a low refractive-index filler material 2118, located between the distal end of the optical fiber 2114 and a reflecting surface 2106 of a tip structure 2102. The imagine device 2100 may include an inner core 2110 located in a lumen 2115 of an outer tubular shaft 2120. The inner element 2110 may be configured to rotate relative to the outer shaft 2120, and includes an optical fiber 2112 which transmits lights from a light source and receives light signals returning from the target structures. Light from the light source travels distally through the optical fiber 2112 and exits from the end 2114 of the optical fiber 2112 and through the optical filler 2118 before reflecting off of the reflecting surface 2106 of the tip structure 2102, to redirect the imaging beam 2108 toward the target structure.

The outer shaft 2120 may have an outer diameter of around 0.020 inches or less, 0.045 inches or less, or may comprise diameters sized according to common guidewire dimensions, including 0.014 inch, 0.018 inch and 0.35 inch. The outer shaft 2120 may comprise a unibody design, or may comprise a body 2122 and cap 2124 that are joined during the manufacturing process. The body 2122 may be formed from a coil or hypotube. The body 2122 and cap 2124 may have similar or different outer diameters and wall thicknesses. As with other variations described herein, the cap 2124 may comprise a different material, e.g., an optically transmissive material to facilitate light transmission through the cap 2124. In some embodiments, the cap 2124 may include a window, for example such as a laser cut window through the material of the cap 2124. In some embodiments, the laser cut window may include a cover made from an optically transparent material. In some embodiments, the window may be uncovered. In some embodiments, the body 2122 of the outer shaft 2120 may be made from an optically transparent material, and a separate cap 2124 may be unnecessary.

The inner core 2110 may be a generally cylindrical member which is disposed in a lumen 2115 of the outer shaft 2120. The inner core 2110 may have an outer diameter of around 0.010 inches (0.254 mm) or less. The inner core 2110 may be extendable/retractable relative to the outer shaft 2120 along a longitudinal axis of the imaging device 2100 and may be rotatable relative to the outer shaft 2120. For example, a motor/drive assembly (e.g., 126 of FIG. 1) may move the inner core 2110 relative to the outer shaft 2120. This may facilitate movement of the imaging area without requiring movement of the outer shaft 2120.

The optical fiber 2112 is configured to transmit light between an optical unit (e.g., 112 of FIG. 1) coupled to a proximal end of the imaging device 2100 and the distal end of the imaging device 2100. The optical fiber 2112 may be a single fiber or a multi-core fiber. The optical fiber 2112 may be surrounded by a cladding material 2111, which may support the optical fiber 2112 and provide optical conditions (e.g., an index mismatch) which facilitate the transmission of light along the optical fiber 2112. The cladding material 2111 may in turn be surrounded by a fiber reinforcement 2116. The fiber reinforcement 2116 may support the optical fiber 2112 and cladding material 2111. In some embodiments, the fiber reinforcement 2116 may be a coil or a modified hypotube.

The end 2114 (and cladding material 2111) of the optic fiber 2114 may be a flat surface (e.g., a cut in the fiber) which is at a right angle to the long axis of the imaging device 2100, but in other variations, may comprise a non-orthogonally oriented surface. Some light traveling distally through the fiber 2112 may be reflected back at the end 2114 of the fiber 2112, to function as the local oscillator (LO) portion of the light, which is interferometrically combined with received light in an optical unit (e.g., optical unit 112 of FIG. 1).

The reflecting surface 2106 of the tip structure 2102 is configured to redirects light from an optical axis generally aligned with the long axis of the fiber 2112, and an optical axis directed to a side of the imaging device 2100. For example, the reflecting surface 2106 may redirect light at about a right angle. The reflecting surface 2106 may be a slanted surface at a proximal end of the tip structure 2102. The angle of the reflecting surface 2106 with respect to a long axis of the imaging device 200 may be configured based on the desired deflection of light which reflects from the reflecting surface 2106. For example, in some embodiments, the reflecting surface 2106 may have an angle of about 45 degrees. In some embodiments, the reflecting surface 2106 may be coated with a reflective material, such as gold. As depicted in FIG. 21A, the low refractive index filler material 2118, described herein, located between the end 2114 of the optic fiber 2112 (or lens located at the end 2114 of the optic fiber 2112 and the reflecting surface 2106 of the tip structure 2102. The refractive index mismatch between the outer surface 2130 of the filler material 2118 and the surrounding fluid or tissue is reduced along with image artifacts as a result of the low refractive index material used.

Figure 21B:
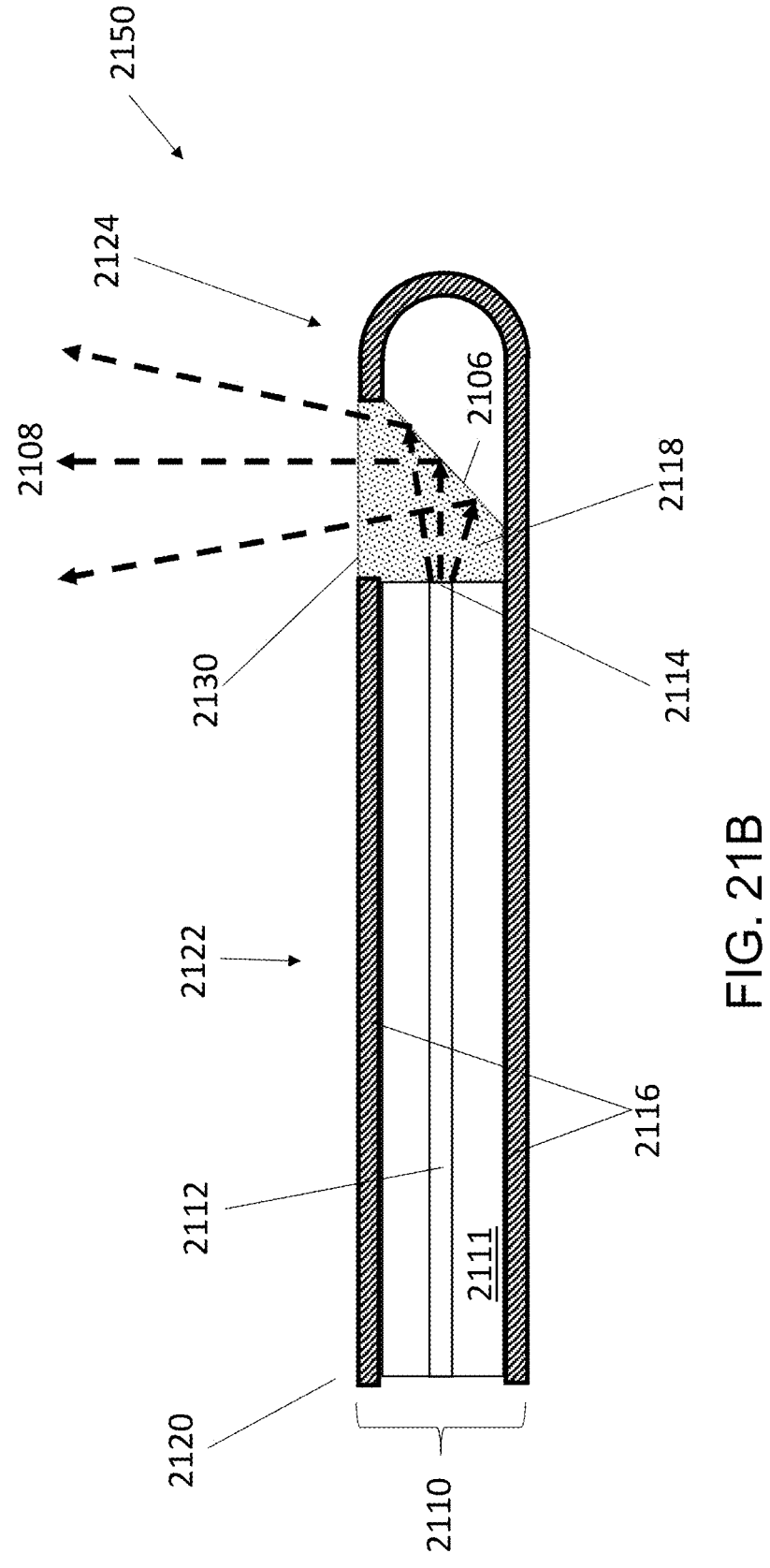

In other variations, as depicted in FIG. 21B, an outer tubular shaft is not provided or required, as the imaging device 2150 is configured for insertion and use inside a lumen of a catheter or other tool, to provide OCT imaging, but may be otherwise similar to the inner core structure 2110 of the imaging device 2100 in FIG. 21A.

Figure 22A:
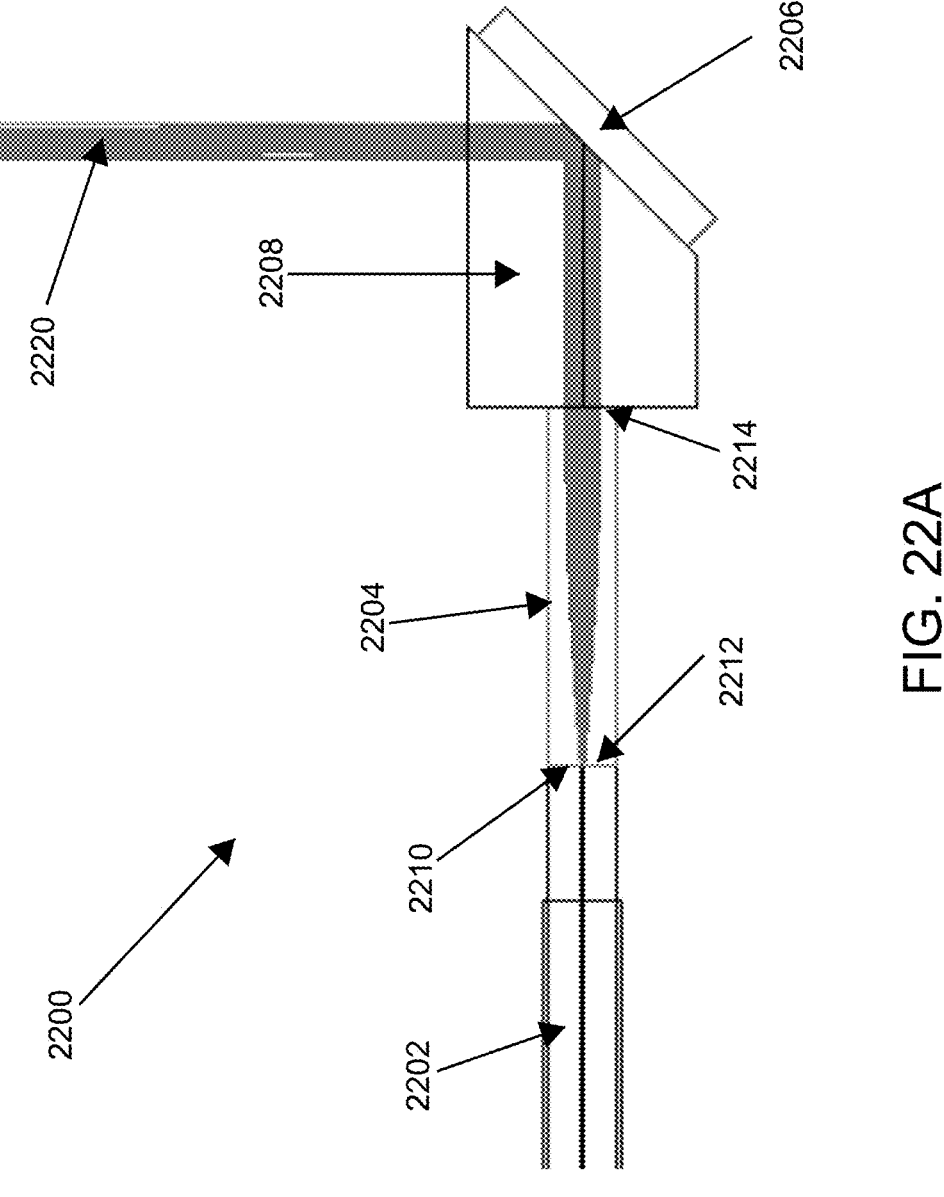
FIGS. 22A and 22B are schematic depictions of variations of the OCT imaging assembly comprising a GRIN lens, without and with a non-clad fiber segment, respectively.
Figure 22B:
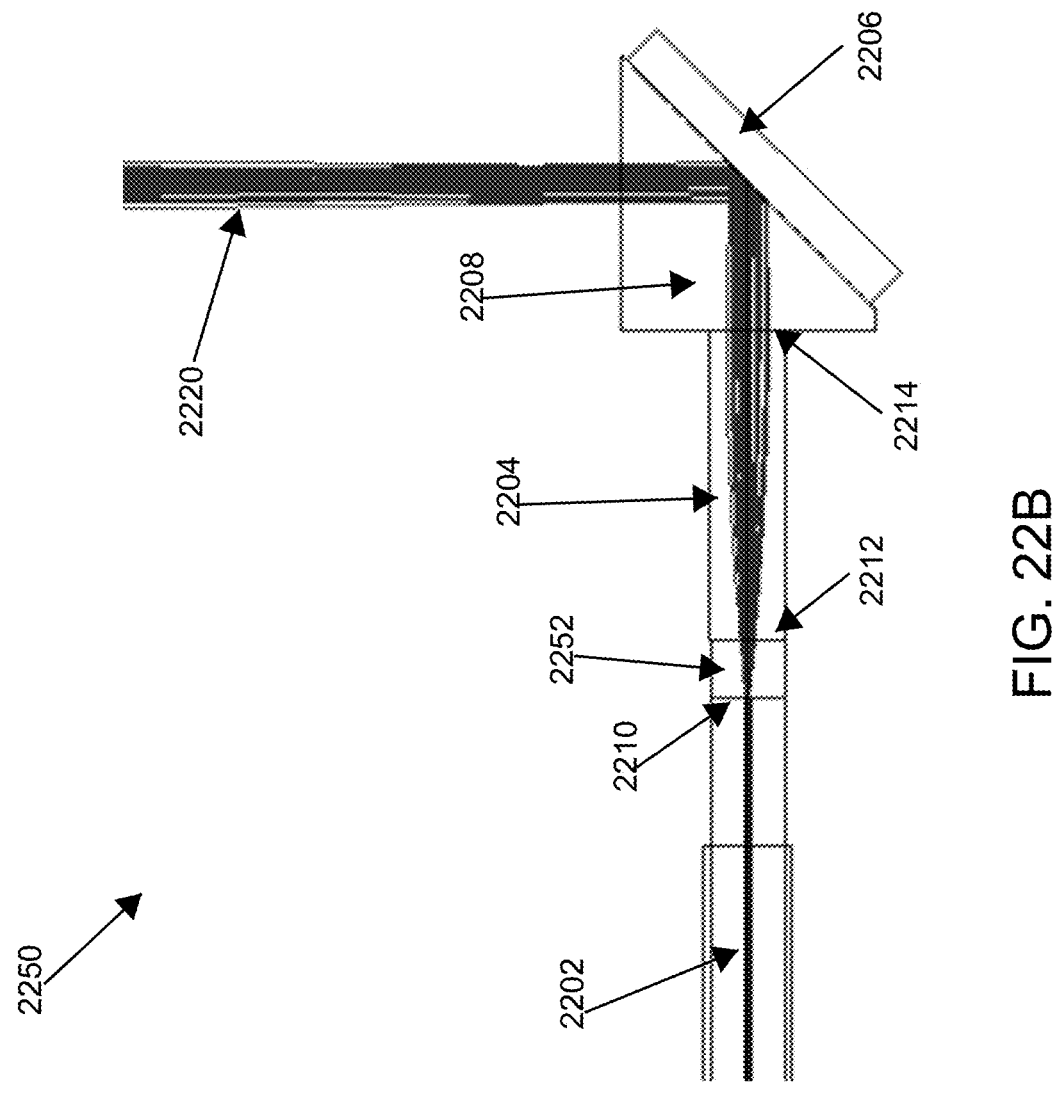
Figures 22C, 22D:
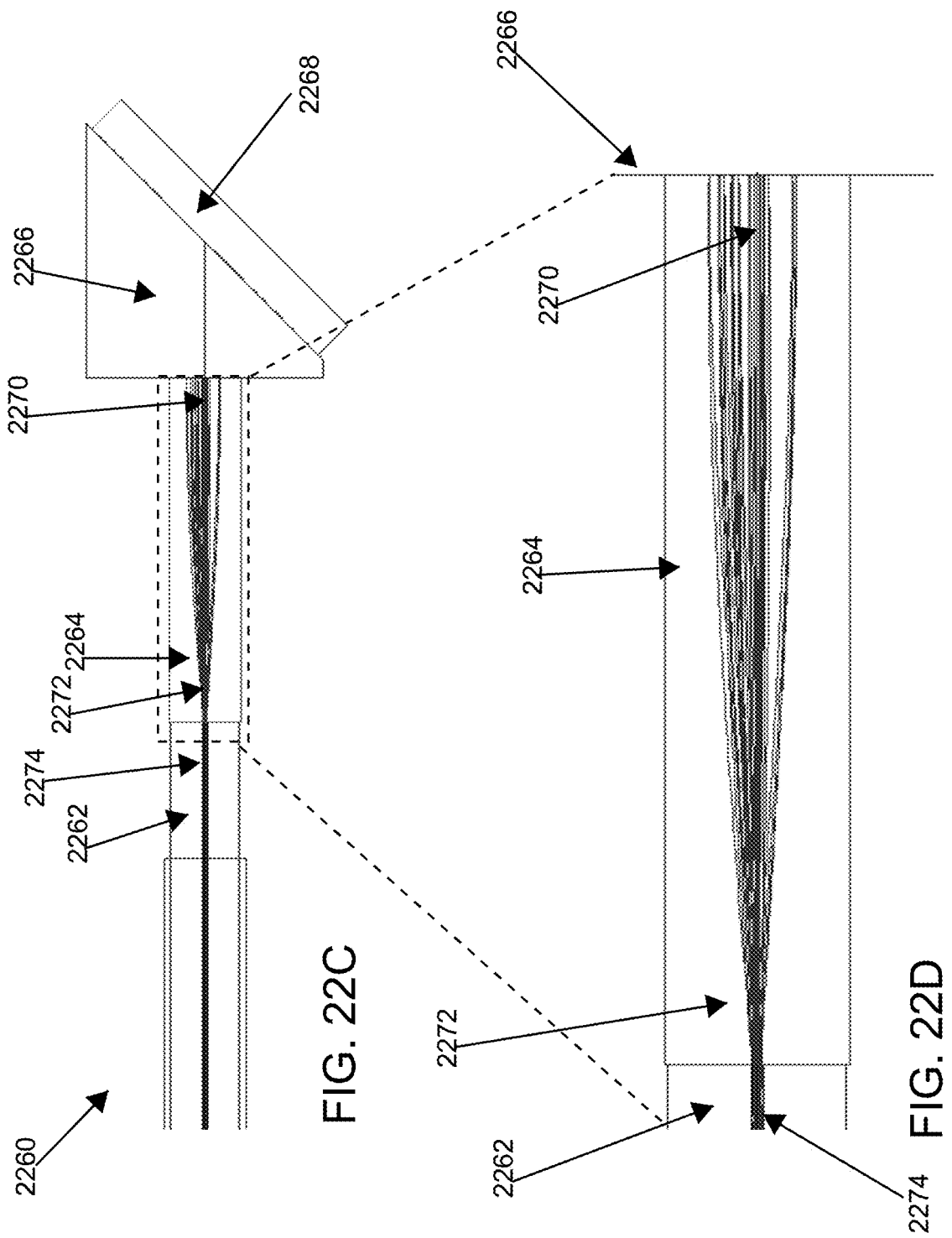
FIGS. 22C and 22D schematically depict an OCT imaging assembly with a GRIN lens configured to produce a collimating beam.
Figures 22E, 22F:
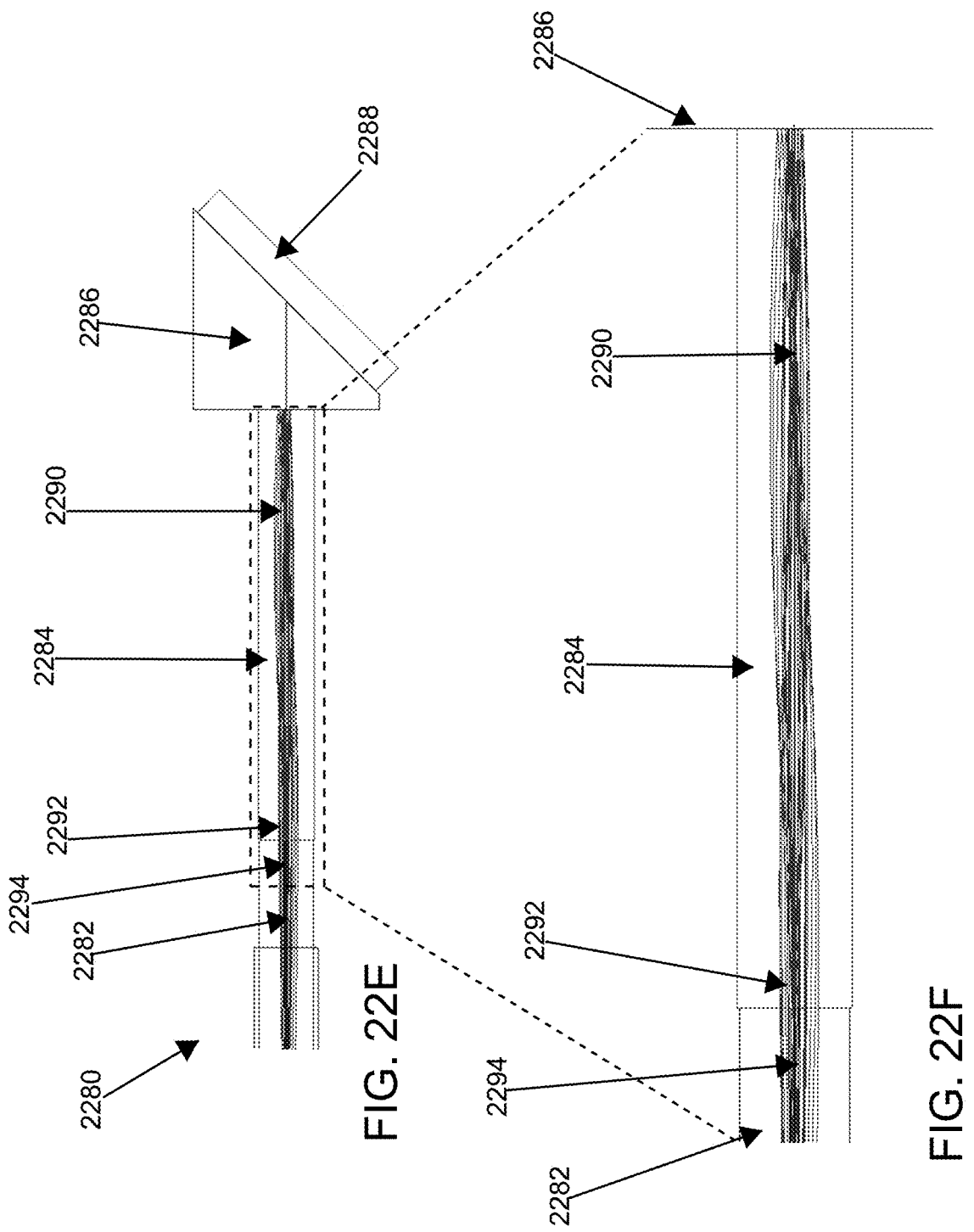
FIGS. 22E and 22F schematically depict an OCT imaging assembly with a GRIN lens configured to produce a focusing beam.
Figures 29A, 29B:
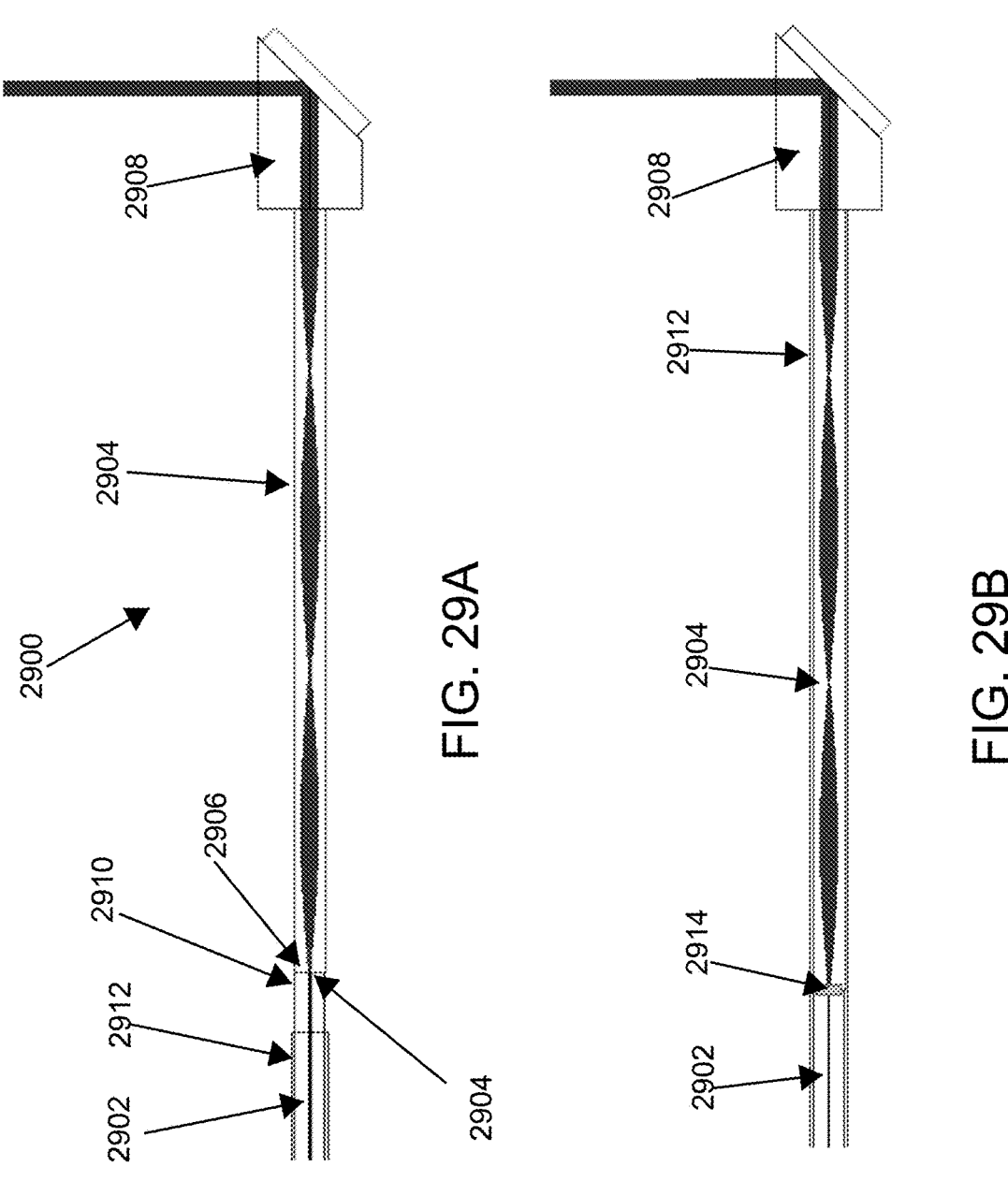
FIGS. 29A and 29B schematically depict the mechanical coupling of an optical fiber and GRIN lens.

Referring to FIG. 22A, in other variations, the OCT imaging system 2200 may comprise an optical fiber 2202, lens 2204, a mirror or reflector 2206 and a low refractive index filler material 2208 between the lens 2204 and reflector 2206. As noted elsewhere, the optical fiber 2202 may be a single-mode fiber, but in other variations may be a multi-mode fiber. The distal surface 2210 of the fiber 2202 and proximal surface 2212 of the lens 2204 may be mechanically spliced or fusion spliced. The surfaces 2210 and 2212 are cut or cleaved with complementary geometries and then mechanically aligned. This may be flat surfaces that are each perpendicular to the axis of the fiber 2202, but in other variations may comprise non-flat surfaces or non-perpendicular orientations of the surfaces. FIG. 29A depicts an example of an OCT imaging system 2900 that has been mechanically spliced with an optical fiber 2902 with a distal surface 2904 that is flat and comprising a 90-degree orientation with respect to the longitudinal axis of the fiber 2902. This surface 2904 is against a corresponding proximal surface 2906 of a lens 2908, where the surface 2906 is also flat and comprising a 90-degree orientation. As further depicted in FIG. 29A, the distal region 2910 of the optical fiber 2902 may have its jacket 2912 removed. In some further variations, as depicted in FIG. 29B, after splicing the fiber 2902 and lens 2204 may be re-coated and partially or fully re-jacketed, which may improve light streaking, ringing, ghost images and other image artifacts. In further variations, an optical adhesive with a refractive index similar to that of the fiber 2902 and/or lens 2904 may be used, or the fiber 2202 and lens 2204 may be fused or welded together. This fusion may result in a loss of single-mode coupling and form an intermediate zone 2914 of optical functionality between the optical fiber 2902 and lens 2904.

Figures 23A, 23B:
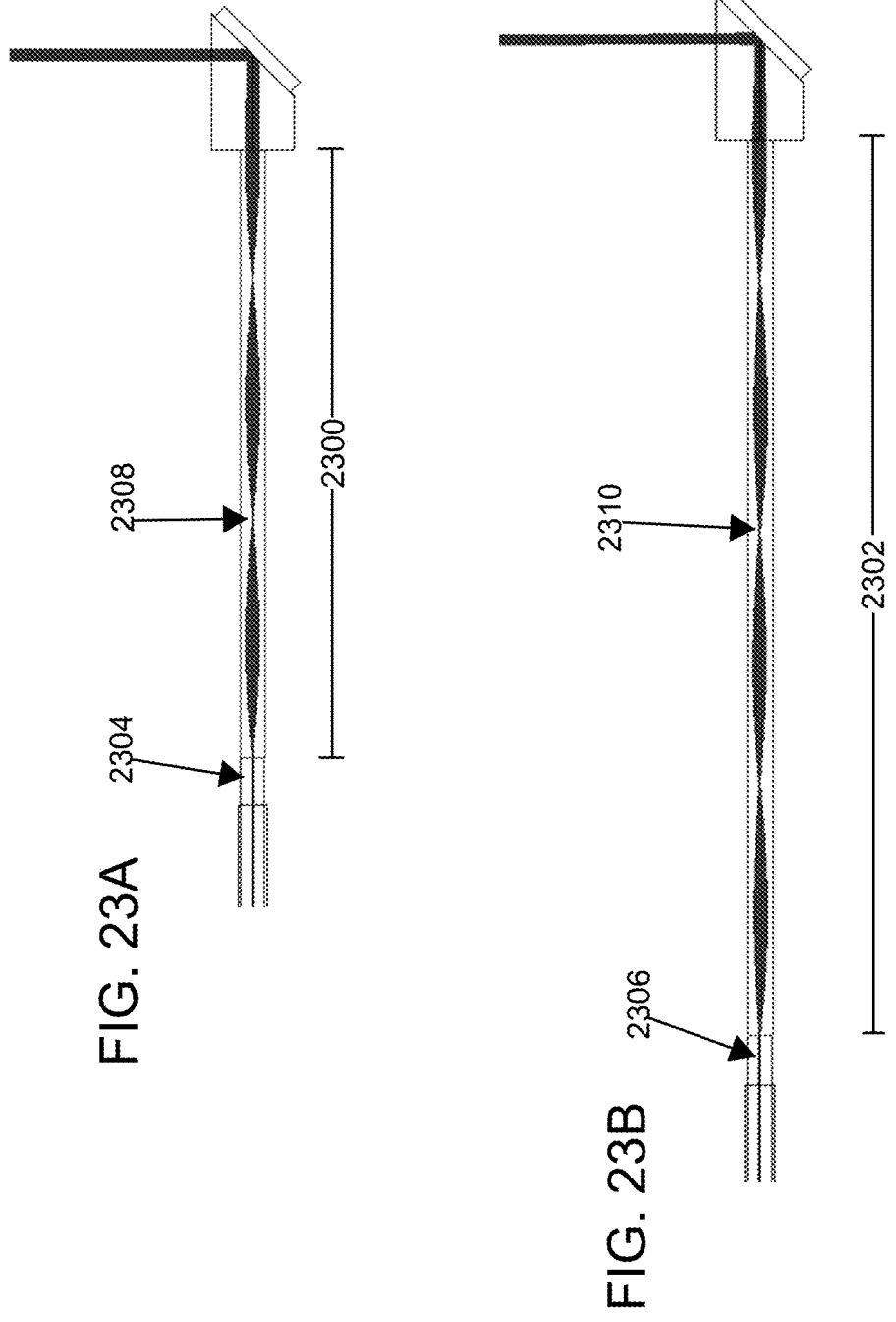
FIGS. 23A and 23B are schematic depictions of other variations of the OCT imaging system with a GRIN lens.

Referring back to FIG. 22A, the lens 2204 may be a GRIN lens. In this particular embodiment, the length of the GRIN lens corresponds to one-quarter of a full sinusoidal path or pitch of the lens 2204, but in other variations may comprise a length equal to or corresponding to any odd-multiple of a quarter pitch, e.g. ¾ pitch length, one and ¼ pitch length 2300 (FIG. 23A), one and ¾ pitch length 2302 (FIG. 23B), or more. One potential benefit of the increased length is that the ring artifacts (e.g., artifacts 2004, 2008, 2012 in FIGS. 20A, 20B and 20C) resulting from the reflective interface between the optical fiber 2304, 2306 and the GRIN lens 2308, 2310, respectively, will exhibit increased diameters in the image, such that the ring artifact may be enlarged to a size where it lies outside of the effective field of view. This reflective artifact is typically stronger or larger than −40 dB.

As depicted in FIG. 22A, the GRIN lens 2204 may output a collimated beam 2220 through the low refractive index material 2208 and as reflected by the mirror or reflector 2206. The beam diameter may be configured to be nominally in the range of 20 μm to 200 μm. The distal surface 2214 of the GRIN lens 2204 and the polymer material 2208 may also be at a 90-degree surface angle relative to the axis of the optical fiber 2202. This may ensure that any light rays reflecting at the lens/polymer interface will have the same reflective path of partial reflection, which may provide improved consistency/reproducibility during manufacturing and provide a stable and optimal return loss (RL) or reference signal. In some variations, the RL at the lens/polymer interface may be in the range of −14 dB to −28 dB, or −15 dB to −35 dB, or −20 dB to −40 dB, for example.

For example, FIGS. 22C and 22D depict general and close-up schematic views of one example an OCT imaging assembly 2260 configured with a collimating beam 2270, comprising a single mode optical fiber 2262, GRIN lens 2264, low index polymer material 2266 and mirror 2268. The light beam 2270 will exit the single mode optical fiber 2262 and is collimated by the GRIN lens 2262, but at the interface between the GRIN lens 2262 and the low refractive index polymer 2266, a partial reflection of the collimated beam 2270 occurs, with a RL typically in the range of −14 dB to −35 dB at the interface. Depending on the specific design, RL range of −14 dB to −40 dB, or −15 dB to −35 dB, or −20 dB to 35 dB or −25 dB to −35 dB may be achieved. As this reflected beam 2272 travels back toward the optical fiber 2262, the GRIN lens 2264 will focus the reflected beam back into the single mode fiber core 2274, which may have a size of 10 μm or less, 9 μm or less, or 8 μm or less, for example. This may result in a high effective RL of the reference signal. This high RL is achieved at local maxima of the optimal GRIN length for beam collimation, which can be found at or around 0.5 pitch unit length, 0.75 pitch unit length, 1.25 pitch unit length, 1.75 pitch unit length, and so forth, This may be beneficial for improving manufacturability and repeatability, allowing for +/−10% tolerance about the optimal GRIN unit length.

In comparison, an OCT imaging assembly 2280 configured with a focusing light beam 2290, illustrated in FIGS. 22E and 22F, and comprising a single mode optical fiber 2282, GRIN lens 2284, low refractive index polymer material 2286 and mirror 2288. As the light beam 2290 exits the single mode optical fiber 2282, it is partially focused by the GRIN lens 2284, and then is partially reflected at the junction of the GRIN lens 2284 and the low refractive index polymer material 2286. This partial reflection 2292 may result in low RL in the range of −35 dB to −60 dB. As the reflected beam returns toward the optical fiber 2282, however, it is not refocused back into the fiber core 2294, resulting in a low and lossy, ineffective RL of the reference signal. As the reflective reference when the GRIN length is configured to focusing the beam, it is centered away from local maxima of optimal GRIN length for beam collimation, resulting in unpredictable RL and less manufacturability.

The GRIN lenses in the exemplary OCT imaging systems described herein may be coated or uncoated. They may comprise a length in the range of 500 um to 700 um, 600 um to 800 um or 700 um to 1100 mm, 800 um to 5000 um, a diameter in the range of 65 um to 130 um, 100 um to 200 um or 125 um to 500 um, and a pitch length of 0.500 mm to 1.200 mm, 0.600 mm to 1.500 mm or 0.700 mm to 2.000 mm (at a wavelength in the range 750 nm to 1380 nm, for example).

The reflector 2206 may comprise a mechanical and/or electropolished surface that is typically oriented at a 45-degree angle relative to the longitudinal axis of the optical fiber. The angle may be deliberately varied between 35 and 65 degrees. The reflector 2206 may comprise a layer of gold, silver, tin, nickel chromium, aluminum, dielectric or multi-layer dielectric or other coatings, with the coating process involving chemical vapor deposition, physical vapor deposition, sputtering, electroplating, etc. The coating thickness may be between 50 nm to 300 nm, or 100 nm to 250 nm, or 100 nm to 200 nm. The base material for the reflector may be optical glass, ceramic, semiconductor materials, or polymer.

Figure 24:
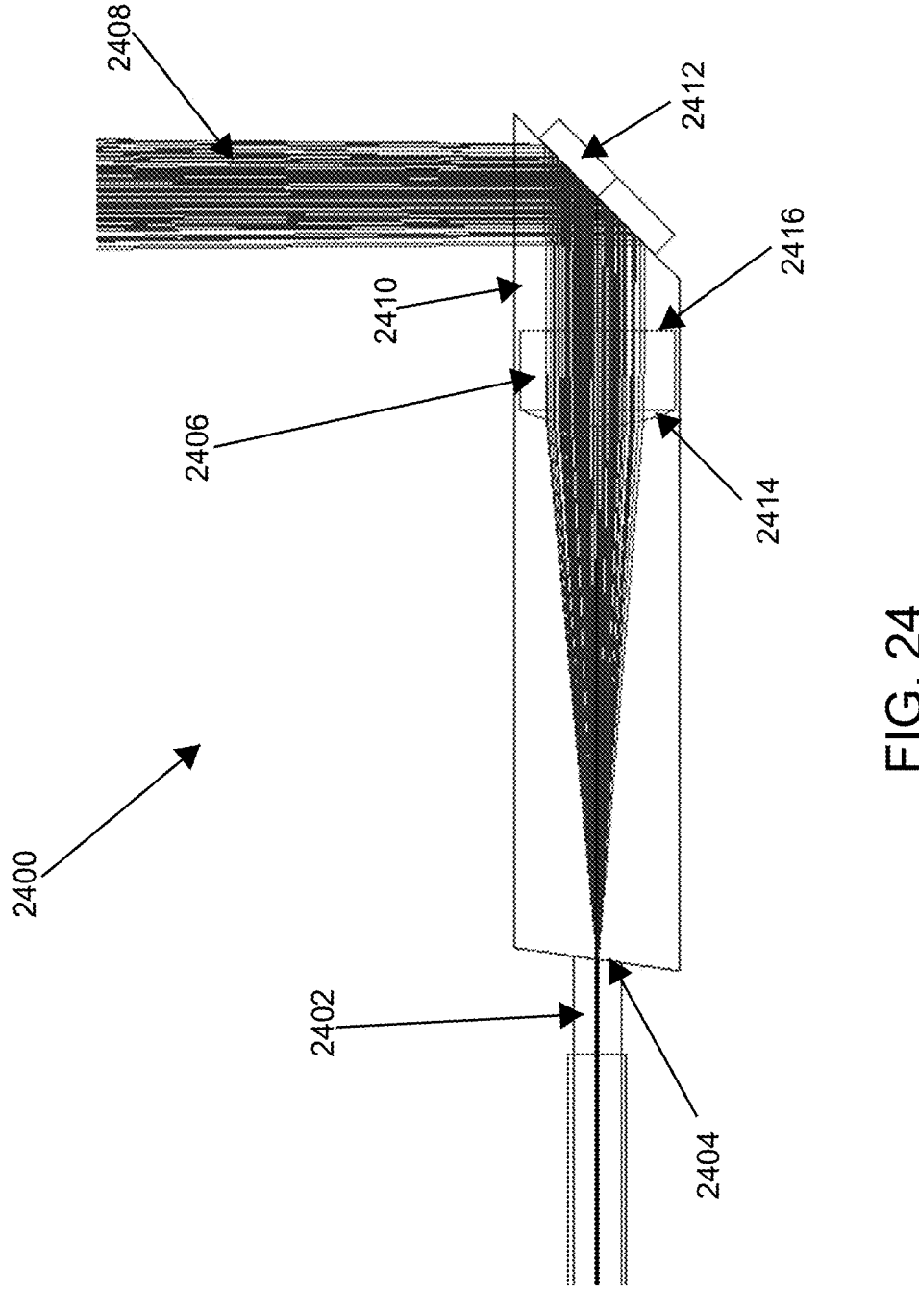
FIG. 24 is a schematic depiction of a variation of the OCT imaging system comprising a spherical or aspheric lens with collimated light.

FIG. 24 depicts another embodiment of an OCT imaging system 2400, wherein the optical fiber 2402 comprises a distal end or surface 2404 that was cleaved or configured with an angle that was not orthogonal to the longitudinal axis of the fiber 2402, and instead comprises a surface angle that is angled at least 8, 10, 12, 15 or more degrees from the orthogonal orientation, which may reduce or eliminate reflection artifacts. A spherical or aspheric lens 2406 may be spaced apart from the distal surface 2404 of the optical fiber 2402 to receive and collimate the light beam 2408. The light beam 2408 then continues through the low refractive index material 2410 and is reflected by the mirror or reflector 2412 out of the materials 2410 and out of the imaging system 2400. The spherical or aspheric lens 2406 may comprise a refractive index in the range of 1.50 to 1.85, for example, with and a plano-convex configuration with a convex proximal surface 2414 having a radius of curvature in the range of 0.20 to 1.00 mm and a flat distal surface 2416. The RL or reference signal at the interface between the lens and polymeric materials 2410 may be in the range of −14 dB to −40 dB, or −15 dB to −35 dB, or −20 dB to 35 dB or −25 dB to −35 dB. The cavity or space between the fiber 2402 and the lens 2406 may be filled with the same material as 2410 or a different material, e.g. a polymeric material with a higher refractive index in the range of 1.45 to 1.48, 1.40 to 1.50, or 1.5 to 1.85, or a different low refractive index material, for example, e.g. a refractive index in the range 1.30 to 1.48. The refractive index of the material in the space between the fiber and 2402 and the lens 2406 shall be lower than that of the lens 2406. The spacing between the end of the optical fiber and the lens may be in the range of 0.1 mm to 4.0 mm, or 0.3 mm to 3.0 mm, or 0.5 mm to 2.00 mm, for example. The spacing between the distal surface of the lens and the center of the reflector may be in the range of 0.025 mm to 0.250 mm, 0.050 to 0.500 mm, 0.1 mm to 3.0 mm, or 0.2 mm to 2.0 mm, or 0.3 mm to 2.00 mm, for example.

Figure 25:
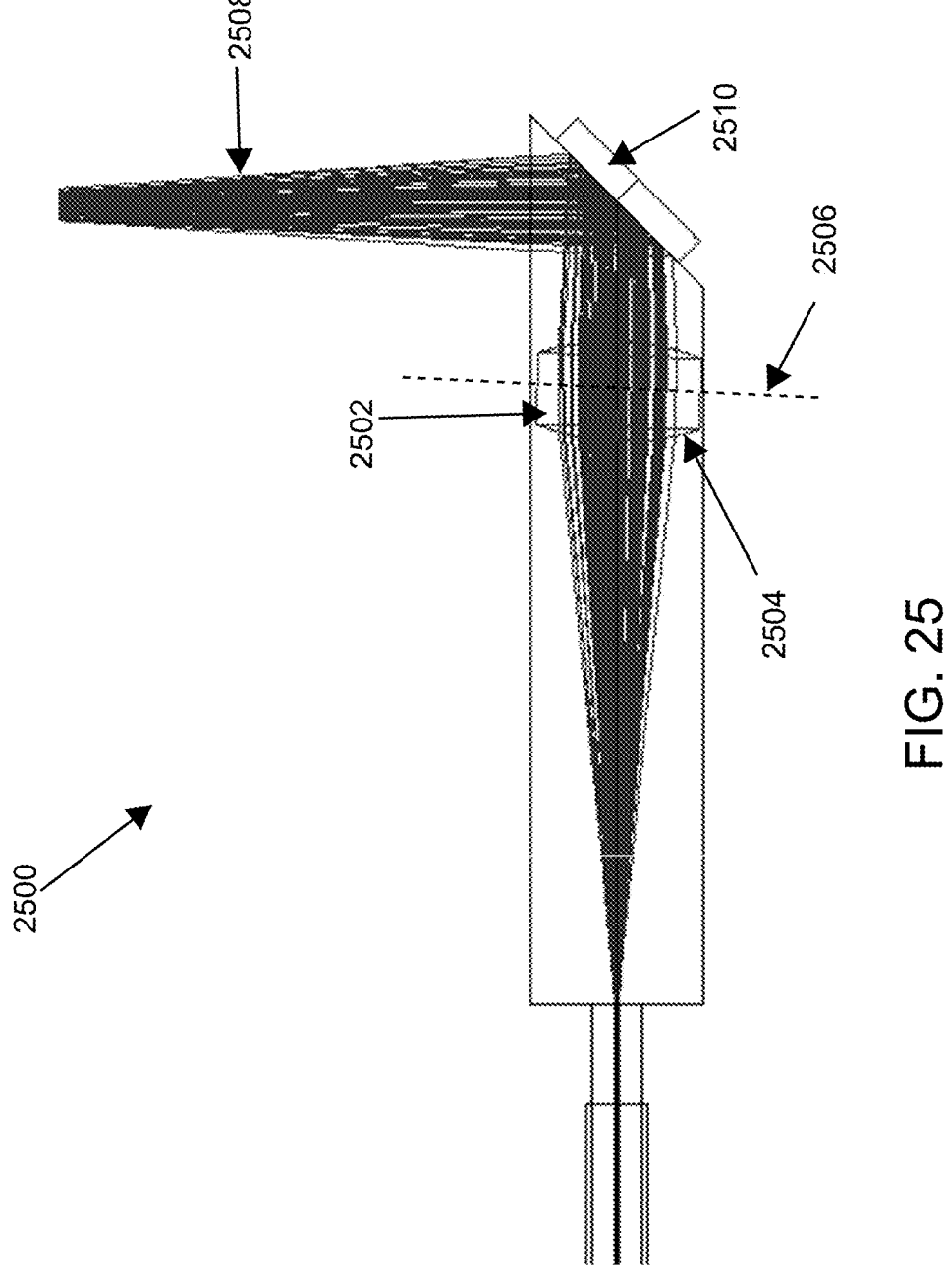
FIG. 25 is a schematic depiction of a variation of the OCT imaging system comprising a spherical or aspheric lens with collimated or non-collimated light.

FIG. 25 depicts another variation of an OCT imaging system 2500 that is similar to the OCT imaging system 2400 of FIG. 24, except that instead of a plano-convex lens, a double-convex lens 2502 is provided. The radius of curvature of the proximal convex surface 2504 may also be in the range of 0.20 mm to 1.00 mm and the refractive index may be in the range of 1.50 to 1.85. In this particular example, the lens 2502 may comprise a lens tilt 2506 in the range of 0.10 degrees to 2.00 degrees. The tilt minimizes or eliminate a reflection artifact by deflecting any interface reflection from the lens 2502 away from the optical fiber. In this embodiment, the return loss or reference signal is collected from the interface between the optical fiber and the polymeric material between the optical fiber and the lens 2502 in the range of −14 dB to −40 dB, or −15 dB to −35 dB, or −20 dB to 35 dB or −25 dB to −35 dB. The lens 2502 may be configured to provide a non-collimated light beam 2508, as depicted in FIG. 25, or a collimated light beam. For non-collimated embodiments, the focal distance of the OCT system may be 0.250 mm to 4.00 mm from the longitudinal axis of the OCT imaging system 2500 or center of the mirror or reflector 2510.

Figures 26A, 26B:
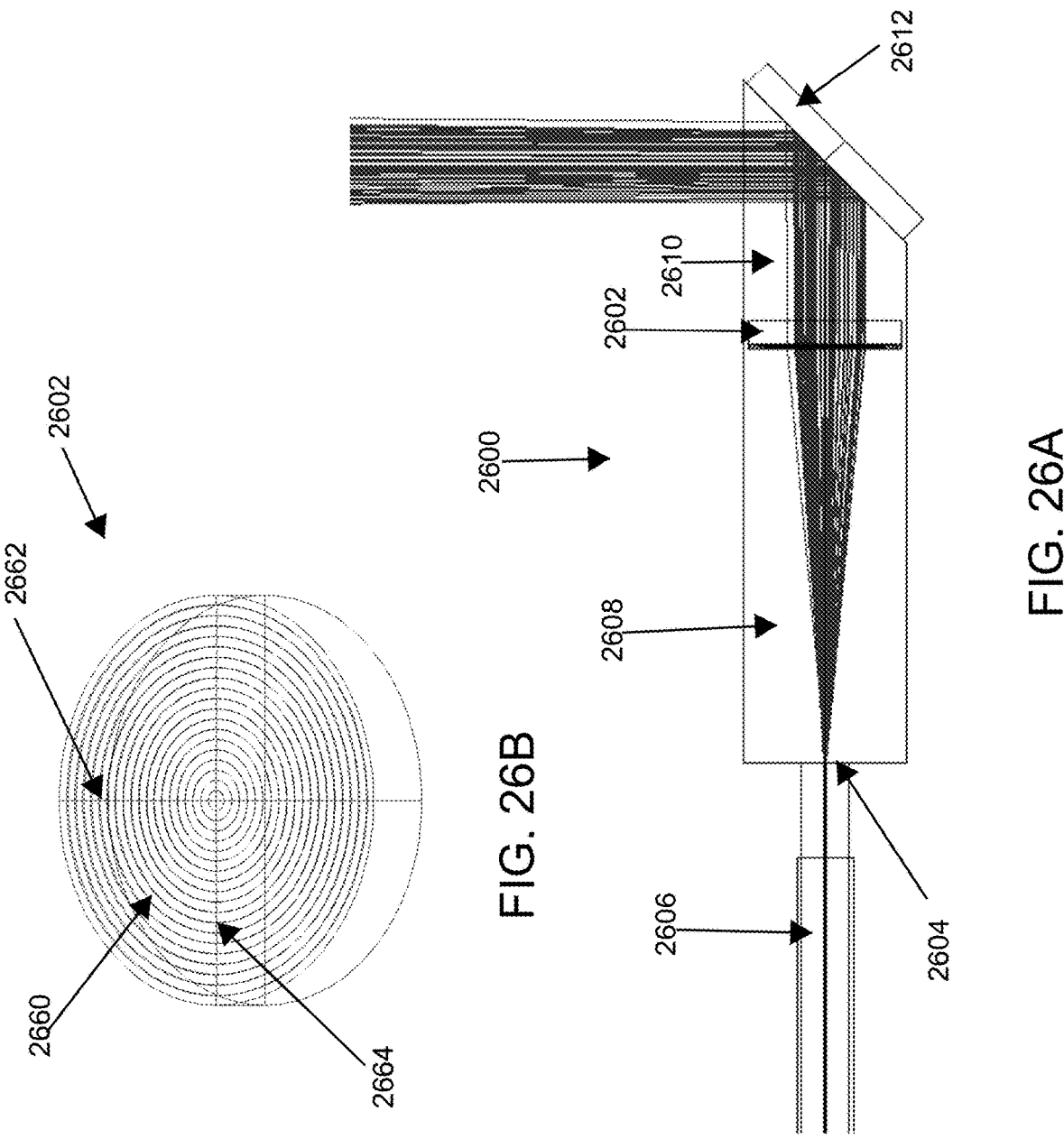
FIGS. 26A and 26C schematically depicts an embodiment of an exemplary OCT imaging system with a Fresnel lens.
FIG. 26B is a perspective component view of the Fresnel lens in FIG. 26A.
Figure 26C:
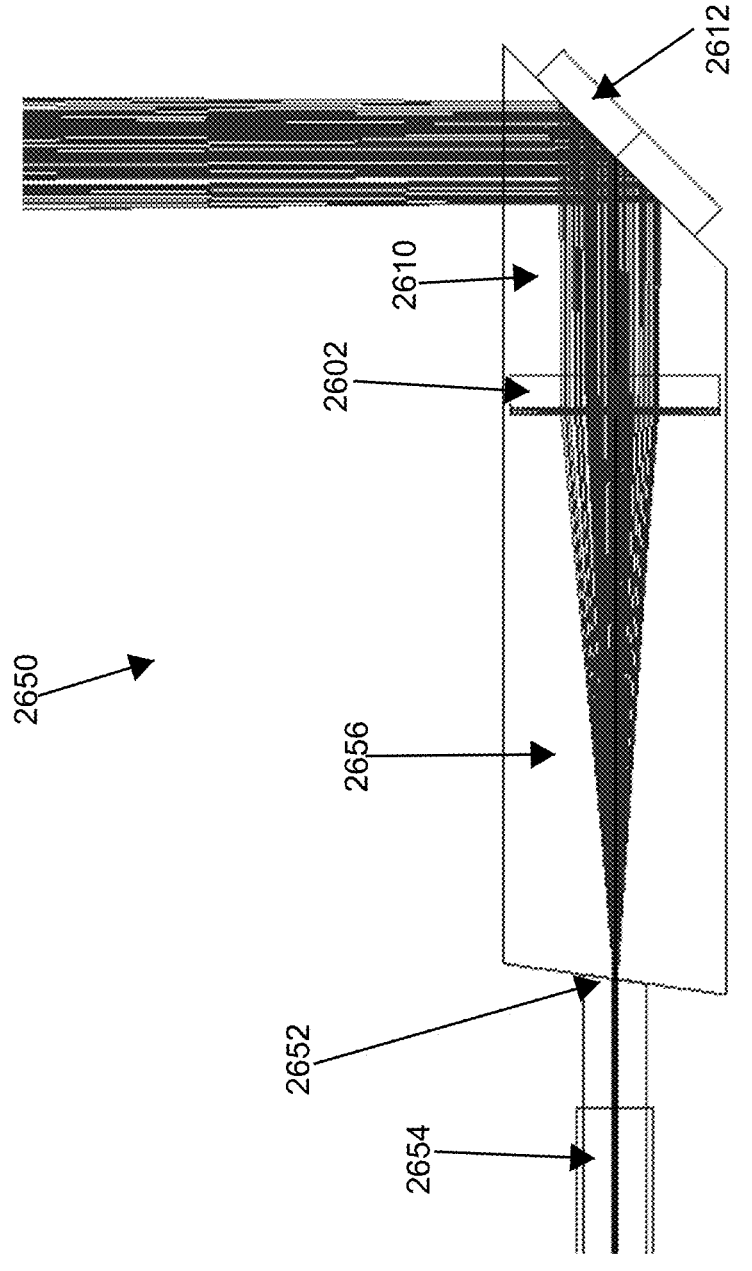

FIGS. 26A and 26C depict additional exemplary embodiments of an OCT imaging system 2600, 2650 wherein instead of a GRIN lens or spherical/aspheric lens, a Fresnel lens 2602 is provided. The Fresnel lens 2602 may be configured with a grating or diffractive pattern that is optically equivalent to a radius of curvature of 0.20 mm to 1.00 mm of a convex lens. Like some other embodiments described herein the Fresnel lens 2602 may be spaced apart from the end 2604, 2652 of the optical fiber 2606, 2654 in the range of 0.1 mm to 4.00 mm, 0.2 mm to 3.00 mm, or 0.5 mm to 2.5 mm, for example. The gap or cavity 2608, 2656 between the end 2604, 2652 of the optical fiber 2606, 2654 and the Fresnel lens 2602 may be filled with a polymeric material 2608, 2656. In some further variations, the polymeric material 2608, 2656 may be a low-index material with n<1.50 or in the range of 1.30 to 1.48, for example. The polymeric material 2610 between the lens 2602 and the reflector 2612 may be in the range of 1.30 to 1.40, or between 1.30 to 1.48, or 1.30 to 1.30, or 1.32 to 1.38, and may be the same or different from the proximal polymeric materials 2608, 2656. In some variation, the polymeric material 2610 may be higher refractive index in the range of 1.50 to 1.70, or 1.52 to 1.65. The interface between the optical fiber 2606, 2654 and the proximal polymeric material 2608, 2656 may be flat and may be at a 90-degree angle as depicted in FIG. 26A, or may be offset from the 90-degree angle as depicted in FIG. 26C, by at least 8, 10, 12, 15 or more degrees from the orthogonal orientation, for example. FIG. 26A depicts an embodiment with a RL or reference signal from interface 2604 in the range of −14 dB to −40 dB, or −15 dB to −35 dB, or −20 dB to 35 dB or −25 dB to −35 dB; it is preferable the refractive index of the Fresnel lens and the distal polymeric material 2610 are matched or similar. FIG. 26C depicts an embodiment with a RL or reference signal from the interface between the Fresnel lens and the distal polymeric material 2610; it is preferable the refractive index of the distal polymeric material 2610 is mismatched or different such that the RL is in the range of −14 dB to −40 dB, or −15 dB to −35 dB, or −20 dB to 35 dB or −25 dB to −35 dB. FIG. 26B depicts an exemplary Fresnel lens 2602 that may be used in the OCT imaging systems in FIGS. 26A and 26C. The lens 2602 may comprise a circular lens body with a plurality of concentric grates or gratings 2660. In this particular example, the lens 2602 is radially symmetrical with respect to a first axis 2662 and a second axis 2664 of the lens 2602, wherein both axes 2662, 2664 are transverse to the longitudinal axis of the optical fiber 2606, 26054 and are orthogonal to each other. In other variations, however, the configuration of the diffractive grating pattern may be different along the two axes 2662, 2664 to produce varying focusing power, or combination of beam focusing and collimation. This may be provided to adjust the beam profile to ensure a confocal beam, without requiring the use of an anamorphic lens.

Figure 27A:
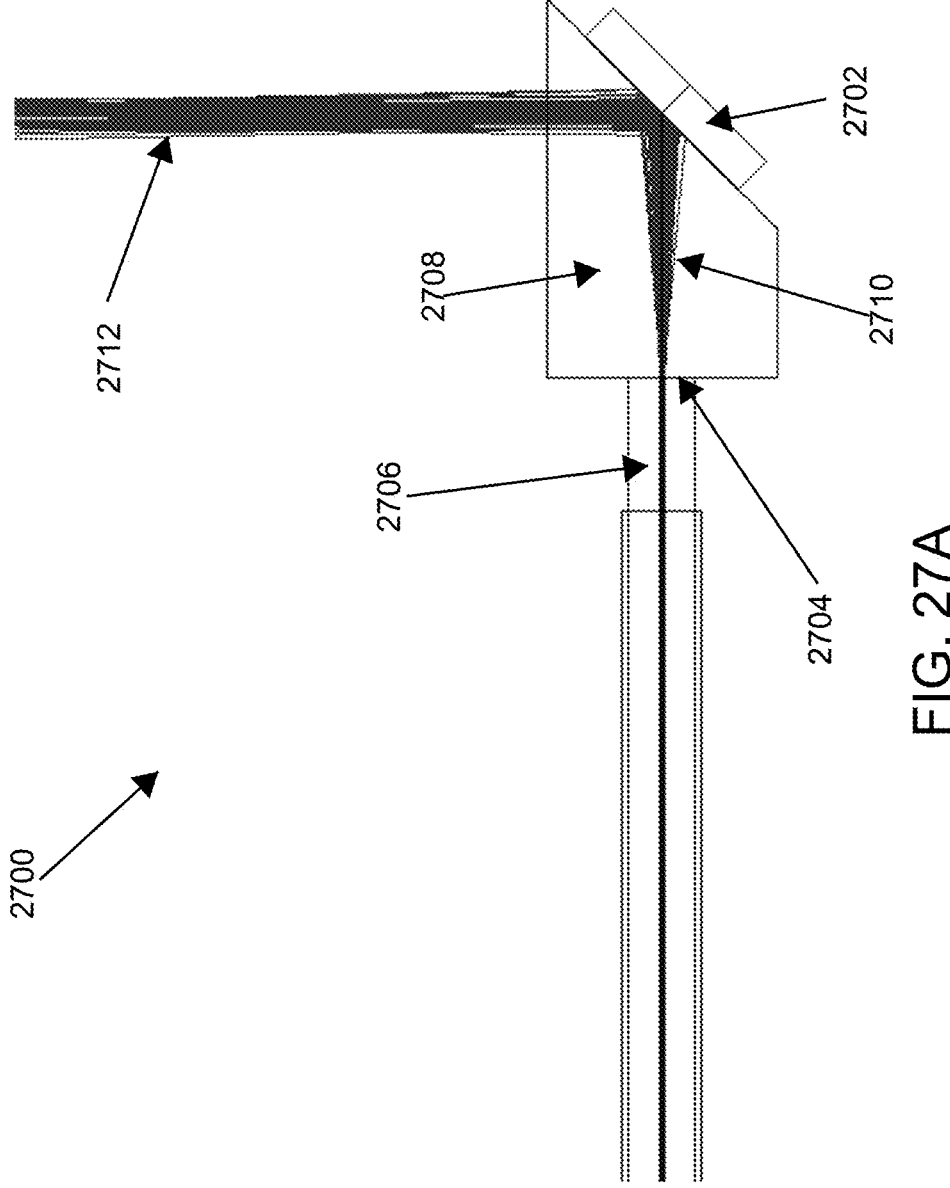
FIG. 27A is a schematic depiction of a Fresnel reflector in an exemplary OCT imaging system.

In still another embodiment, depicted in FIG. 27A, the OCT imaging system 2700 may lack a lens but comprises a reflector 2702 with a Fresnel diffractive grating formed or etched on its reflective surface. Like the mirrors or reflectors described herein, the Fresnel reflector 2702 may comprise of a layer of gold, silver, tin, nickel chromium, aluminum, dielectric or multilayer dielectric or other coatings thereof. Between the distal end 2704 of the optical fiber 2706 and the Fresnel reflector 2702, a low refractive index polymer 2708 as described herein may be provided, as described elsewhere herein. As the light beam 2710 exits the fiber 2706 and travel through the polymeric material 2708, it is reflected and collimated by the diffractive pattern of the Fresnel reflector 2702, and then exits the polymeric material 2708 to the target imaging location. The Fresnel reflector 2702 may be configured with an equivalent radius of curvature (R) in the range of −0.25 mm to −2.00 mm (concave), or −0.20 mm to −1.00 mm (concave); an inactive pitch angle in the range of 0 degrees to 75 degrees, a pitch frequency (pitch/mm) of 20 or greater, and a focal length (f) between the fiber to the reflector surface in the range of 200 μm to 1000 μm. The reflector 2702, as illustrated in FIG. 27F, like the Fresnel lens in FIG. 26B, may comprise a circular reflector body with a plurality of concentric circular grates, gratings or diffractive patterns 2760. In this particular example, the reflector 2702 is radially symmetrical with respect to a long axis 2762 and a short axis 2764 of the reflector 2702, but in other variations as discussed below, the configuration of the grating pattern may be different along the two axes 2762, 2764. The orientation of the long axis 2762 lies in the same plane as the longitudinal axis of the optical fiber 2706 and the reflected beam 2712, while the short axis 2764 is transverse and orthogonal to the long axis 2762 and to the longitudinal axis of the optical fiber 27. This may be provided to adjust the beam profile to ensure a confocal beam or beam waist, without requiring the use of an anamorphic lens having a concave reflective surface. In an embodiment of a Fresnel reflector 2702, the diffractive grating pattern imprinted on a flat surface with parameters including but not limited to the inactive pitch angle and pitch frequency may be gradually varied from the long axis 2762 to the short axis 2764 to ensure a confocal beam waist. In yet another embodiment of the Fresnel reflector 2702, the diffractive grating pattern imprinted on a flat surface may appear asymmetrical and elliptical with the long axis of the elliptical pattern matching the long axis 2762 and the short axis of the elliptical pattern matching the short axis 2764 to match the cross section of the incidence beam 2710 in the Fresnel reflector 2702.

Figure 27B:
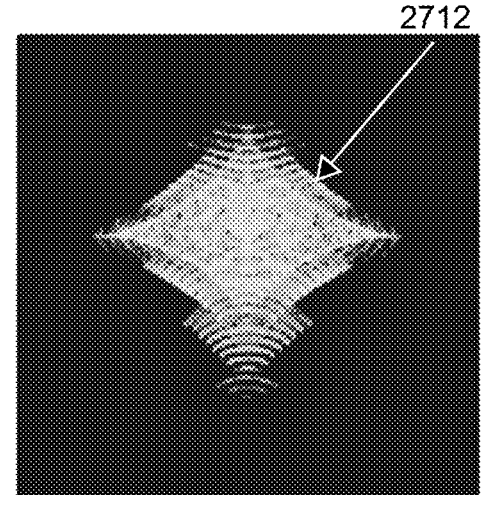
FIGS. 27B to 27E depict various beam profiles of the OCT imaging system in FIG. 27A at various focal lengths and their respective equivalent radii of curvature.
Figure 27C:
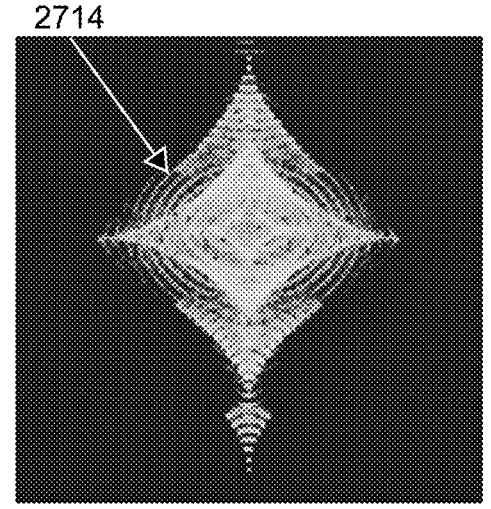
Figure 27D:
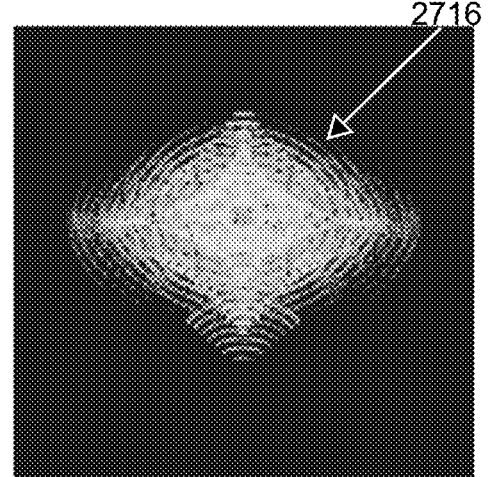
Figure 27E:
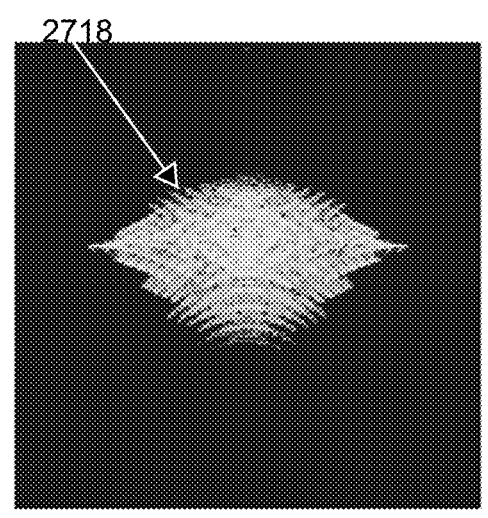
Figure 27F:
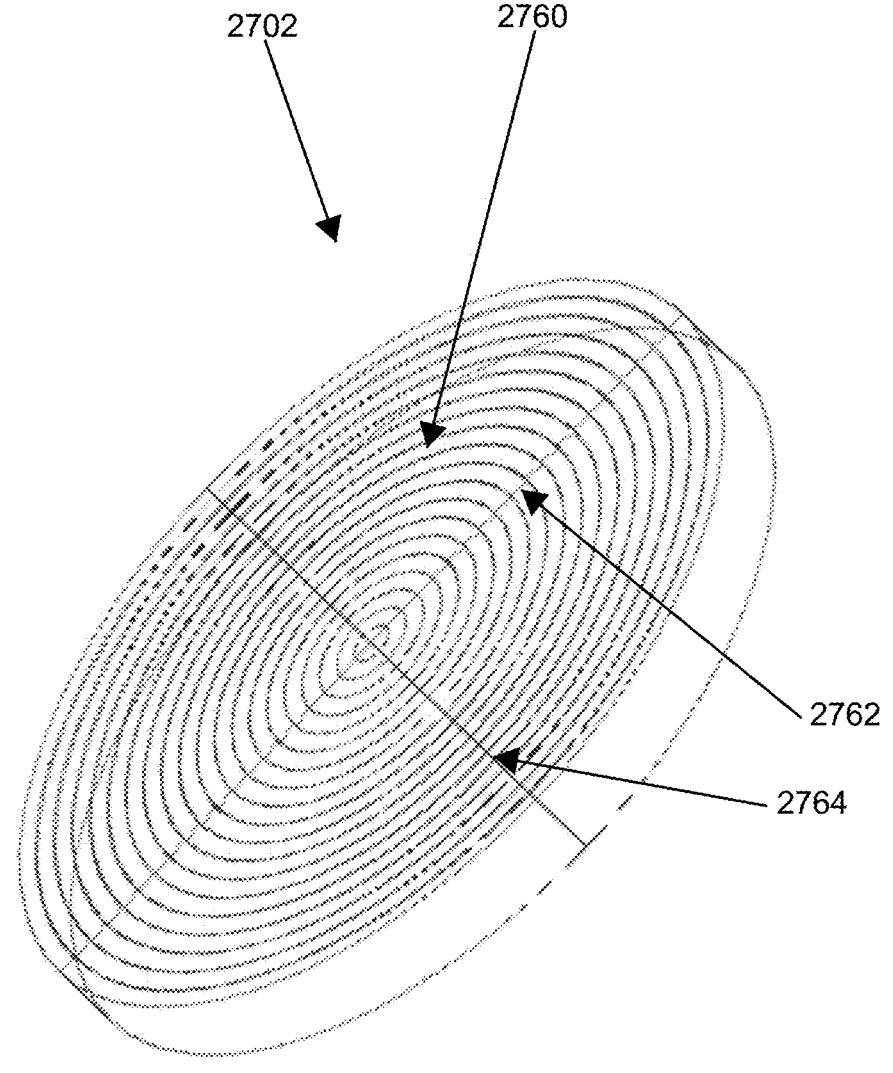
FIG. 27F is a superior perspective view of a Fresnel reflector.

FIGS. 27B to 27E depict various cross section beam profiles of the light beam 2710 in FIG. 27A. FIGS. 27B and 27C depicts the beam profile 2712, 2714 at a focal length (fiber to reflector surface distance) of 200 μm and at radii of curvature of −0.4 mm (concave) and a focal length of 250 μm and at radii of curvature of −0.5 mm (concave), respectively. FIG. 27D depicts the beam profile 2716 at a focal length of 300 μm and at a radius of curvature of −0.6 mm, while FIG. 27E depicts the beam profile 2718 at a focal length of 500 μm and a radius of curvature of −1.1 mm.

Figure 28A:
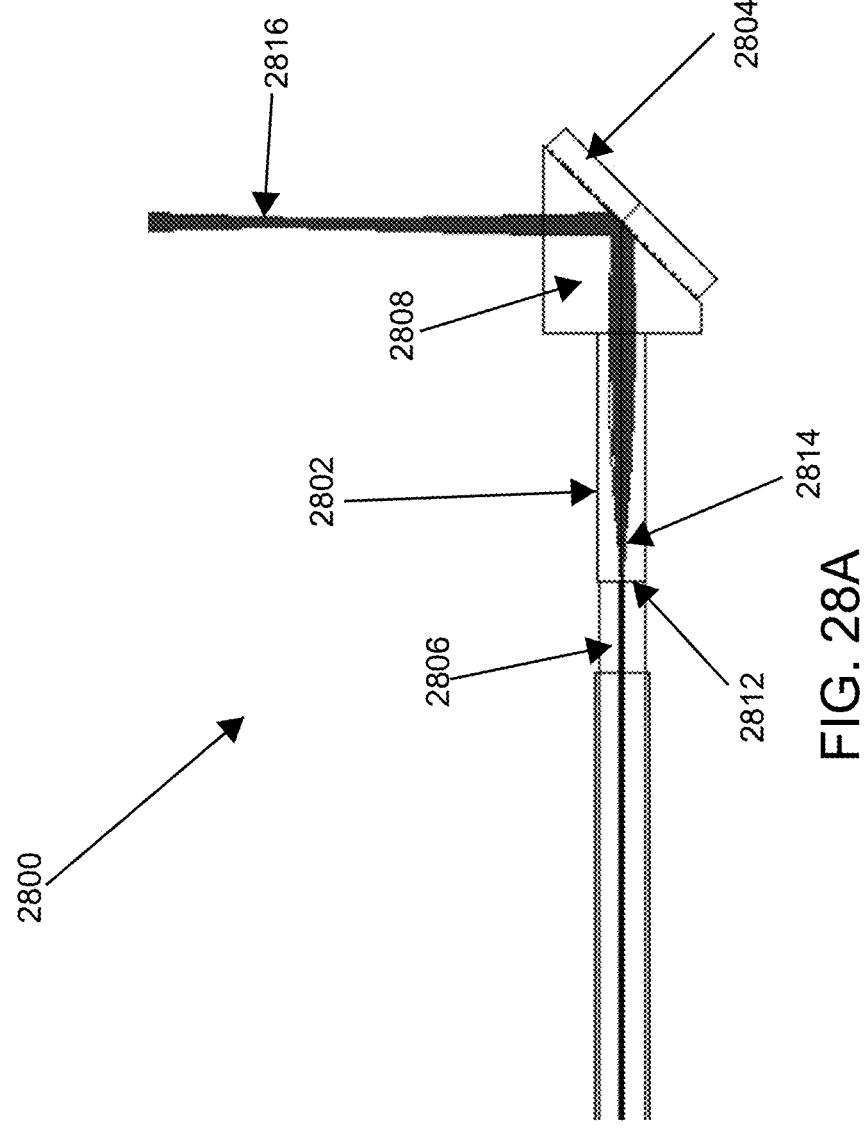
FIG. 28A is a schematic depiction of an exemplary OCT imaging system with a GRIN lens and a Fresnel reflector.

FIG. 28A depicts another embodiment of an OCT imaging system 2800 comprising both a GRIN lens 2802 and a Fresnel reflector 2804. In this example, the light beam 2814 exiting the optical fiber 2806 then is collimated by the GRIN lens 2802 and then enters the low refractive index polymeric material 2808 and then reflected by the Fresnel reflector 2804 before exiting the low reflective index polymeric material 2808 to reach the target location. As described with other embodiments herein, the end 2812 of the optical fiber 2806 may be a flat surface with an orientation 90 degrees to the longitudinal axis of the fiber 2806, or may be offset. The collimated light beam 2816 may have a diameter in the range of 20 μm to 200 μm, and the RL at the interface between the GRIN lens 2802 and the low refractive index material may be in the range of −14 dB to −28 dB, −14 dB to −40 dB, or −15 dB to −35 dB, or −20 dB to 35 dB or −25 dB to −35 dB.

Figures 28B, 28C:
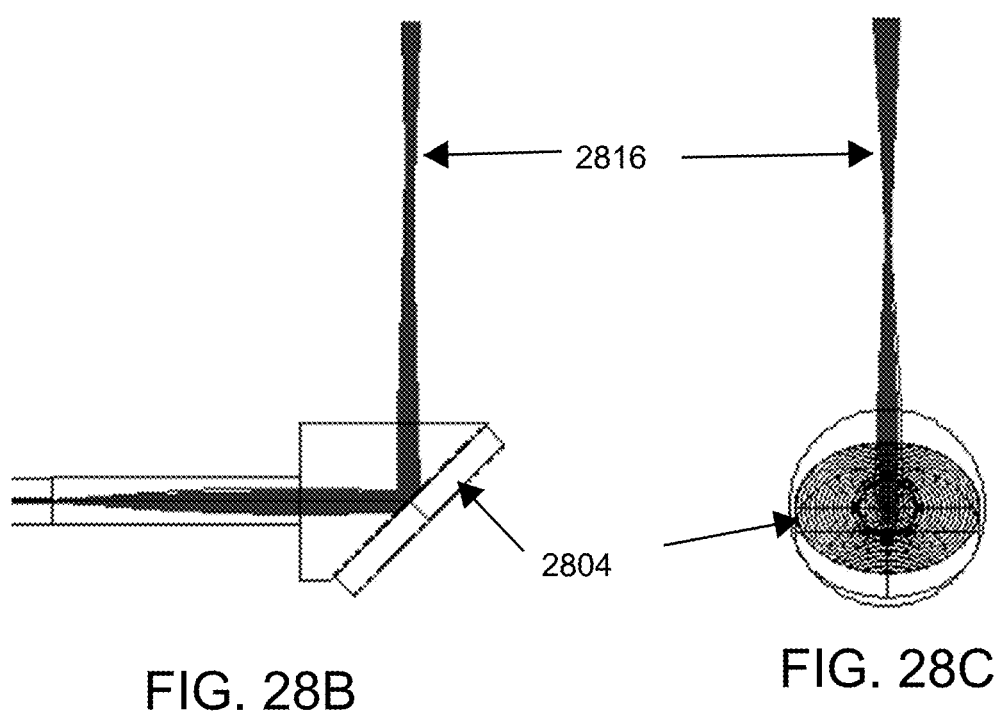
FIGS. 28B and 28C are schematic side and end views, respectively, of the beam profile of the OCT imaging system of FIG. 28A.
Figure 28D:
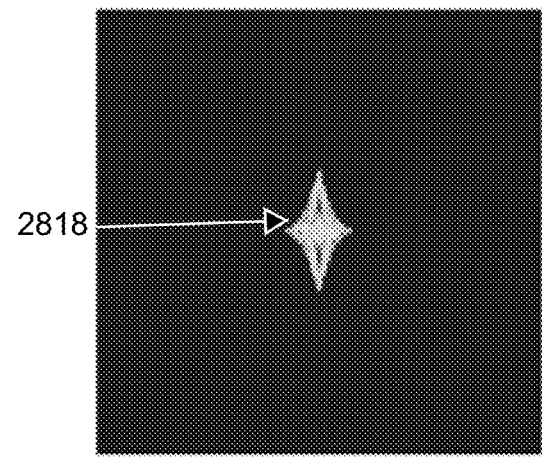
FIG. 28D depicts a beam profile of the OCT imaging system of FIG. 28A.

Depending on the desired configuration, the Fresnel reflector 2804 may be configured with an equivalent radius of curvature in the range of −0.25 mm to −30 mm to provide a focusing beam, or an equivalent radius of curvature in the range of −30 mm to −infinity for a collimated beam. As noted previously, the diffractive pattern of the Fresnel reflector 2804 may be configured with a radially symmetric or an asymmetric pattern. Whether the light beam from the GRIN lens is converging (focusing), diverging, collimated or adequately collimated, a Fresnel reflector 2702 or 2804 placed at 45 degrees as depicted in FIG. 27A and FIG. 28A will introduce astigmatism exhibiting a deviation or an offset of the beam focus or combination of beam collimation/focus along the long axis 2762 and short axis 2764. In variations where some correction to an astigmatic light beam is desired, an elliptical or asymmetric diffractive pattern may be provided. Depending on the axis of the astigmatism, the long axis or the short axis of the Fresnel reflector 2804 may be adjusted to provide an elliptical diffractive pattern to compensate for the astigmatism to match the incidence beam at the 45-degree tilt of the reflector 2804. FIGS. 28B and 28C are schematic side and end views of the reflector 2804 and the profile of the reflected light beam 2816, with an exemplary astigmatic beam profile 2818 depicted in FIG. 28D. To compensate for the asymmetric profile 2818, the long axis 2762 and the short axis 2764 of a reflector 2702, as depicted in FIG. 27F, may be adjusted to an elliptical shape to compensate for any astigmatism in the incidence beam, so that the reflected beam is sufficiently collimated, or confocal if it were a focusing beam. Alternatively, the diffractive grating pattern imprinted on a flat surface with parameters including but not limited to the inactive pitch angle and pitch frequency may be gradually varied from the long axis 2762 to the short axis 2764 to ensure a confocal beam waist. The use of a Fresnel reflector 2702 or 2804 avoids the need for an anamorphic lens having a concave reflective surface.

Figure 10:
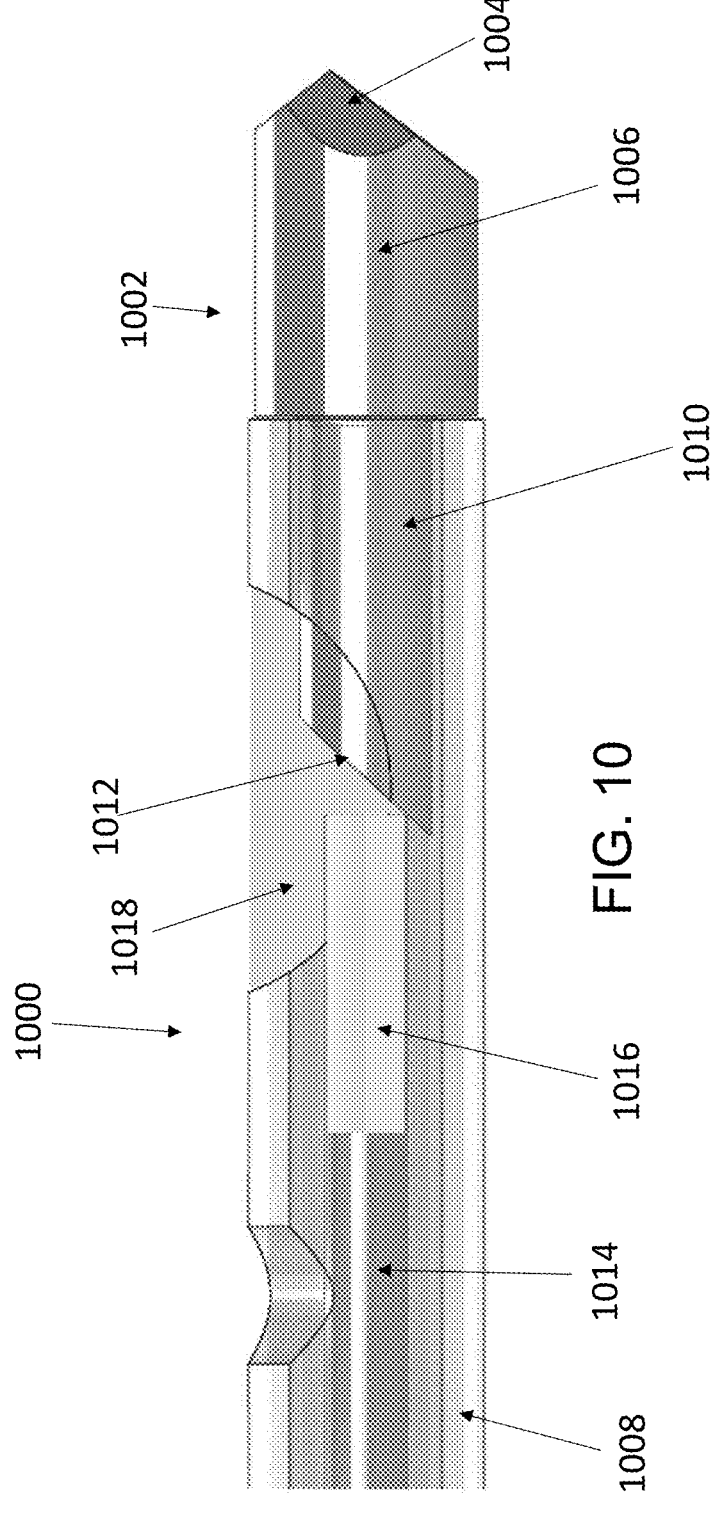
FIG. 10 is a schematic longitudinal cross-sectional view of another exemplary embodiment of an imaging crosser device.

FIG. 10 depicts another variation of the imaging cross device 1000, similar to device 900 but wherein the optical element 1002 comprise a tapered distal end 1004 with an enlarged diameter body 1006 that is external to the hypotube 1008, and a smaller diameter proximal stem 1010 with a proximal reflecting surface 1012. The proximal reflecting surface 1012 may be angled at 45 degree, or off 45 degree such as 48 degree but no more than 45+/−5 degrees. As with device 900, a hypotube 1014, optical fiber 1016, lens 1018 and adhesive 1020 are provided.

Figure 11:
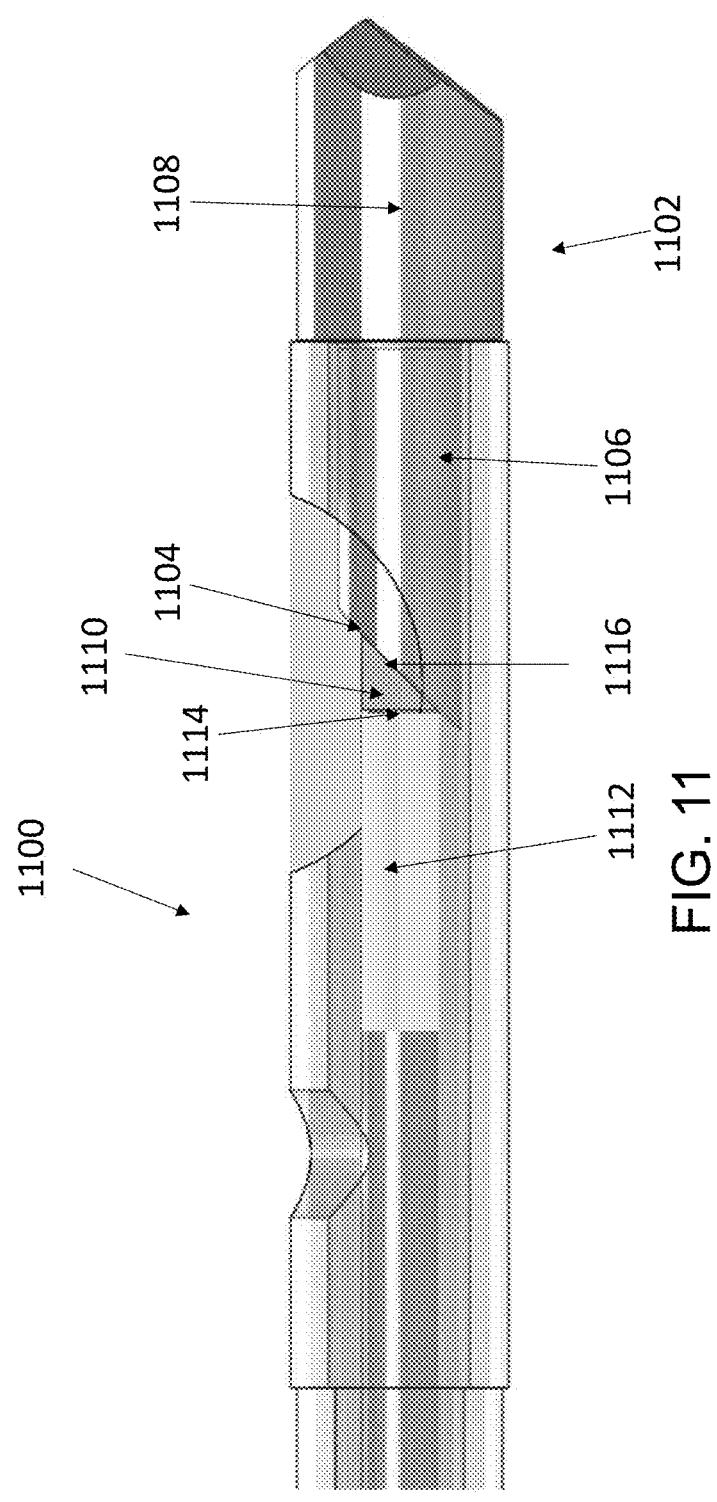
FIG. 11 is a schematic longitudinal cross-sectional view of another exemplary embodiment of an imaging crosser device.

FIG. 11 depicts still another embodiment of an imaging crosser device 1100, wherein the optical element 1102 comprises a proximal angled surface 1104 on a stem 1106 of an enlarged cutting head 1108, but with the addition of a prism 1110 inserted between the lens 1112 and the proximal angled surface 1104. The prism 1110 comprises an orthogonal proximal surface 1114 that is optically coupled to the lens 1112, and a 45-degree angled distal end 1116 that is bonded to the proximal angled surface 1104 of the stem 1106, with the prism having the longest dimension no larger than 255 um. The angled distal end (or the hypotenuse) 1116 of the prism 1110 may be coated or bonded to the stem 1106 using an aluminum or other metallic reflecting coating.

Figures 12A, 12B:
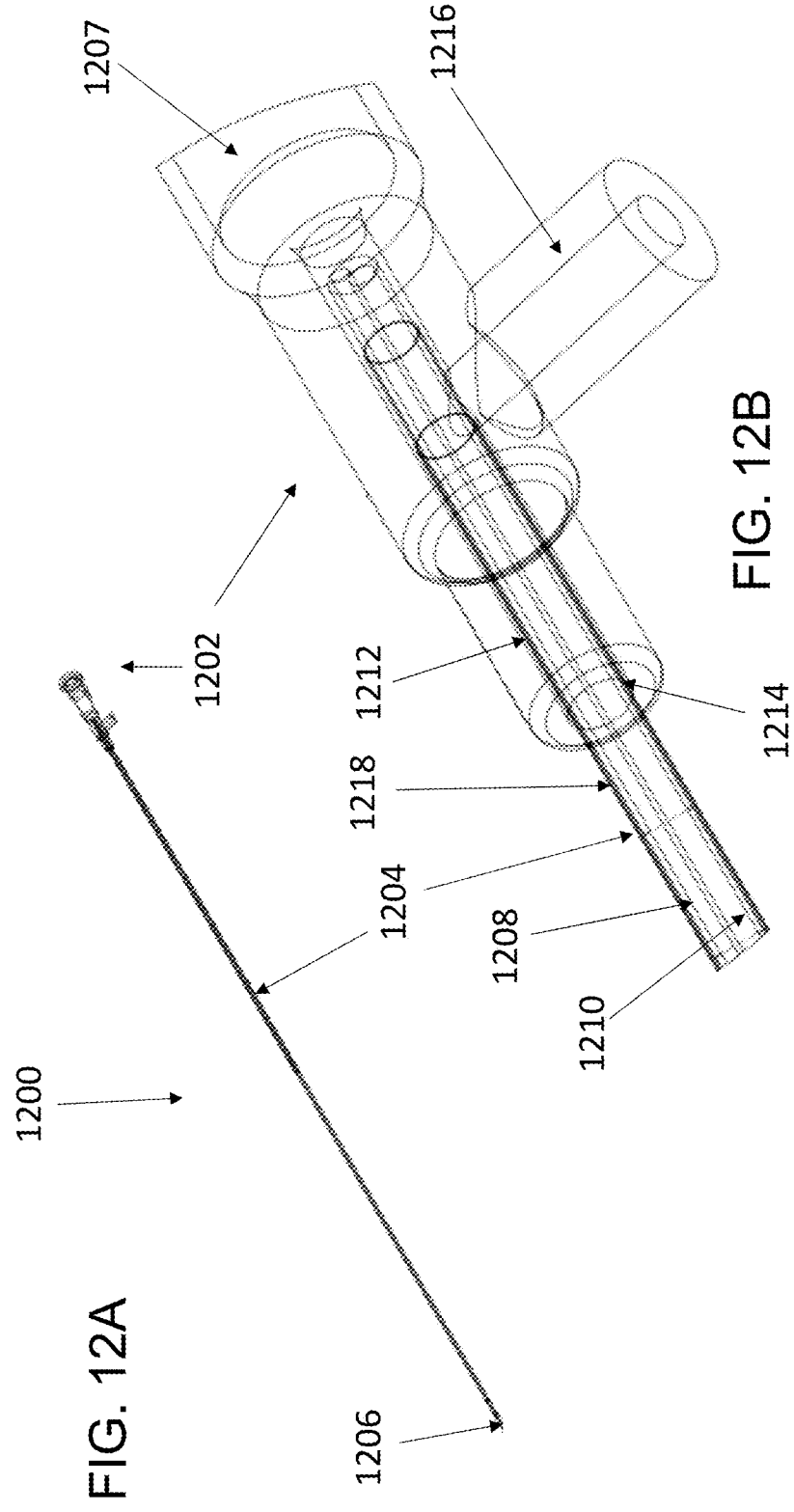
FIG. 12A depicts an exemplary guide catheter configured for use with the imaging crosser device.
FIG. 12B is schematic view of the proximal hub and proximal shaft of the guide catheter in FIG. 12A.
Figures 13, 14:
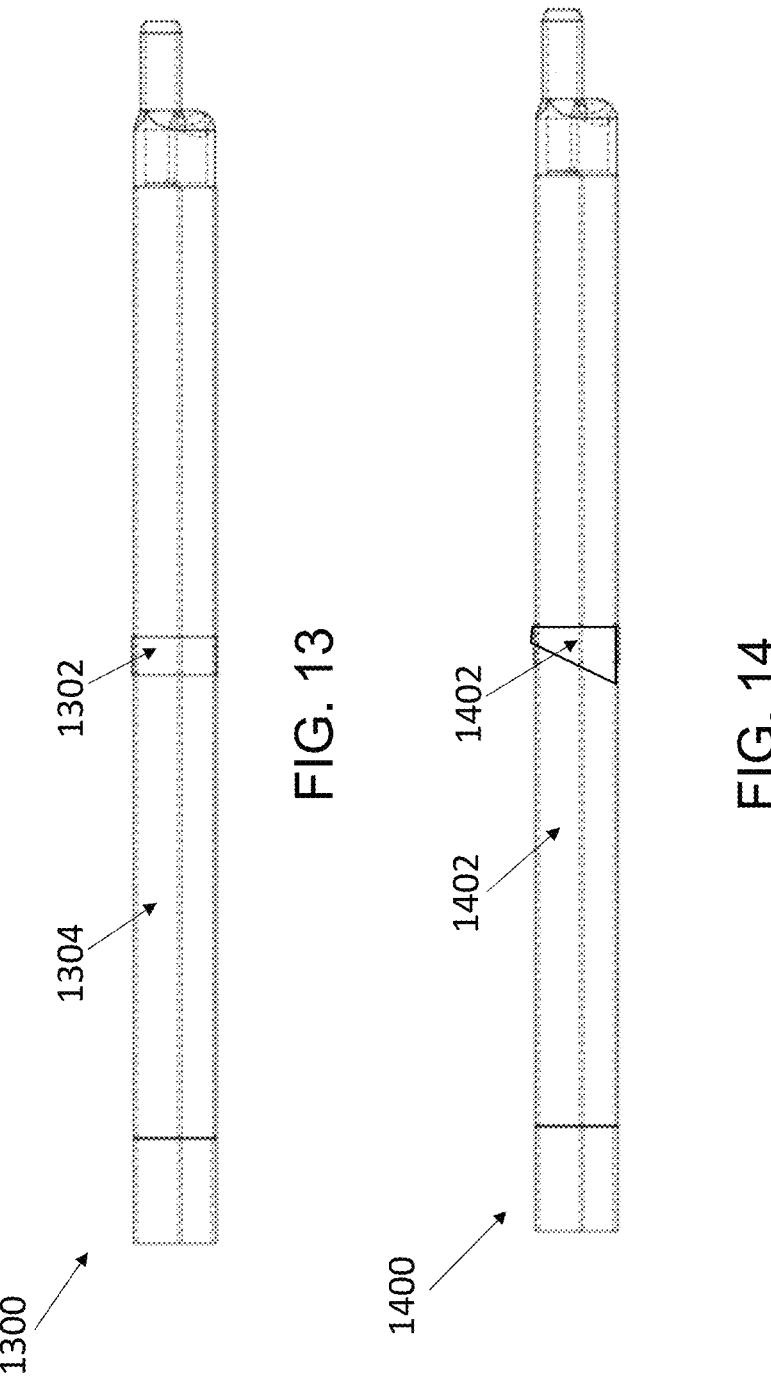
FIGS. 13 and 14 schematically depict different variations of marker bands that may be provided on the guide catheter.

In use, the imaging crosser devices described herein may be used in conjunction with a traditional guiding catheters for accessing the desired target locations for diagnostic assessment and/or therapeutic treatment. In other variations of the imaging crosser devices, a dual-lumen guide catheter may be used. Referring to FIG. 12A, the guide catheter 1200 may comprise a proximal hub 1202, a catheter body 1204 and a distal tip 1206. Referring to FIG. 12B, the proximal hub 1204 may comprise one or more proximal openings 1206 which communicate with two or more catheter body lumens 1208, 1210 of the catheter body 1204. As depicted in FIG. 12B, the catheter body 1204 is partially located inside the distal lumen 1212 and distal opening 1214 of the hub 1202. The hub may further comprise an optional flushing port 1216, which may be configured to be in fluid communication with one or both of the catheter body lumens 1208, 1210. In some variations, the catheter body 1204 may comprise separate tubular bodies for each catheter body lumens 1208, 1210, which located inside an overtube 1218, as depicted in FIG. 12B. In these variations, the flush port may be in fluid communication in the tubular lumen of the overtube 1218 but outside catheter body lumens 1208, 1210. The catheter lumens 1208, 1210 may have the same or different diameters. In the particular example depicted in FIG. 12B, catheter lumen 1208 comprises a smaller diameter of 0.016" for use with a guidewire, and catheter lumen 1210 comprises a larger diameter of 0.022" or 0.025" to receive the imaging crosser device. In FIGS. 13 and 14 depicting variations of the distal embodiment of the dual-lumen guide catheter 1300 and 1400, the last 2 to 6 inches (50.8 to 152.4 mm) of the distal end comprise optically transparent materials. In another embodiment, 3 to 5 inches (76.2 to 127.0 mm) of the distal end 1300 and 1400 comprise optically transparent materials.

The distal end 1220 of the catheter body 1204 may be attached to a catheter tip 1220. Referring to FIG. 15, the catheter tip 1220 may comprise a cylindrical base 1222 with a proximal surface 1224 and comprises a corresponding opening for tip lumens 1226 and 1228, which are configured to be in fluid communication with catheter body lumens 1208 and 1210. In this particular catheter tip 1220, tip lumen 1226 extends distally a greater distance from the proximal surface 1224 than tip lumen 1228, along an extension tube 1230 that projects distally from the cylindrical base 1222. One or more angled transition surfaces 1232 may be provided on the outer surface of the cylindrical base 1222 in order to provide a smooth transition from to the extension tube 1230.

In some variations of the guide catheters used with the imaging crosser devices, one or more side openings along the catheter body and/or catheter tip may be provided so that the guidewire may be manipulated to exit the guide catheter proximally to the distal opening 1334 of the guidewire tip lumen 1228. In FIG. 16, for example, a side opening 1602 is provided in the catheter tip 1600. This may be in addition to catheter body openings that are provided, e.g. at 20 cm, 40 cm and/or 60 cm distances along the catheter body as measured from the hub.

As shown in FIGS. 15 and 16, in some variations, the guidewire tip lumens 1226 and 1604 may comprise a generally linear configuration, where the lumen extends axially without any angle or deviation from the longitudinal axis. In other examples, or with the imaging crosser device tip lumens 1228 and 1606, however, the lumens 1228 and 1606 may be provided with angled regions to direct the inserted devices outwardly angle, away from the extension tube 1230. This may help with facilitating diagnosis or treatment of eccentric lesions on the anatomy. In other examples, however, the lumens 1228 and 1606 may have a straight orientation.

FIGS. 13 and 14 depict additional features of the guide catheter 1300 and 1400, which may include radiopaque marker bands 1302 and 1402 located along the catheter body 1304 and 1404, respectively. The marker band 1302 comprises a ring-like configuration with uniform length, while the marker band 1402 comprises an asymmetric configuration, which may facilitate assessment of the catheter orientation and/or location.

The operation of the optical systems is generally described with respect to light being emitted by the optical system towards a target area. However, one of skill in the art would appreciate that since optical paths may typically be reversible, the beam path may also represent a field of view 'seen' by the optical system (e.g., reach a receiver of the optical system). Thus, an imaging beam emitted by an optical fiber may also represent (all or part of) a pathway along which received light may return to the fiber.

Certain materials have been described herein based on their interaction with light (e.g., opaque, reflective, transmissive, refractive, etc.). These descriptors may refer to that material's interactions with a range of wavelength(s) emitted by the system and/or that the receiver is sensitive to. It would be understood by one of skill in the art that a given material's properties vary at different ranges of wavelengths and that different materials may be desirable for different ranges of wavelengths. The description of a particular example material is not intended to limit the disclosure to a range of wavelengths over which that particular example material has the desired optical properties. Similarly, the description of a particular wavelength is not intended to limit the system to only those wavelengths. The term 'light' may be used throughout the spectrum to represent electromagnetic radiation, and is not intended to limit the disclosure to electromagnetic radiation within the visible spectrum. The term 'light' may refer to electromagnetic radiation of any wavelength.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An imaging device comprising:
an outer shaft with a lumen;
an optical fiber located within the lumen of the outer shaft;
a reflective element disposed in the lumen of the outer shaft, wherein the reflective element comprises an optical material with an angled surface configured to an imaging beam;
a lens located between the optical fiber and the reflective element, wherein the lens is tilted between 0.1 to 2.0 degrees; and
a first optical filler between the distal end of the optical fiber and the reflective element, the first optical filler comprising a UV cured adhesive a refractive index of less than 1.40.

2. The imaging device of claim 1, wherein the refractive index of the first optical filler is in the range of 1.30 to 1.40.

3. The imaging device of claim 1, wherein the refractive index of the first optical filler is in the range of 1.33 to 1.38.

4. The imaging device of claim 1, wherein the first optical filler comprises an aliphatic urethane acrylate and an acrylic monomer.

5. The imaging device of claim 4, wherein the aliphatic urethane acrylate percentage is 30% to 70% and the acrylic monomer is 70% to 30%.

6. The imaging device of claim 5, wherein the aliphatic urethane acrylate percentage is 40% to 65% and the acrylic monomer is 60% to 35%.

7. The imaging device of claim 4, wherein the viscosity of the first optical filler is in the range of 1000 to 3000 cps.

8. The imaging device of claim 7, wherein the viscosity of the first optical filler is in the range of 1500 to 3000 cps.

9. The imaging device of claim 7, wherein the viscosity of the first optical filler is in the range of 2000 to 2500 cps.

10. The imaging device of claim 1, wherein the lens is a Fresnel lens.

11. The imaging device of claim 1, wherein the lens is plano-convex or double-convex lens.

12. The imaging device of claim 1, wherein the lens is a GRIN lens.

13. The imaging device of claim 1, further comprising a non-clad fiber followed by a GRIN lens between the optical fiber and the reflective element.

14. The imaging device of claim 1, further comprising a second optical filler located between the optical fiber and the lens.

15. The imaging device of claim 14, wherein the first optical filler and the second optical filler comprises different materials.

16. The imaging device of claim 14, wherein the first and second optical filler comprise the same constituents but at different ratios, and wherein both the first and second optical filler have a refractive index of less than 1.50.

17. The imaging device of claim 1, wherein the angled surface of the reflection element comprises a Fresnel diffractive pattern.

18. The imaging device of claim 17, wherein the Fresnel diffractive pattern comprises varying degree of collimating or focusing power along its long axis, short axis and in between the long and short axes.

19. The imaging device of claim 17, further comprising a lens located between the optical fiber and the reflection element.

20. The imaging device of claim 19, wherein the lens is a GRIN lens.

21. The imaging device of claim 19, wherein the first optical filler is located between the lens and the reflective element.

22. The imaging device of claim 1, wherein the reflection element further comprises a tapered distal end protruding from the lumen of the outer shaft, wherein the tapered distal end is configured to penetrate tissue.

23. The imaging device of claim 1, wherein a collimating lens is located between the optical fiber and the first optical filler.

24. The imaging device of claim 23, wherein the collimating lens is a GRIN lens, plano-convex, biconvex or a Fresnel lens.

25. The imaging device of claim 24, wherein the collimating lens is a GRIN lens with at least 0.75 pitch or more in unit length.

26. The imaging device of claim 1, wherein the first optical filler is further located between the lens and the reflection element.

* * * * *